(12) United States Patent
Reddy et al.

(10) Patent No.: US 10,889,561 B2
(45) Date of Patent: *Jan. 12, 2021

(54) PROCESS OF MAKING SOMATOSTATIN MODULATORS

(71) Applicant: Crinetics Pharmaceuticals, Inc., San Diego, CA (US)

(72) Inventors: Jayachandra P. Reddy, West Palm Beach, FL (US); Mahmoud Mirmehrabi, Halifax (CA)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/592,595

(22) Filed: Oct. 3, 2019

(65) Prior Publication Data

US 2020/0048219 A1 Feb. 13, 2020

Related U.S. Application Data

(63) Continuation of application No. 16/249,729, filed on Jan. 16, 2019, now Pat. No. 10,464,918.

(60) Provisional application No. 62/618,538, filed on Jan. 17, 2018.

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,115,634 B2 | 10/2006 | Thurieau et al. | |
| 7,648,984 B2 | 1/2010 | Miller et al. | |
| 7,767,817 B2 | 8/2010 | Wang et al. | |
| 9,120,749 B2 | 9/2015 | Matsuo et al. | |
| 9,309,222 B2 | 4/2016 | Leonard et al. | |
| 9,896,432 B2 | 2/2018 | Zhao et al. | |
| 9,902,703 B2 | 2/2018 | Zhao et al. | |
| 9,957,267 B2 | 5/2018 | Zhu et al. | |
| 1,035,154 A1 | 7/2019 | Zhao et al. | |
| 1,046,491 A1 | 11/2019 | Reddy et al. | |
| 10,597,377 B2 * | 3/2020 | Zhao | C07D 471/04 |
| 2003/0153553 A1 | 8/2003 | Mattei et al. | |
| 2005/0009815 A1 | 1/2005 | Devita et al. | |
| 2009/0258853 A1 | 10/2009 | Eastman et al. | |
| 2015/0232478 A1 | 8/2015 | Ishida et al. | |
| 2015/0239900 A1 | 8/2015 | Li et al. | |
| 2015/0284337 A1 | 10/2015 | Aubele et al. | |
| 2020/0190053 A1 | 6/2020 | Zhao et al. | |

FOREIGN PATENT DOCUMENTS

| | | |
|---|---|---|
| EP | 3053916 B1 | 1/2019 |
| KR | 20160062023 A | 6/2016 |
| WO | WO-03045920 A1 | 6/2003 |
| WO | WO-2008051272 A2 | 5/2008 |
| WO | WO-2010041054 A1 | 4/2010 |
| WO | WO-2012162254 A1 | 11/2012 |
| WO | WO-2013050996 A2 | 4/2013 |
| WO | WO-2016049568 A1 | 3/2016 |
| WO | WO-2018013676 A1 | 1/2018 |
| WO | WO-2019143718 A1 | 7/2019 |

OTHER PUBLICATIONS

Berge et al. Pharmaceutical Salts. Journal of Pharmaceutical Sciences 66(1):1-19 (Jan. 1977).
Cescato et al. Agonist-Biased Signaling at the sst2A Receptor: The Multi-Somatostatin Analogs KE108 and SOM230 Activate and Antagonize Distinct Signaling Pathways. Mol Endocrinol 24(1):240-249 (2010).
Esch et al. Primary structure of ovine hypothalamic somatostatin-28 and somatostatin-25. PNAS USA 77:6827-6831 (1980).
Garrett et al. The Art of Meeting Palladium Specifications in Active Pharmaceutical Ingredients Produced by Pd-Catalyzed Reactions. Adv. Synth. Catal. 346:889-900 (2004).
Gradiz et al. MIA PaCa-2 and PANC-1—pancreas ductal adenocarcinoma cell lines with neuroendocrine differentiation and somatostatin receptors. Scientific Reports 6:21648 (15 pgs.) (2016).
Guideline on the Specification Limits for Residues of Metal Catalysts. European Medicines Agency. Pre-authorization Evaluation of Medicines for Human Use, London (Jan. 2007) (pp. 1-32).
Patel et al. Somatostatin receptors. Trends Endocrinol Metab 8:398-405 (1997).
PCT/US2017/041694 International Search Report and Written Opinion dated Dec. 12, 2017.
PCT/US2019/013844 International Search Report and Written Opinion dated May 1, 2019.
Pradayrol et al. N-terminally extended somatostatin: the primary structure of somatostatin-28. FEBS Letters 109:55-58 (1980).
Prasoon et al. Role of somatostatin and somatostatin receptor type 2 in postincisional nociception in rats. Neropeptides 49:47-54 (2015).
Reisine et al. Molecular biology of somatostatin receptors. Endocr Rev 16:427-442 (1995).
Song et al. Amine-Mediated Transimination and Aromatization-Triggered Domino Reaction in the Synthesis of Polyfunctionalized 4-Aminoquinolines. Org Lett 18(20):5328-5331 (2016).
Stahl et al. Handbook of Pharmaceutical Salts. Verlag Helvetica Chimica Acta, Zurich, 2002.
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).

* cited by examiner

*Primary Examiner* — Zinna Northington Davis
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

10 Claims, 15 Drawing Sheets

X-ray powder diffraction (XRPD) pattern of Compound A, mono-HCl salt

Differential Scanning Calorimetry (DSC) thermogram of Compound A, mono-HCl salt

Thermogravimetric Analysis/Differential Scanning Calorimetry (TGA/DSC) thermogram of Compound A, mono-HCl salt Infrared (IR) spectrum of Compound A, mono-HCl salt X-ray powder diffraction (XRPD) pattern of Compound A, di-HCl salt Differential Scanning Calorimetry (DSC) thermogram of Compound A, di-HCl salt Thermogravimetric Analysis (TGA) thermogram of Compound A, di-HCl salt Infrared (IR) spectrum of Compound A, di-HCl salt

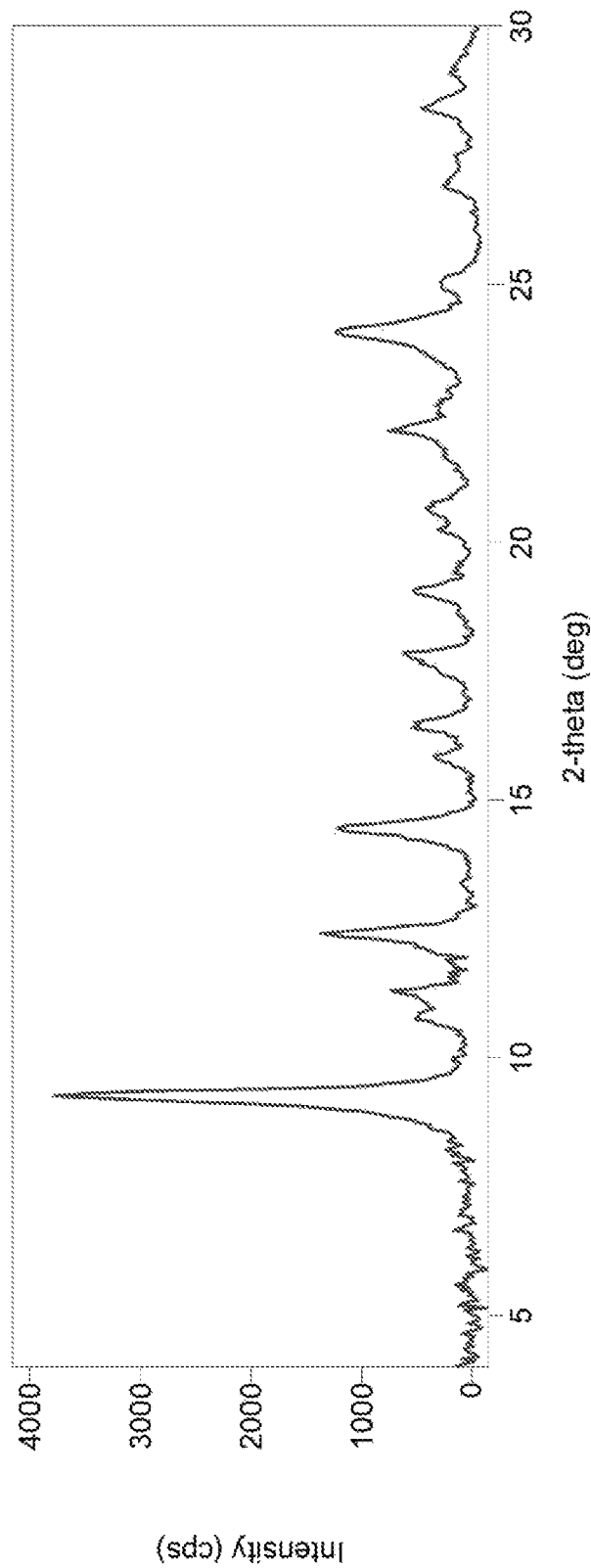

X-ray powder diffraction (XRPD) pattern C of Compound A, free base

Differential Scanning Calorimetry (DSC) thermogram of Pattern C of Compound A, free base Thermogravimetric Analysis (TGA) thermogram of Pattern C of Compound A, free base X-ray powder diffraction (XRPD) pattern of Compound A, mono-HCl salt before (bottom spectra) and after (top spectra) Dynamic Vapor Sorption (DVS) testing between 2 and 95% Relative Humidity (RH)

X-ray powder diffraction (XRPD) pattern of Compound A, di-HCl salt before (bottom spectra) and after (top spectra) Dynamic Vapor Sorption (DVS) testing between 2 and 95% Relative Humidity (RH)

PROCESS OF MAKING SOMATOSTATIN MODULATORS

RELATED APPLICATIONS

This application is a continuation application of U.S. application Ser. No. 16/249,729, filed Jan. 16, 2019, which claims the benefit of U.S. Provisional Patent Application No. 62/618,538 filed on Jan. 17, 2018, each of which is herein incorporated by reference in its entirety.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

In one aspect, described herein the compound 3-[4-(4-amino-piperidin-1-yl)-3-(3,5-difluoro-phenyl)-quinolin-6-yl]-2-hydroxy-benzonitrile monohydrochloride, or solvate thereof, having the following structure:

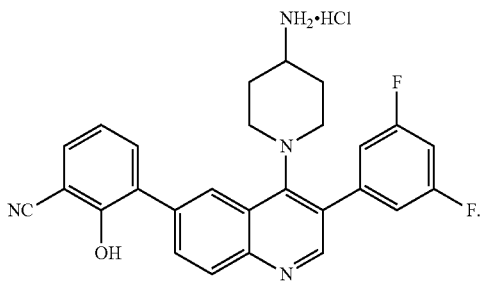

In another aspect, described herein is crystalline 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has: an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta; an X-ray powder diffraction (XRPD) pattern substantially the same as shown in FIG. 1; a Differential Scanning Calorimetry (DSC) thermogram with an endotherm having an onset at about 207° C. and a peak at about 220° C.; a Differential Scanning Calorimetry (DSC) thermogram substantially the same as shown in FIG. 2(a); a Thermogravimetric Analysis (TGA) thermogram substantially the same as shown in FIG. 2(b); an infrared (IR) spectrum with peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$; an infrared (IR) spectrum substantially the same as shown in FIG. 3; an unchanged XRPD when heated up to about 200° C., upon exposure to more than 90% relative humidity for about 24 hours, or upon exposure to about 75% RH and 40° C. over one week, or combinations thereof; or combinations thereof.

In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an XRPD pattern further comprises peaks at 20.7° 2-Theta, 23.3° 2-Theta, 23.4° 2-Theta, 23.6° 2-Theta, 27.1° 2-Theta, and 28.0° 2-Theta. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an X-ray powder diffraction (XRPD) pattern substantially the same as shown in FIG. 1. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has a Differential Scanning Calorimetry (DSC) thermogram with an endotherm having an onset at about 207° C. and a peak at about 220° C. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has a Differential Scanning Calorimetry (DSC) thermogram substantially the same as shown in FIG. 2(a). In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an unchanged XRPD when heated up to about 200° C. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an unchanged XRPD upon exposure to more than 90% relative humidity for 24 hours and upon exposure to about 75% RH and 40° C. over one week. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an infrared (IR) spectrum with characteristic peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$. In some embodiments, the crystalline 3-[4-(4-amino-piperidin-1-yl)-3-(3,5-difluoro-phenyl)-quinolin-6-yl]-2-hydroxy-benzonitrile monohydrochloride, or solvate thereof, has an infrared (IR) spectrum substantially the same as the IR spectrum shown in FIG. 3.

In another aspect, described herein is a pharmaceutical composition comprising crystalline 3-[4-(4-amino-piperidin-1-yl)-3-(3,5-difluoro-phenyl)-quinolin-6-yl]-2-hydroxy-benzonitrile monohydrochloride, or solvate thereof, and at least one pharmaceutically acceptable excipient. In some embodiments, the pharmaceutical composition is formulated for administration to a mammal by oral administration. In some embodiments, the pharmaceutical composition is in the form of a solid form pharmaceutical composition. In some embodiments, the pharmaceutical composition is in the form of a tablet, a pill, or a capsule.

In another aspect, described herein is a method of making crystalline 3-[4-(4-amino-piperidin-1-yl)-3-(3,5-difluoro-phenyl)-quinolin-6-yl]-2-hydroxy-benzonitrile monohydrochloride, or solvate thereof, comprising the steps of:

(a) slurrying 3-[4-(4-amino-piperidin-1-yl)-3-(3,5-difluoro-phenyl)-quinolin-6-yl]-2-hydroxy-benzonitrile dihydrochloride in 5 volumes of isopropanol:water (1:1) mixture;
  (i) heating the slurry of (a) to about 45° C.;
  (ii) adding about 0.5 to about 1.2 equivalents of ammonium hydroxide solution, sodium bicarbonate solution, or sodium hydroxide solution to the heated slurry of step (a)(i) to achieve a pH of about 4.0-6.0;
  (iii) adding water over about 2 hours to the mixture of step (a)(ii); and
  (iv) filtering the slurry of step (a)(iii) to provide 3-[4-(4-amino-piperidin-1-yl)-3-(3,5-difluoro-phenyl)-quinolin-6-yl]-2-hydroxy-benzonitrile monohydrochloride, or solvate thereof;
or
(b) adding a suitable solvent to 3-[4-(4-amino-piperidin-1-yl)-3-(3,5-difluoro-phenyl)-quinolin-6-yl]-2-hydroxy-benzonitrile;
  (i) adding about 1 equivalent of hydrochloric acid to the mixture of solvent and 3-[4-(4-amino-piperidin-1-yl)-3-(3,5-difluoro-phenyl)-quinolin-6-yl]-2-hydroxy-benzonitrile of (b); and
  (ii) filtering the solids resulting from step (b)(ii) to provide 3-[4-(4-amino-piperidin-1-yl)-3-(3,5-difluoro-phenyl)-quinolin-6-yl]-2-hydroxy-benzonitrile monohydrochloride, or solvate thereof;
or
(c) stirring 3-[4-(4-amino-piperidin-1-yl)-3-(3,5-difluoro-phenyl)-quinolin-6-yl]-2-hydroxy-benzonitrile dihydrochloride in about 20 volumes to about 50 volumes of water; and
  (i) filtering the solids of step (c) to provide 3-[4-(4-amino-piperidin-1-yl)-3-(3,5-difluoro-phenyl)-quinolin-6-yl]-2-hydroxy-benzonitrile monohydrochloride, or solvate thereof.

In some embodiments, ammonium hydroxide solution is used in (a)(ii). In some embodiments, the amount of ammonium hydroxide solution used in (a)(ii) is about 0.8 equivalents and the pH achieved is about 4.5-4.7.

In some embodiments, the suitable solvent in (b) is methanol, ethanol, isopropyl alcohol, acetone, methyl acetate, ethyl acetate, tetrahydrofuran, tetrahydropyran, water, or combinations thereof.

In another aspect, described herein is a process for the synthesis of 3-[4-(4-amino-piperidin-1-yl)-3-(3,5-difluoro-phenyl)-quinolin-6-yl]-2-hydroxy-benzonitrile dihydrochloride:

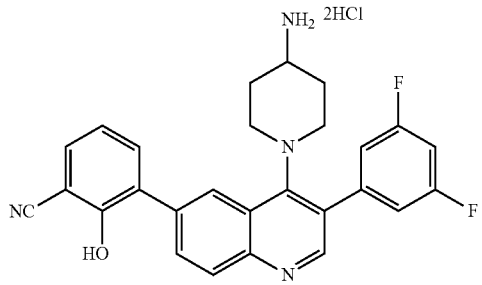 [SMILES: N#Cc1cccc(-c2ccc3ncc(-c4cc(F)cc(F)c4)c(N4CCC(N)CC4)c3c2)c1O]

comprising the step of treating Compound A-VI:

Compound A-VI

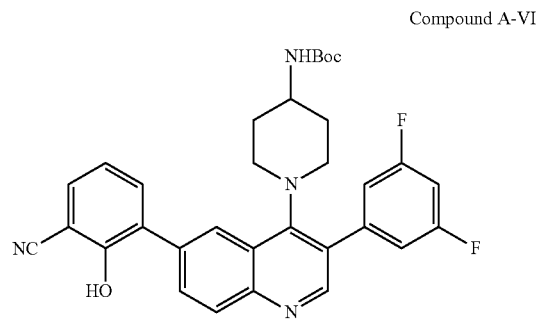 [SMILES: CC(C)(C)OC(=O)NC1CCN(c2c(-c3cc(F)cc(F)c3)cnc3ccc(-c4cccc(C#N)c4O)cc23)CC1]

with hydrochloric acid in a suitable solvent.

In another aspect, described herein is a process for the synthesis of 3-[4-(4-amino-piperidin-1-yl)-3-(3,5-difluoro-phenyl)-quinolin-6-yl]-2-hydroxy-benzonitrile monohydrochloride:

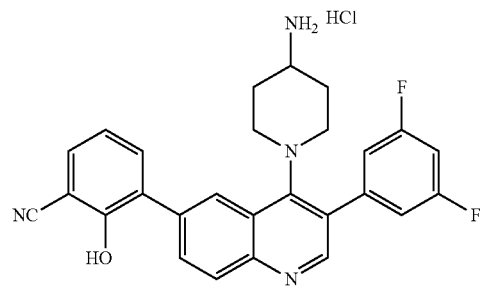 [SMILES: Cl ; N#Cc1cccc(-c2ccc3ncc(-c4cc(F)cc(F)c4)c(N4CCC(N)CC4)c3c2)c1O]

comprising the steps of:
(1) treating Compound A-VI:

Compound A-VI

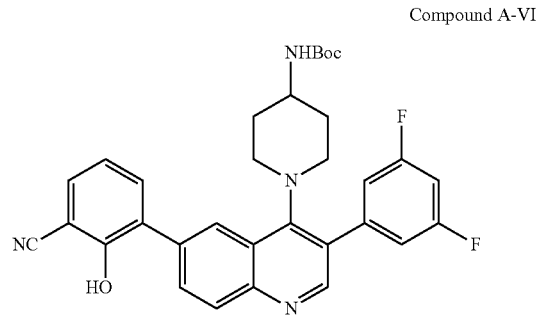 [SMILES: CC(C)(C)OC(=O)NC1CCN(c2c(-c3cc(F)cc(F)c3)cnc3ccc(-c4cccc(C#N)c4O)cc23)CC1]

with hydrochloric acid in a suitable solvent to provide 3-[4-(4-amino-piperidin-1-yl)-3-(3,5-difluoro-phenyl)-quinolin-6-yl]-2-hydroxy-benzonitrile dihydrochloride; and (2) treating 3-[4-(4-amino-piperidin-1-yl)-3-(3,5-difluoro-phenyl)-quinolin-6-yl]-2-hydroxy-benzonitrile dihydrochloride with aqueous ammonia to provide 3-[4-(4-amino-piperidin-1-yl)-3-(3,5-difluoro-phenyl)-quinolin-6-yl]-2-hydroxy-benzonitrile monohydrochloride.

In some embodiments, the suitable solvent is isopropyl alcohol, ethyl acetate, or isopropyl acetate. In some embodiments, the suitable solvent is isopropyl alcohol.

In another aspect, described herein is a process for the preparation of Compound A-VI:

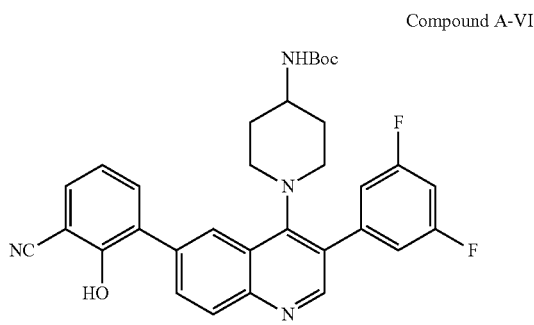 [SMILES: CC(C)(C)OC(=O)NC1CCN(c2c(-c3cc(F)cc(F)c3)cnc3ccc(-c4cccc(C#N)c4O)cc23)CC1]

Compound A-VI comprising the steps of:
(1) reacting Compound A-IV:

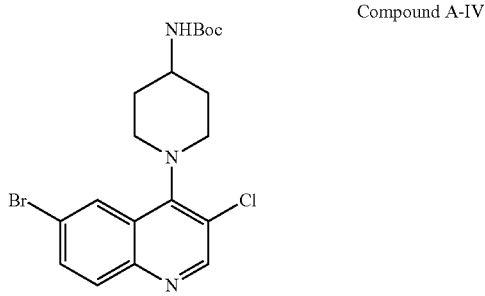 [SMILES: CC(C)(C)OC(=O)NC1CCN(c2c(Cl)cnc3ccc(Br)cc23)CC1]

Compound A-IV with Compound 1:

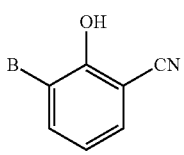

Compound 1 wherein,
B is a boronic acid, boronate ester, or trifluoroborate;
in the presence of a coupling catalyst, a suitable base, and in a suitable solvent, to provide Compound A-V:

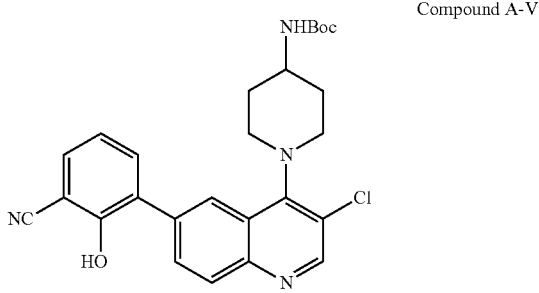 [SMILES: CC(C)(C)OC(=O)NC1CCN(c2c(Cl)cnc3ccc(-c4cccc(C#N)c4O)cc23)CC1]

Compound A-V and
(2) reacting Compound A-V with 3,5-difluorophenylboronic acid:

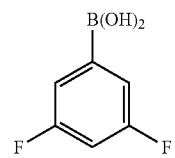

in the presence of a coupling catalyst, a suitable base, and in a suitable solvent, to provide Compound A-VI.

In some embodiments, B is a boronic acid or trifluoroborate.

In some embodiments, B is a boronic acid. In some embodiments, B is trifluoroborate.

In some embodiments, the coupling catalyst of step (1) is a palladium catalyst; the suitable base of step (1) is triethylamine, diisopropylethylamine, 1,2,2,6,6-pentamethylpiperidine, tributylamine, sodium bicarbonate, $Na_2CO_3$, $K_2CO_3$, $Cs_2CO_3$, NaOAc, KOAc, $Ba(OH)_2$, $Na_3PO_4$ or $K_3PO_4$; and the suitable solvent of step (1) is acetonitrile, dimethylformamide, ethanol, tetrahydrofuran, isopropyl alcohol, 1,4-dioxane, water, or combinations thereof. In some embodiments, Step (1) is performed at a temperature of about 80° C. In some embodiments, Step (1) is performed at a temperature of about 80-85° C.

In some embodiments, the coupling catalyst of step (1) is a palladium catalyst; the suitable base of step (1) is $K_2CO_3$; and the suitable solvent of step (1) is a mixture of 1,4-dioxane and water.

In some embodiments, the coupling catalyst of step (2) is a palladium catalyst; the suitable base of step (2) is triethylamine, diisopropylethylamine, 1,2,2,6,6-pentamethylpiperidine, tributylamine, sodium bicarbonate, $Na_2CO_3$, $K_2CO_3$, $Cs_2CO_3$, NaOAc, KOAc, $Ba(OH)_2$, $Na_3PO_4$ or $K_3PO_4$; and the suitable solvent of step (2) is acetonitrile, dimethylformamide, ethanol, tetrahydrofuran, isopropyl alcohol, 1,4-dioxane, water, or combinations thereof. In some embodiments, Step (2) is performed at a temperature of about 90° C. to about 100° C. In some embodiments, the coupling catalyst of step (2) is a palladium catalyst; the suitable base of step (2) is $K_2CO_3$; and the suitable solvent of step (2) is a mixture of 1,4-dioxane and water.

In some embodiments, Compound A-V is isolated prior to step (2).

In some embodiments, Compound A-V is not isolated prior to step (2).

In some embodiments, the process further comprises recrystallizing Compound A-VI from a suitable solvent. In some embodiments, the suitable solvent is methyl acetate, ethyl acetate, isopropyl acetate, methanol, ethanol, isopropyl alcohol, dichloromethane/petroleum ether, acetonitrile, tetrahydrofuran/water, tetrahydrofuran/petroleum ether, dimethylformamide/water, dichloromethane/methyl tert-butyl ether, methanol/methyl tert-butyl ether, methyl tert-butyl ether, or toluene. In some embodiments, the suitable solvent is ethyl acetate or isopropyl acetate.

In some embodiments, the process further comprises treatment of the recrystallized Compound A-VI with a metal scavenger. In some embodiments, the metal scavenger comprises $SiO_2$, charcoal, aqueous solution of L-cysteine, a Silicycle metal scavenger, Si-thiol, SiliaBond DMT or SiliaBond Cysteine.

In another aspect, described herein is a process for the preparation of Compound A-IV:

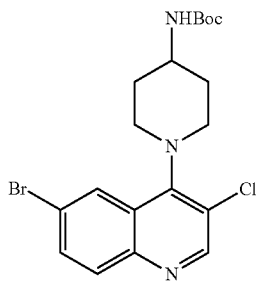

Compound A-IV

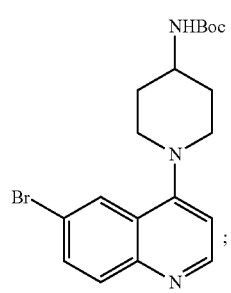

Compound 4 and (ii) chlorinating Compound 4 with a suitable chlorinating agent in a suitable solvent to provide Compound A-IV.

In some embodiments, the chlorinating agent of step (1) is N-chlorosuccinimide, trichloroisocyanuric acid, sulfuryl chloride, chlorine, sodium hypochlorite, calcium hypochlorite, hypochlorous acid, or 2,3,4,5,6,6-hexachloro-2,4-cyclohexadien-1-one; and the suitable solvent of step (1) is acetic acid, water, ethanol, methanol, toluene, dichloromethane, tetrahydrofuran, dioxane, or N,N-dimethylformamide.

In some embodiments, the chlorinating agent of step (1) is N-chlorosuccinimide; and the suitable solvent of step (1) is acetic acid.

In some embodiments, the brominating agent of step (2) is phosphorus tribromide, phosphorus oxybromide, hydrobromic acid, bromine, or dibromotriphenylphosphorane; and the suitable solvent of step (2) is acetonitrile, water, ethanol, isopropanol, dichloromethane, toluene, N,N-dimethylformamide, acetic acid, or acetone.

In some embodiments, the brominating agent of step (2) is phosphorus tribromide; and the suitable solvent of step (2) is N,N-dimethylformamide.

In some embodiments, the suitable base of step (3) is triethylamine, diisopropylethylamine, 1,8-diazabicycloundec-7-ene, 1,2,2,6,6-pentamethylpiperidine, tributylamine, sodium bicarbonate, $Na_2CO_3$, $K_2CO_3$, or $Cs_2CO_3$; and the suitable solvent of step (3) is N,N-dimethylformamide, N,N-dimethylacetamide, dimethylsulfoxide, dichlormethane, chloroform, carbon tetrachloride, dioxane, tetrahydrofuran, toluene, acetonitrile, ethanol, or isopropanol.

In some embodiments, the base of step (3) is diisopropylethylamine; and the suitable solvent of step (3) is dimethylsulfoxide.

In some embodiments, the suitable base of step (i) is triethylamine, diisopropylethylamine, 1,8-diazabicycloundec-7-ene, 1,2,2,6,6-pentamethylpiperidine, tributylamine, sodium bicarbonate, $Na_2CO_3$, $K_2CO_3$, or $Cs_2CO_3$; and the suitable solvent of step (i) is N,N-dimethylformamide, N,N-dimethylacetamide, dimethylsulfoxide, dichlormethane, chloroform, carbon tetrachloride, dioxane, tetrahydrofuran, toluene, acetonitrile, ethanol, or isopropanol.

In some embodiments, the base of step (i) is $K_2CO_3$; and the suitable solvent of step (i) is N,N-dimethylformamide.

In some embodiments, the chlorinating agent of step (ii) is N-chlorosuccinimide, trichloroisocyanuric acid, sulfuryl chloride, chlorine, sodium hypochlorite, calcium hypochlorite, hypochlorous acid, or 2,3,4,5,6,6-hexachloro-2,4-cyclohexadien-1-one; and the suitable solvent of step (ii) is acetic acid, water, ethanol, methanol, toluene, dichloromethane, tetrahydrofuran, dioxane, or N,N-dimethylformamide.

In some embodiments, the chlorinating agent of step (ii) is N-chlorosuccinimide; and the suitable solvent of step (ii) is toluene.

comprising the steps of:

(1) chlorinating Compound A-I:

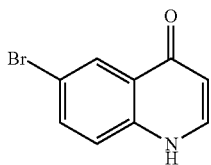

Compound A-I with a suitable chlorinating agent in a suitable solvent to provide Compound A-II:

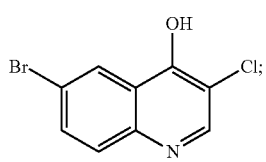

Compound A-II (2) brominating Compound A-II with a suitable brominating agent in a suitable solvent to provide Compound A-III:

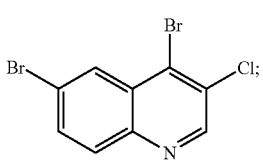

Compound A-III and (3) coupling 4-(N-Boc amino)piperidine with Compound A-III in the presence of a suitable base and in a suitable solvent to provide Compound A-IV;

or (i) coupling 4-(N-Boc amino)piperidine with 6-bromo-4-chloro-quinoline in the presence of a suitable base and in a suitable solvent to provide Compound 4:

In another aspect, described herein is a process for the preparation of Compound 1:

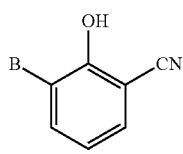

Compound 1 wherein,
B is a boronic acid or boronate ester;
comprising the steps of:
(1) protecting the hydroxyl group of Compound 2:

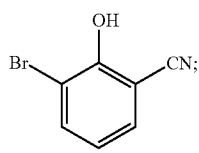

Compound 2 with a suitable protecting group (PG') to provide Compound 2a:

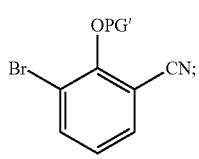

Compound 2a (2) reacting Compound 2a with a borylation agent under suitable reaction conditions; and
(3) removal of the protecting group (PG') to provide Compound 1.

In some embodiments, B is a boronic acid.

In some embodiments, the process further comprises converting B to a trifluoroborate.

In some embodiments, the borylation agent is triisopropyl borate, trimethyl borate, tetrahydroxydiboron, pinacolborane, catecholborane, bis(neopentyl glycolato)diboron, bis(pinacolato)diboron, bis(hexylene glycolato)diboron, bis(catecholato)diboron, 4,4,5,5-tetramethyl-1,3,2-dioxaborolane, 4,6,6-trimethyl-1,3,2-dioxaborinane, diisopropylamine borane, bis(neopentyl glycolato)diboron, bis(catecholato)diboron, or bis(pinacolato)diboron.

In some embodiments, the suitable reaction conditions of (2) comprise the use of metal halogen exchange reagents. In some embodiments, the suitable reaction conditions of (2) comprise the use of metal halogen exchange reagents selected from Grignard reagents and alkyl lithium reagents. In some embodiments, the suitable reaction conditions of (2) comprise the use of isopropyl magnesium chloride in tetrahydrofuran.

In some embodiments, the borylation agent is triisopropyl borate and the suitable reaction conditions of (2) comprise the use of isopropyl magnesium chloride in tetrahydrofuran.

In some embodiments, the suitable reaction conditions of (2) comprise the use of transition metal mediated reaction conditions.

In some embodiments, the suitable reaction conditions of (2) comprise the use of palladium metal mediated reaction conditions.

In some embodiments, the suitable protecting group (PG') is methoxymethyl, ethoxyethyl, methoxypropyl, benzyloxymethyl, 2-methoxyethoxymethyl, benzyl, para-methoxybenzyl, 2-naphthylmethyl, methyl, allyl, tetrahydropyranyl, acetyl, benzoyl, 2,2,2-trichloroethyl carbonyl, trimethylsilyl, triethylsilyl, triisopropyl silyl, tert-butyldimethylsilyl, or tert-butyldiphenylsilyl.

In some embodiments, the suitable protecting group (PG') is methoxymethyl, 2-methoxyethoxymethyl, benzyl, para-methoxybenzyl, methyl, allyl, tetrahydropyran-2-yl, [2-(trimethylsilyl)ethoxy]methyl, trimethylsilyl, triethylsilyl, triisopropyl silyl, tert-butyldimethylsilyl, or tert-butyldiphenylsilyl.

In some embodiments, the suitable protecting group (PG') is methoxymethyl, ethoxyethyl, methoxypropyl, benzyloxymethyl, 2-methoxyethoxymethyl, benzyl, para-methoxybenzyl, 2-naphthylmethyl, methyl, allyl, or tetrahydropyranyl. In some embodiments, the suitable protecting group (PG') is methoxymethyl, ethoxyethyl, or 2-methoxyethoxymethyl. In some embodiments, the suitable protecting group (PG') is methoxymethyl.

In some embodiments, the suitable protecting group (PG') is acetyl, benzoyl, or 2,2,2-trichloroethyl carbonyl. In some embodiments, the suitable protecting group (PG') is acetyl.

In some embodiments, removal of the protecting group in step (3) is accomplished by treatment with hydrochloric acid, hydrobromic acid, acetic acid, trifluoroacetic acid, para-toluenesulfonic acid, $ZnBr_2$, hydrogen over Pd/C, 2,3-dichloro-5,6-dicyano-1,4-benzoquinone (DDQ), boron tribromide, boron trichloride, trimethylsilyl iodide, $Pd(PPh_3)_4$, tetra-n-butylammonium fluoride (TBAF), or HF-pyridine.

In some embodiments, the suitable protecting group (PG') is methoxymethyl; and removal of the protecting group in step (3) is accomplished by treatment with hydrochloric acid.

Articles of manufacture, which include packaging material, a somatostatin modulator, or a pharmaceutically acceptable salt or solvate thereof, as described herein, within the packaging material, and a label that indicates that the somatostatin modulator, or pharmaceutically acceptable salt, or solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

BRIEF DESCRIPTION OF THE DRAWINGS

FIG. 7(a). X-ray powder diffraction (XRPD) pattern A of Compound A, free base.

DETAILED DESCRIPTION OF THE INVENTION

Figure 1:
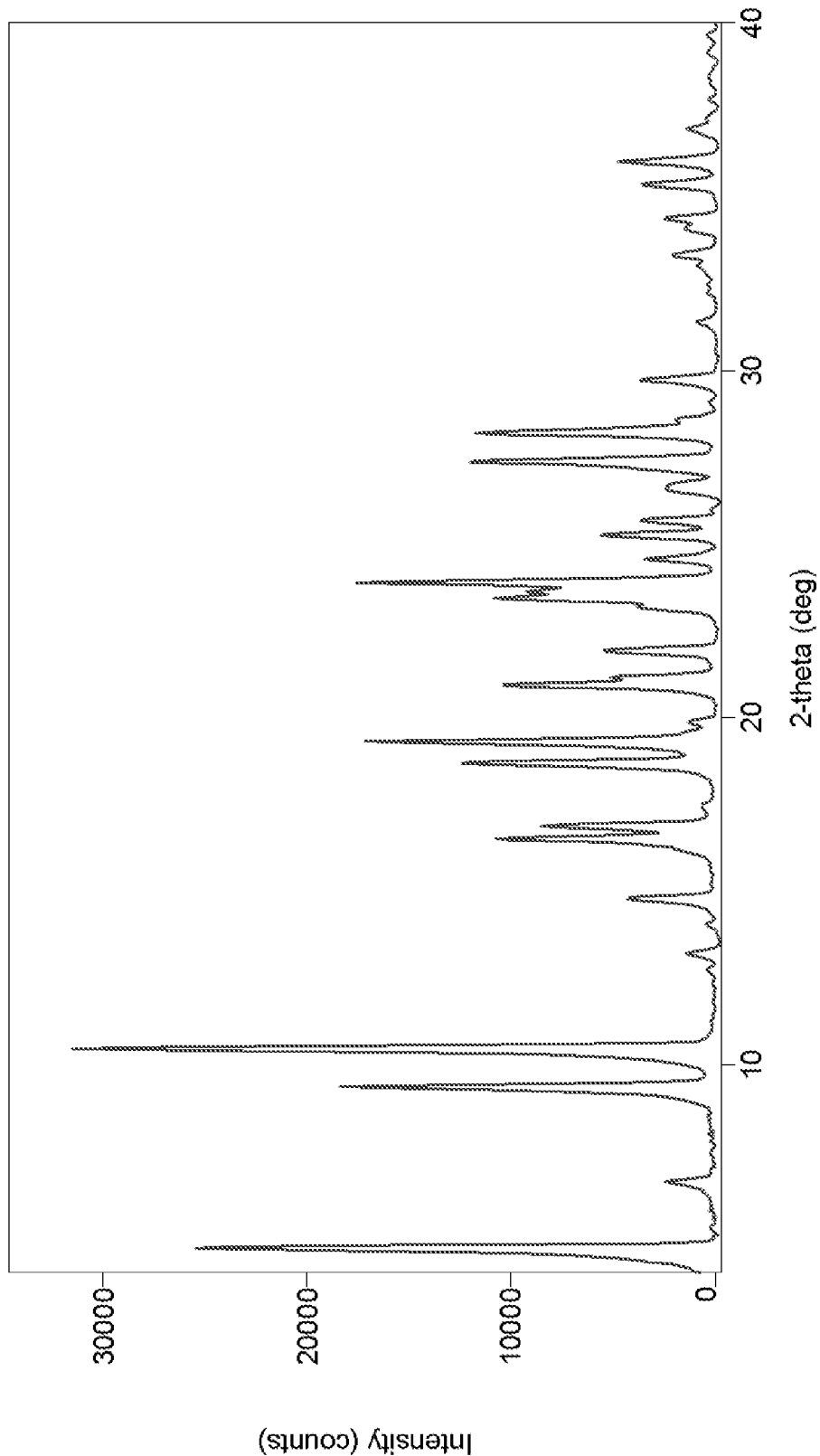
FIG. 1. X-ray powder diffraction (XRPD) pattern of Compound A, mono-HCl salt.

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut, and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends EndocrinolMetab* 8, 398-405, 1997). All the receptors are members of the class-A subgroup of the GPCR superfamily. SST2A receptor is the most widely expressed subtype in human tumors and is the dominant receptor by which GH secretion is suppressed. Unless otherwise stated, the term SSTR2 means SSTR2a.

It is possible to selectively modulate any one of the somatostatin receptor subtypes, or combination thereof. In some embodiments, selectively modulating any one of the somatostatin receptor subtypes relative to the other somatostatin receptor subtypes, or combination thereof, is useful in a variety of clinical applications. In some embodiments, selectively modulating any one of the somatostatin receptor subtypes relative to the other somatostatin receptor subtypes reduces unwanted side effects in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR4 agonists exhibit anti-inflammatory and anti-nociceptive effects.

In some embodiments, SSTR3 agonists inhibit insulin secretion.

In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cerebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminished in the hippocampi of Alzheimer's and Parkinson's patients, suggesting that restoration of its signaling as a potential drug target for neurodegeneration.

In one aspect, compounds described herein are modulators of SSTR2. In some embodiments, compounds described herein selectively modulate the activity of SSTR2 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VIPomas, insulinomas and glucagonomas; or diabetes and diabetes-related pathologies, including retinopathy, neuropathy and nephropathy. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

Compound A is a somatostatin modulator that is useful in the methods of treatment described herein.

Compound A

As used herein, Compound A refers to 3-(4-(4-aminopiperidin-1-yl)-3-(3,5-difluoro-phenyl)-quinolin-6-yl)-2-hydroxy-benzonitrile, which has the chemical structure shown below.

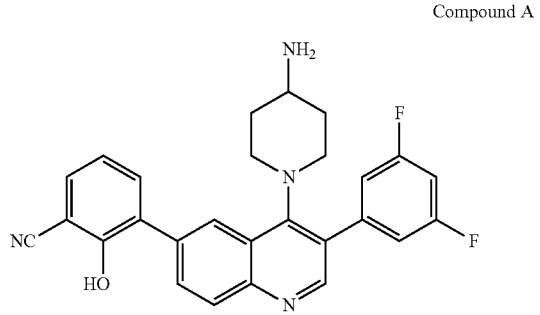 [SMILES: N#Cc1cccc(-c2ccc3ncc(-c4cc(F)cc(F)c4)c(N4CCC(N)CC4)c3c2)c1O]

Compound A

In some embodiments, Compound A is amorphous.
In some embodiments, Compound A is crystalline.
In some embodiments, Compound A is crystalline and has an X-Ray powder diffraction pattern with peaks at 9.2° 2-Theta, 12.3° 2-Theta, 14.4° 2-Theta, and 24.0° 2-Theta. In some embodiments, Compound A is crystalline and has an X-Ray powder diffraction pattern substantially similar to the XRPD displayed in FIG. 7(a).

In some embodiments, Compound A is crystalline and has an X-Ray powder diffraction pattern with peaks at 5.9° 2-Theta, 13.9° 2-Theta, 14.2° 2-Theta, 17.5° 2-Theta, and 24.6° 2-Theta. In some embodiments, Compound A is crystalline and has an X-Ray powder diffraction pattern substantially similar to the XRPD displayed in FIG. 7(b).

Figure 7B:
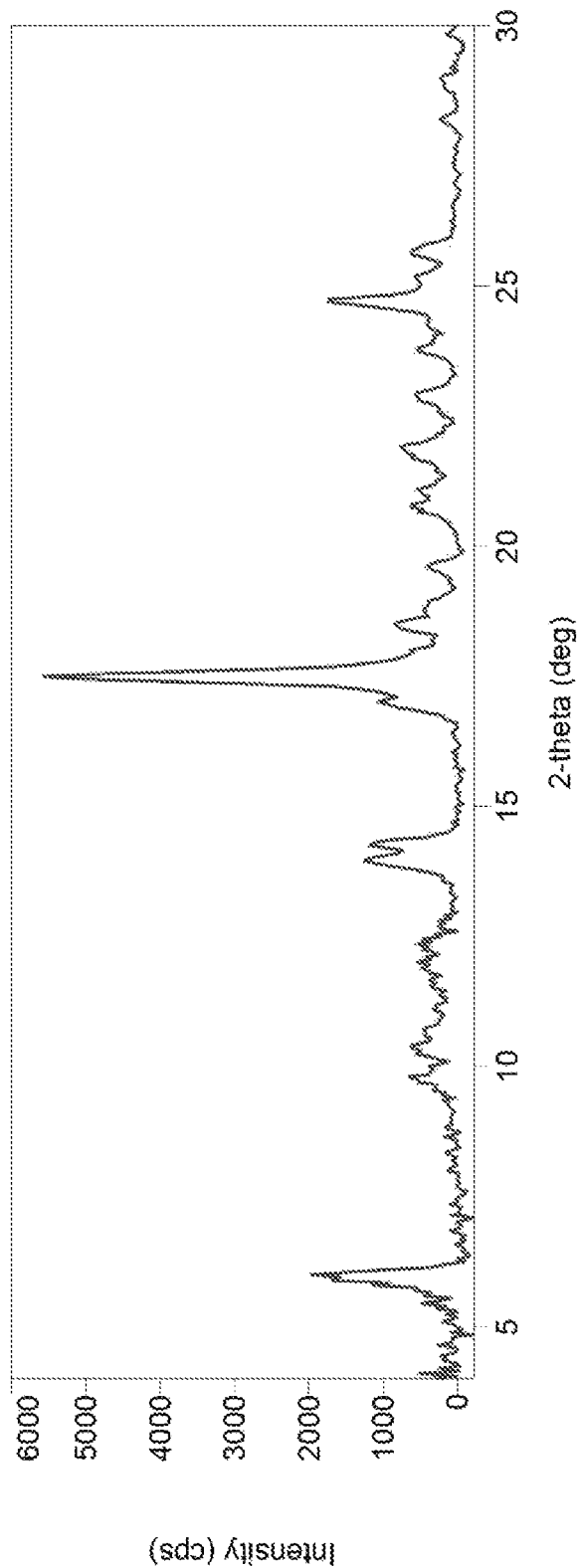
FIG. 7(b). X-ray powder diffraction (XRPD) pattern B of Compound A, free base.
Figure 7C:
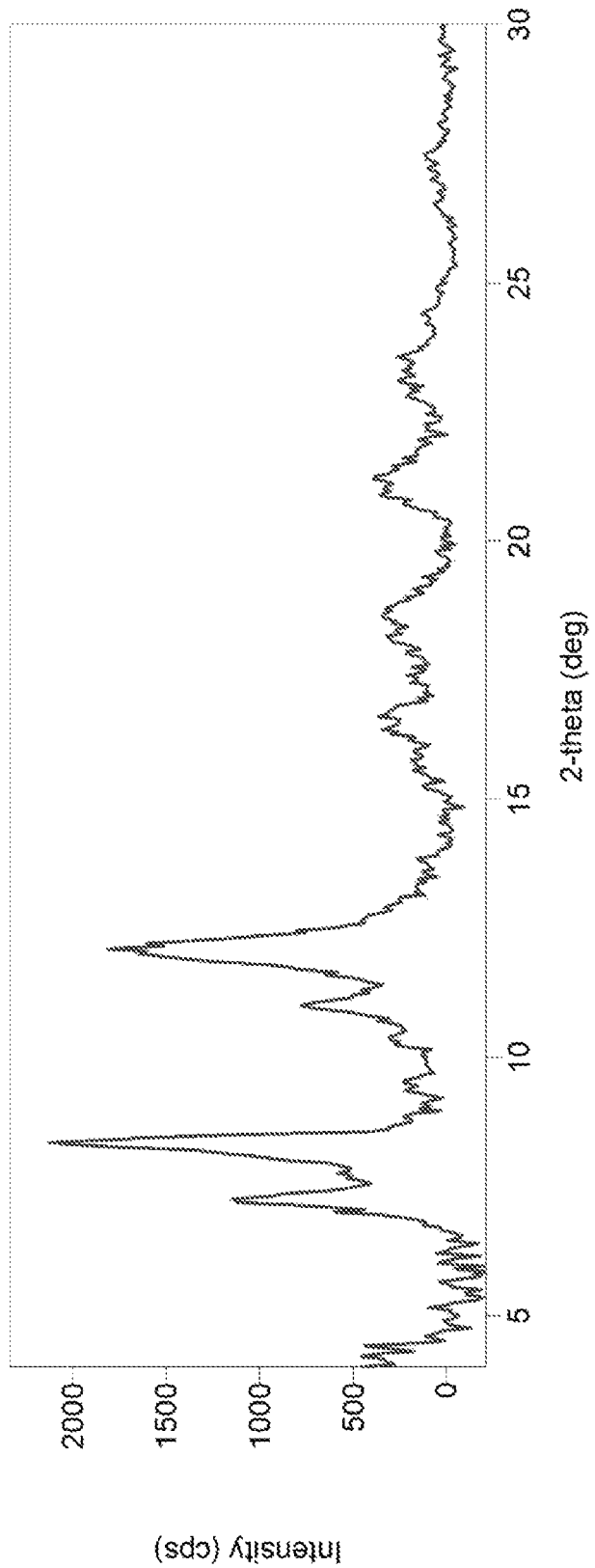
FIG. 7(c). X-ray powder diffraction (XRPD) pattern C of Compound A, free base.
Figure 8A:
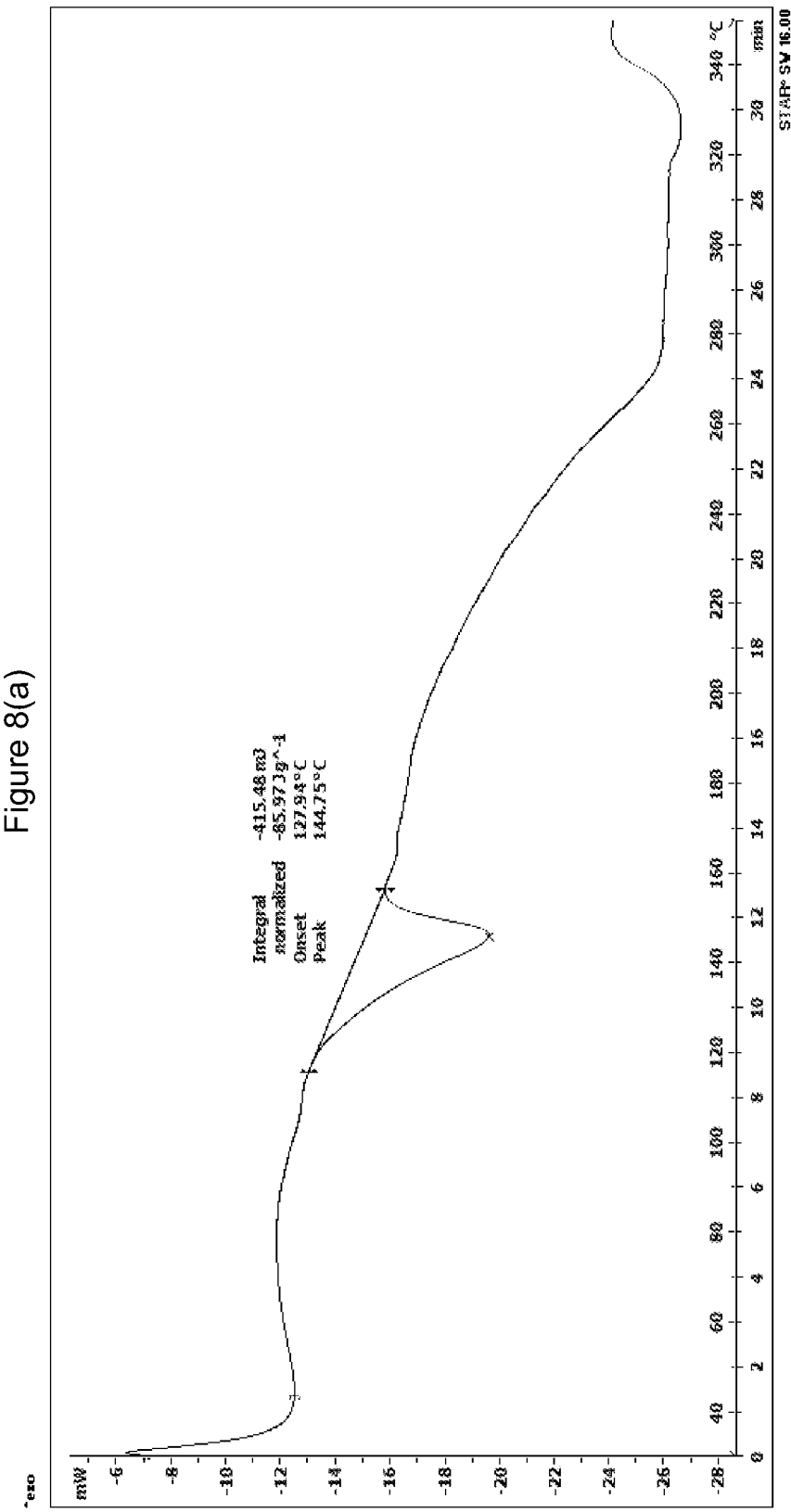
FIG. 8(a). Differential Scanning Calorimetry (DSC) thermogram of Pattern C of Compound A, free base.
Figure 8B:
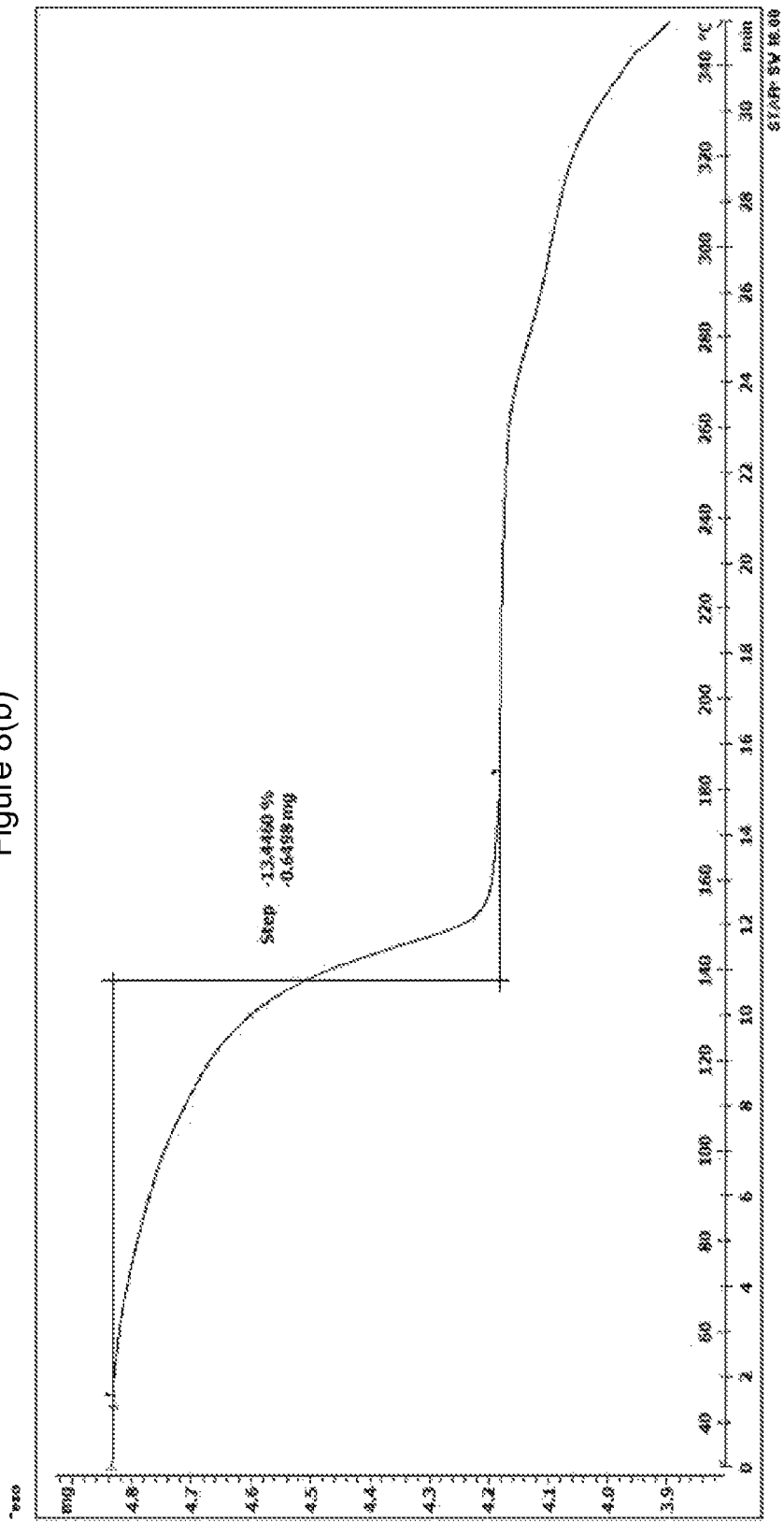
FIG. 8(b). Thermogravimetric Analysis (TGA) thermogram of Pattern C of Compound A, free base.

In some embodiments, Compound A is crystalline and is characterized as having: an X-ray powder diffraction (XRPD) pattern with peaks at 7.2° 2-Theta, 8.3° 2-Theta, 10.9° 2-Theta, and 12.0° 2-Theta; an X-ray powder diffraction (XRPD) pattern substantially the same as shown in FIG. 7(c); a Differential Scanning Calorimetry (DSC) thermogram with an endotherm having an onset at about 128° C. and a peak at about 145° C.; a Differential Scanning Calorimetry (DSC) thermogram substantially the same as shown in FIG. 8(a); a Differential Scanning Calorimetry (DSC) thermogram substantially the same as shown in FIG. 8(a); a Thermogravimetric Analysis (TGA) thermogram substantially the same as shown in FIG. 8(b); or combinations thereof.

In some embodiments, Compound A is crystalline and is characterized as having at least one of the following properties:

a) an X-ray powder diffraction (XRPD) pattern with peaks at 7.2° 2-Theta, 8.3° 2-Theta, 10.9° 2-Theta, and 12.0° 2-Theta;

b) an X-ray powder diffraction (XRPD) pattern substantially the same as shown in FIG. 7(c);

c) a Differential Scanning Calorimetry (DSC) thermogram with an endotherm having an onset at about 128° C. and a peak at about 145° C.;

d) a Differential Scanning Calorimetry (DSC) thermogram substantially the same as shown in FIG. 8(a).

In some embodiments, Compound A is crystalline and is characterized as having at least two of the properties selected from a) to d). In some embodiments, Compound A is crystalline and is characterized as having at least three of the properties selected from a) to d). In some embodiments, Compound A is crystalline and is characterized as having properties a), b), c), and d).

In some embodiments, Compound A is crystalline and has an X-ray powder diffraction (XRPD) pattern with peaks at 7.2° 2-Theta, 8.3° 2-Theta, 10.9° 2-Theta, and 12.0° 2-Theta. In some embodiments, Compound A is crystalline and has an X-ray powder diffraction (XRPD) pattern substantially the same as shown in FIG. 7(c). In some embodiments, Compound A is crystalline and has a Differential Scanning Calorimetry (DSC) thermogram with an endotherm having an onset at about 128° C. and a peak at about 145° C. In some embodiments, Compound A is crystalline and has a Differential Scanning Calorimetry (DSC) thermogram substantially the same as shown in FIG. 8(a).

In some embodiments, provided herein is a pharmaceutically acceptable salt of Compound A. In some embodiments, the pharmaceutically acceptable salt of Compound A is the monohydrochloride salt (Compound A-HCl):

Compound A-HCl

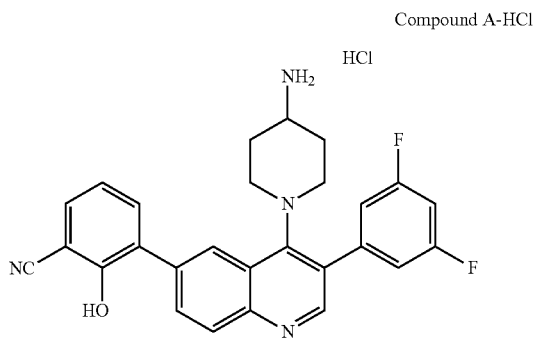 [SMILES: Cl ; N#Cc1cccc(-c2ccc3ncc(-c4cc(F)cc(F)c4)c(N4CCC(N)CC4)c3c2)c1O]

In some embodiments, Compound A-HCl is amorphous.

In some embodiments, Compound A-HCl is crystalline.

Figure 2A:
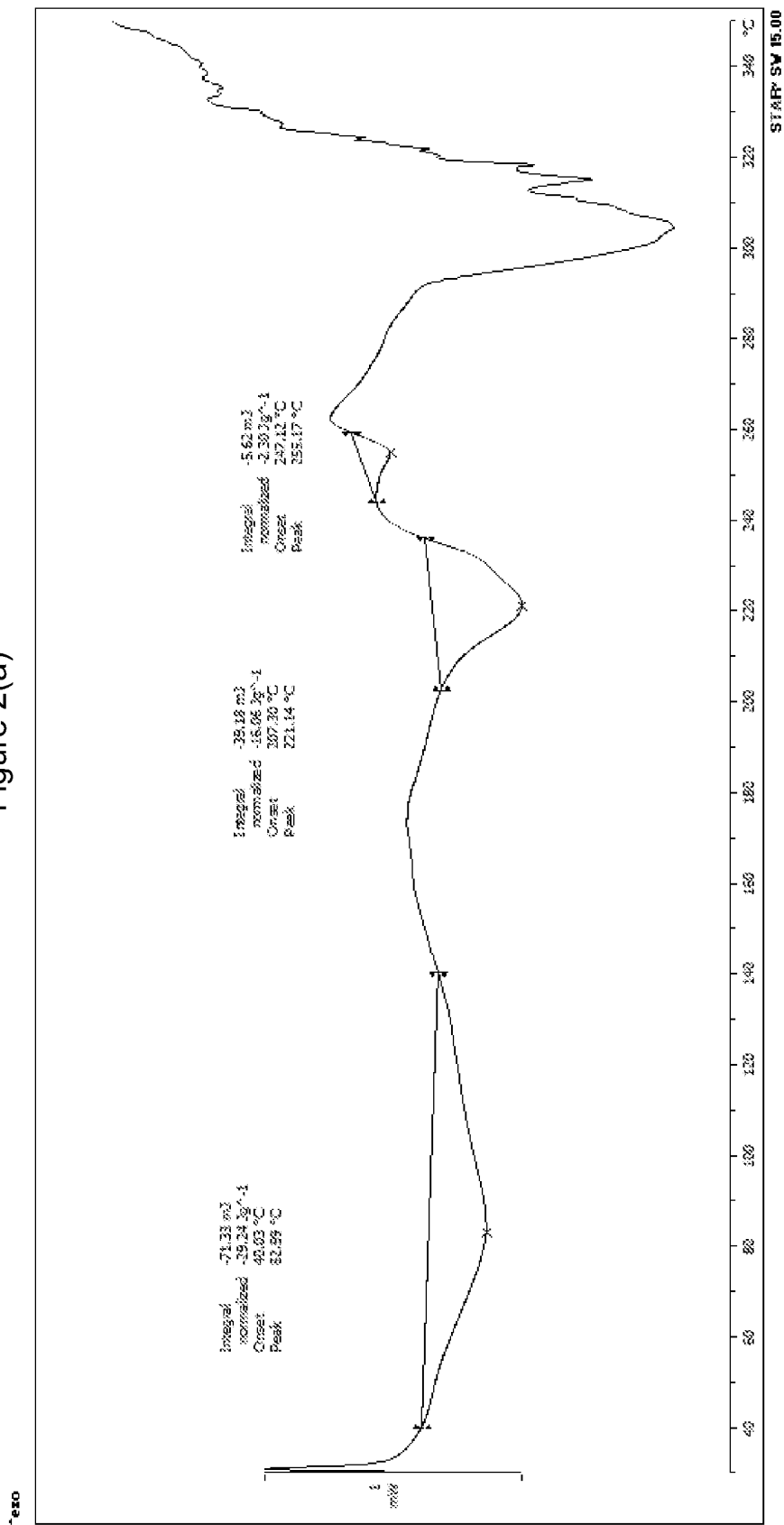
FIG. 2(a). Differential Scanning Calorimetry (DSC) thermogram.
Figure 2B:
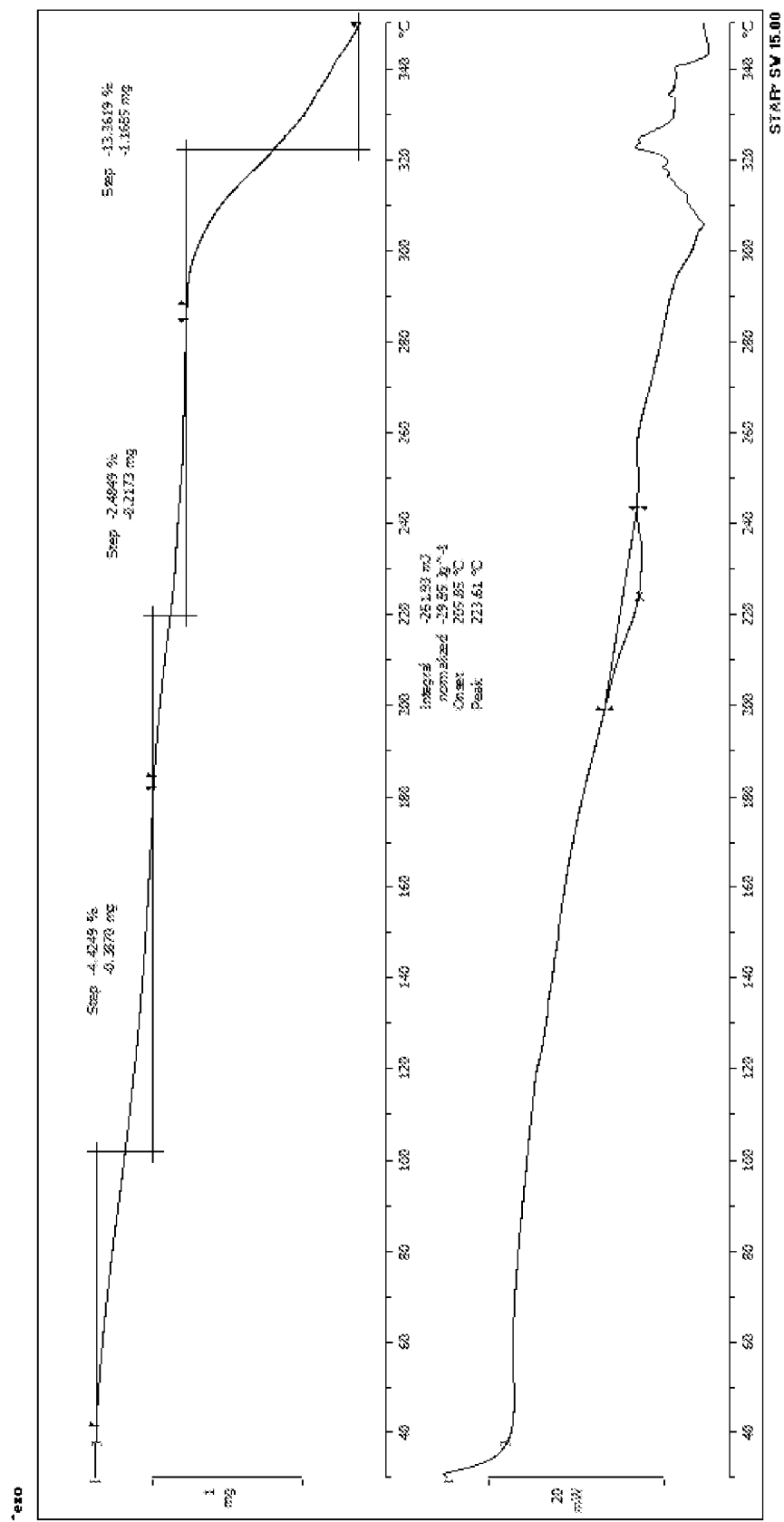
FIG. 2(b). Thermogravimetric Analysis/Differential Scanning Calorimetry (TGA/DSC) thermogram of Compound A, mono-HCl salt.
Figure 3:
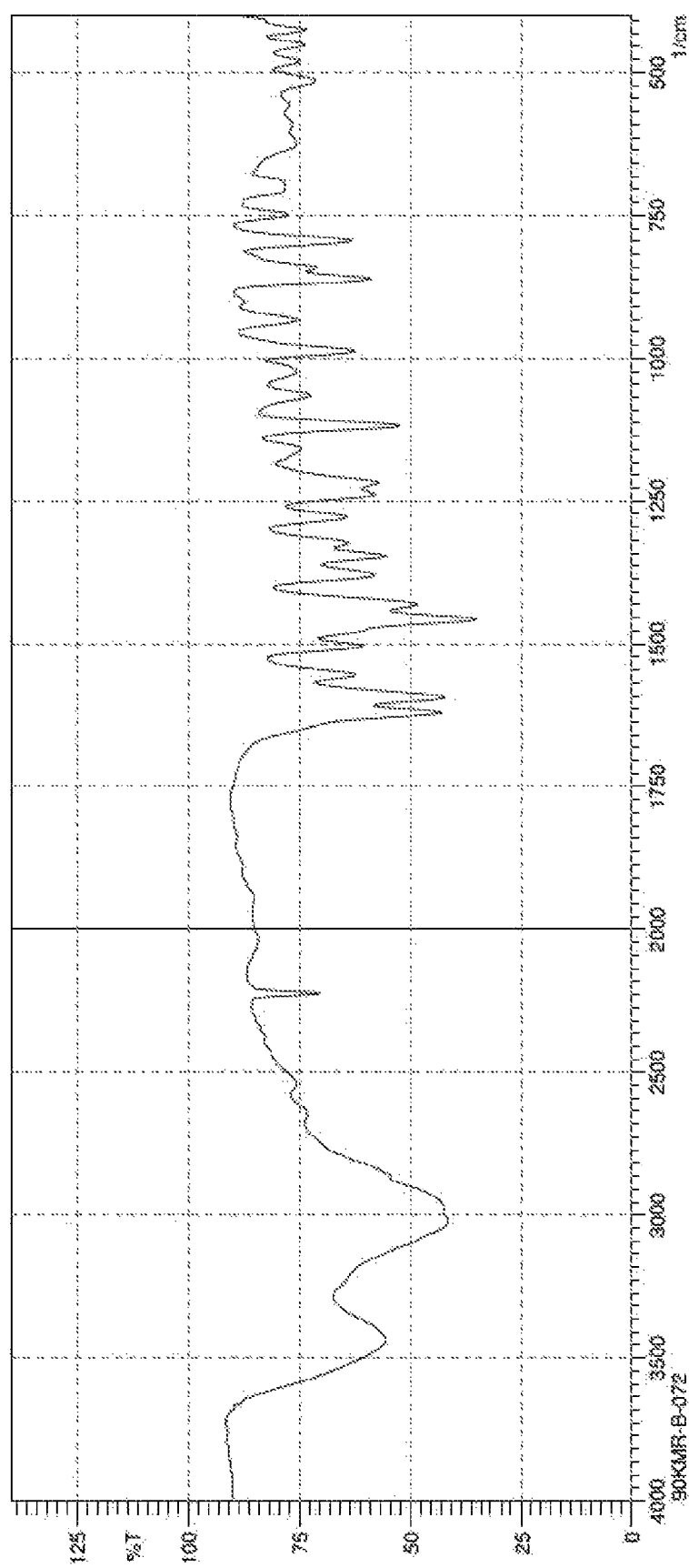
FIG. 3. Infrared (IR) spectrum of Compound A, mono-HCl salt.

In some embodiments, Compound A-HCl is crystalline and is characterized as having: an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta; an X-ray powder diffraction (XRPD) pattern substantially the same as shown in FIG. 1; a Differential Scanning Calorimetry (DSC) thermogram with an endotherm having an onset at about 207° C. and a peak at about 220° C.; a Differential Scanning Calorimetry (DSC) thermogram substantially the same as shown in FIG. 2(a); a Thermogravimetric Analysis (TGA) thermogram substantially the same as shown in FIG. 2(b); an infrared (IR) spectrum with peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$; an infrared (IR) spectrum substantially the same as shown in FIG. 3; an unchanged XRPD when heated up to about 200° C., upon exposure to more than 90% relative humidity for about 24 hours, or upon exposure to about 75% RH and 40° C. over one week, or combinations thereof, or combinations thereof.

In some embodiments, Compound A-HCl is crystalline and is characterized as having at least one of the following properties:
a) an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta;
b) an X-ray powder diffraction (XRPD) pattern substantially the same as shown in FIG. 1;
c) a Differential Scanning Calorimetry (DSC) thermogram with an endotherm having an onset at about 207° C. and a peak at about 220° C.;
d) a Differential Scanning Calorimetry (DSC) thermogram substantially the same as shown in FIG. 2(a);
e) an infrared (IR) spectrum with characteristic peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$;
f) an infrared (IR) spectrum substantially the same as shown in FIG. 3;
g) reversible water uptake (~4.5% w/w) between 2 and 95% Relative Humidity (RH);
h) reversible water uptake (~2.3%) between 15 and 75% Relative Humidity (RH);
i) an unchanged XRPD after DVS analysis at 90% RH and room temperature over 24 hours; or
j) an unchanged XRPD after the DVS analysis at 75% RH and 40° C. over one week.

In some embodiments, Compound A-HCl is crystalline and is characterized as having at least two of the properties selected from a) to j). In some embodiments, Compound A-HCl is crystalline and is characterized as having at least three of the properties selected from a) to j). In some embodiments, Compound A-HCl is crystalline and is characterized as having at least four of the properties selected from a) to j). In some embodiments, Compound A-HCl is crystalline and is characterized as having at least five of the properties selected from a) to j). In some embodiments, Compound A-HCl is crystalline and is characterized as having at least six of the properties selected from a) to j). In some embodiments, Compound A-HCl is crystalline and is characterized as having at least seven of the properties selected from a) to j). In some embodiments, Compound A-HCl is crystalline and is characterized as having at least eight of the properties selected from a) to j). In some embodiments, Compound A-HCl is crystalline and is characterized as having at least nine of the properties selected from a) to j). In some embodiments, Compound A-HCl is crystalline and is characterized as having properties a), b), c), d), e), f), g), h), i), and j).

In some embodiments, Compound A-HCl is crystalline and has an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta. In some embodiments, Compound A-HCl is crystalline and has an X-ray powder diffraction (XRPD) pattern substantially the same as shown in FIG. 1. In some embodiments, Compound A-HCl is crystalline and has a Differential Scanning Calorimetry (DSC) thermogram with an endotherm having an onset at about 207° C. and a peak at about 220° C. In some embodiments, Compound A-HCl is crystalline and has a Differential Scanning Calorimetry (DSC) thermogram substantially the same as shown in FIG. 2(a). In some embodiments, Compound A-HCl is crystalline and has an infrared (IR) spectrum with characteristic peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$. In some embodiments, Compound A-HCl is crystalline and has an infrared (IR) spectrum substantially the same as shown in FIG. 3. In some embodiments, Compound A-HCl is crystalline and has reversible water uptake (~4.5% w/w) between 2 and 95% Relative Humidity (RH). In some embodiments, Compound A-HCl is crystalline and has reversible water uptake (~2.3%) between 15 and 75% Relative Humidity (RH). In some embodiments, Compound A-HCl is crystalline and has an unchanged XRPD after DVS analysis at 90% RH and room temperature over 24 hours. In some embodiments, Compound A-HCl is crystalline and has an unchanged XRPD after the DVS analysis at 75% RH and 40° C. over one week.

In some embodiments, provided herein is a pharmaceutically acceptable salt of Compound A. In some embodiments, the pharmaceutically acceptable salt of Compound A is the dihydrochloride salt (Compound A-2HCl):

Compound A-2HCl

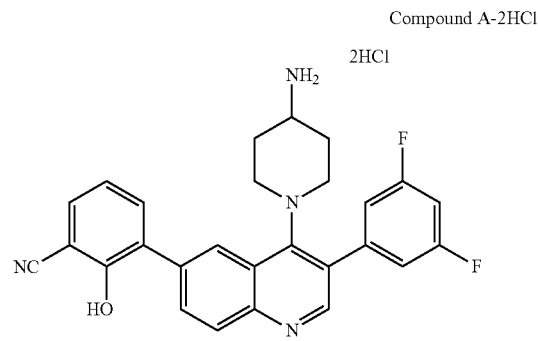 [SMILES: "2HCl" ; N#Cc1cccc(-c2ccc3ncc(-c4cc(F)cc(F)c4)c(N4CCC(N)CC4)c3c2)c1O]

In some embodiments, Compound A-2HCl is amorphous.

In some embodiments, Compound A-2HCl is crystalline.

Figure 4:
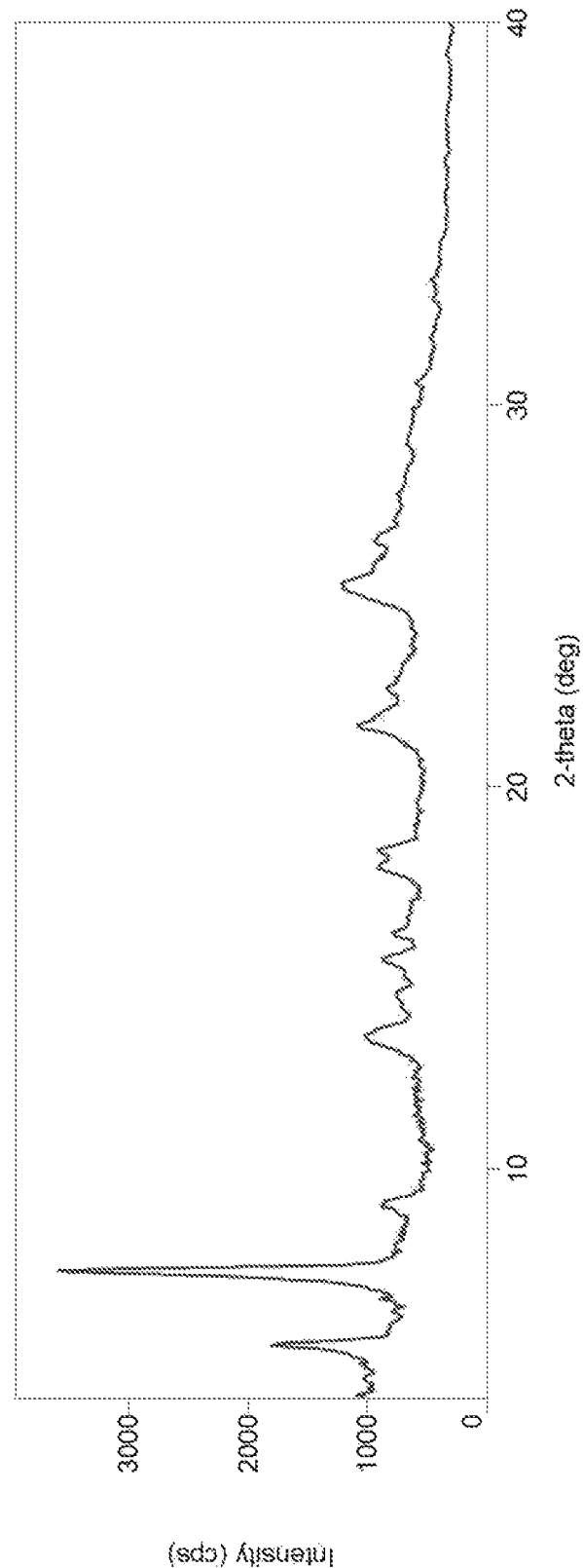
FIG. 4. X-ray powder diffraction (XRPD) pattern of Compound A, di-HCl salt.
Figure 5A:
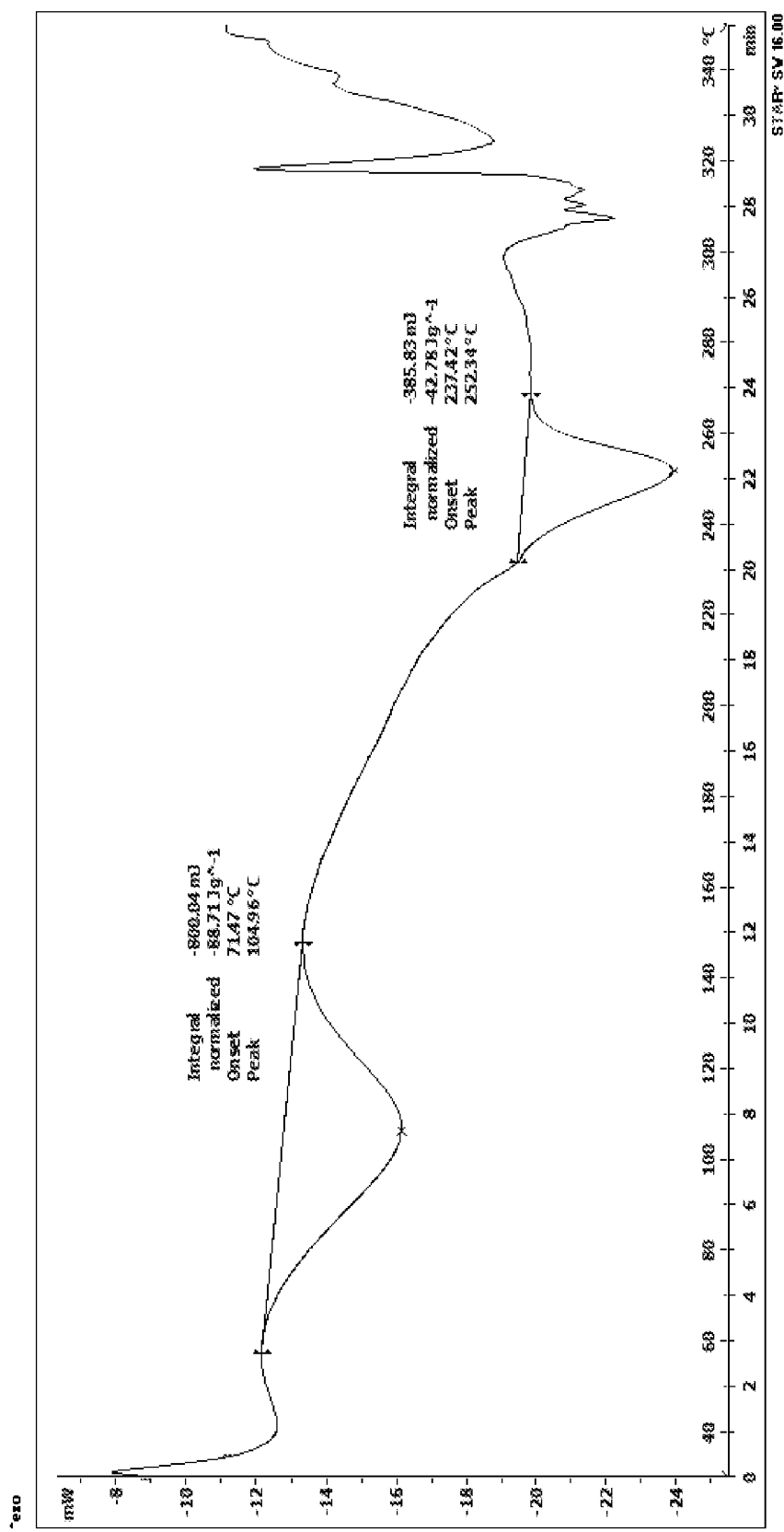
FIG. 5(a). Differential Scanning Calorimetry (DSC) thermogram of Compound A, di-HCl salt.
Figure 5B:
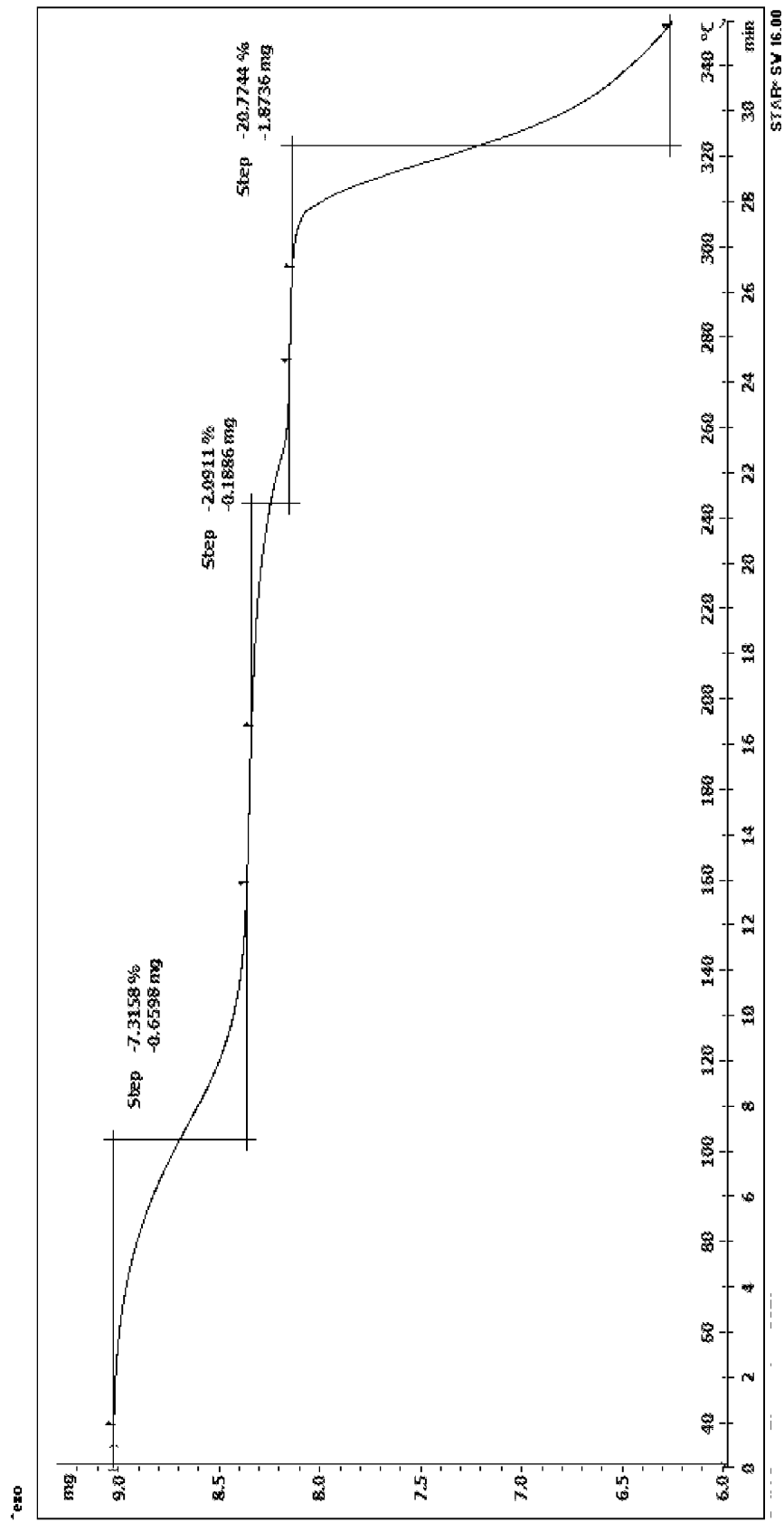
FIG. 5(b). Thermogravimetric Analysis (TGA) thermogram of Compound A, di-HCl salt.
Figure 6:
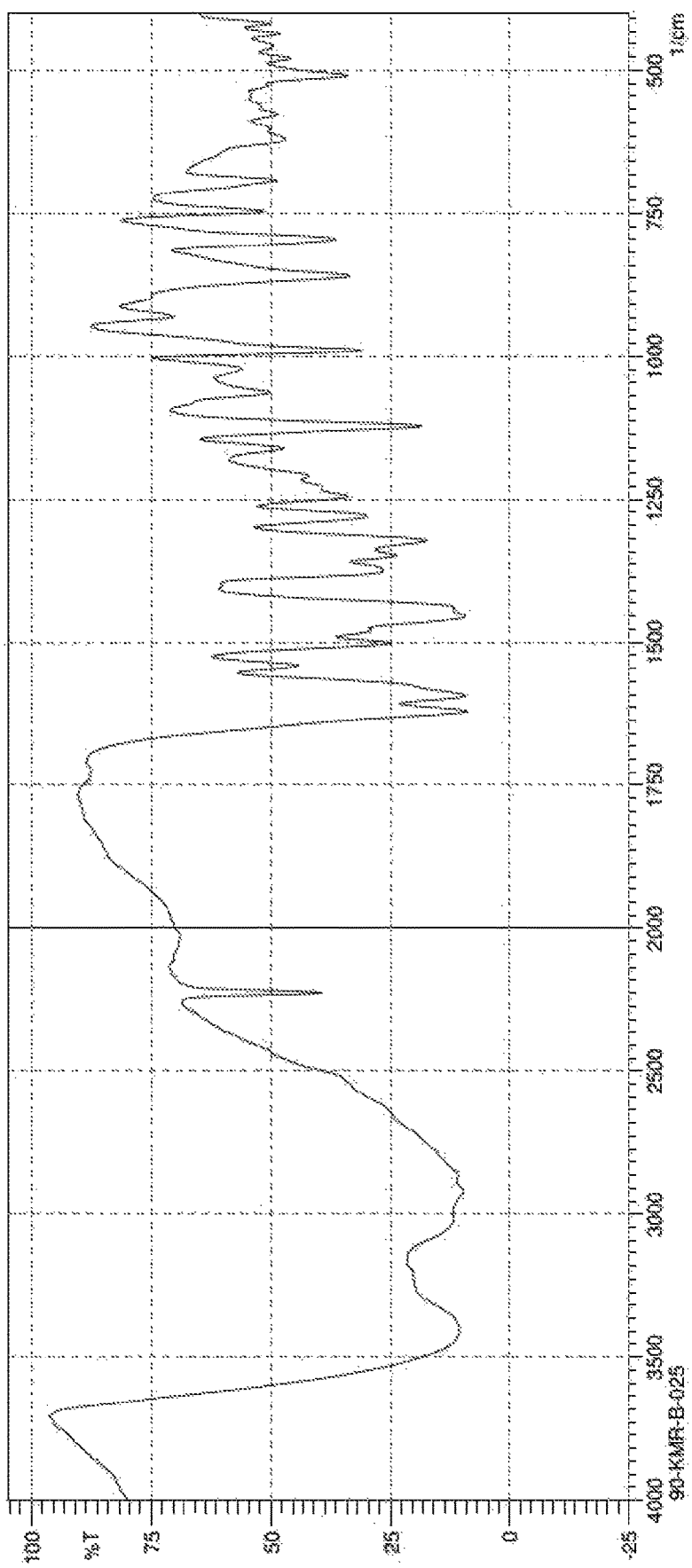
FIG. 6. Infrared (IR) spectrum of Compound A, di-HCl salt.

In some embodiments, Compound A-2HCl is crystalline and is characterized as having: an X-ray powder diffraction (XRPD) pattern with peaks at 5.4° 2-Theta, and 7.3° 2-Theta; an X-ray powder diffraction (XRPD) pattern substantially the same as shown in FIG. 4; a Differential Scanning Calorimetry (DSC) thermogram with an endotherm having an onset at about 233° C. and a peak at about 252° C.; a Differential Scanning Calorimetry (DSC) thermogram substantially the same as shown in FIG. 5(a); a Thermogravimetric Analysis (TGA) thermogram substantially the same as shown in FIG. 5(b); an infrared (IR) spectrum with characteristic peaks at 2227 cm$^{-1}$, 1620 cm$^{-1}$, 1594 cm$^{-1}$, 1456 cm$^{-1}$, 1439 cm$^{-1}$, 1321 cm$^{-1}$, and 1122 cm$^{-1}$; an infrared (IR) spectrum substantially the same as shown in FIG. 6; reversible water uptake (~18% w/w) between 2 and 95% Relative Humidity (RH); reversible water uptake (~9% w/w) between 2 and 95% Relative Humidity (RH); an unchanged XRPD after DVS analysis at 90% RH and room temperature over 24 hours; an unchanged XRPD after the DVS analysis at 75% RH and 40° C. over one week; or combinations thereof.

In some embodiments, Compound A-2HCl is crystalline and has at least one of the following properties:
a) an X-ray powder diffraction (XRPD) pattern with peaks at 5.4° 2-Theta, and 7.3° 2-Theta;
b) an X-ray powder diffraction (XRPD) pattern substantially the same as shown in FIG. 4;
c) a Differential Scanning Calorimetry (DSC) thermogram with an endotherm having an onset at about 233° C. and a peak at about 252° C.;
d) a Differential Scanning Calorimetry (DSC) thermogram substantially the same as shown in FIG. 5(a);
e) an infrared (IR) spectrum with characteristic peaks at 2227 cm$^{-1}$, 1620 cm$^{-1}$, 1594 cm$^{-1}$, 1456 cm$^{-1}$, 1439 cm$^{-1}$, 1321 cm$^{-1}$, and 1122 cm$^{-1}$;
f) an infrared (IR) spectrum substantially the same as shown in FIG. 6;
g) reversible water uptake (~18% w/w) between 2 and 95% Relative Humidity (RH);
h) reversible water uptake (~9% w/w) between 2 and 95% Relative Humidity (RH);
i) an unchanged XRPD after DVS analysis at 90% RH and room temperature over 24 hours; or
j) an unchanged XRPD after the DVS analysis at 75% RH and 40° C. over one week.

In some embodiments, Compound A-2HCl is crystalline and is characterized as having at least two of the properties selected from a) to j). In some embodiments, Compound A-2HCl is crystalline and is characterized as having at least three of the properties selected from a) to j). In some embodiments, Compound A-2HCl is crystalline and is characterized as having at least four of the properties selected from a) to j). In some embodiments, Compound A-2HCl is crystalline and is characterized as having at least five of the properties selected from a) to j). In some embodiments, Compound A-2HCl is crystalline and is characterized as having at least six of the properties selected from a) to j). In some embodiments, Compound A-2HCl is crystalline and is characterized as having at least seven of the properties selected from a) to j). In some embodiments, Compound A-2HCl is crystalline and is characterized as having at least eight of the properties selected from a) to j). In some embodiments, Compound A-2HCl is crystalline and is characterized as having at least nine of the properties selected from a) to j). In some embodiments, Compound A-2HCl is crystalline and is characterized as having properties a), b), c), d), e), f), g), h), i), and j).

In some embodiments, Compound A-2HCl is crystalline and has an X-ray powder diffraction (XRPD) pattern with characteristic peaks at 5.4° 2-Theta, and 7.3° 2-Theta. In some embodiments, Compound A-2HCl is crystalline and has an X-ray powder diffraction (XRPD) pattern substantially the same as shown in FIG. 4. In some embodiments, Compound A-2HCl is crystalline and has a Differential Scanning Calorimetry (DSC) thermogram with an endotherm having an onset at about 233° C. and a peak at about 252° C. In some embodiments, Compound A-2HCl is crystalline and has a Differential Scanning Calorimetry (DSC) thermogram substantially the same as shown in FIG. 5(a). In some embodiments, Compound A-2HCl is crystalline and has an infrared (IR) spectrum with characteristic peaks at 2227 cm$^{-1}$, 1620 cm$^{-1}$, 1594 cm$^{-1}$, 1456 cm$^{-1}$, 1439 cm$^{-1}$, 1321 cm$^{-1}$, and 1122 cm$^{-1}$. In some embodiments, Compound A-2HCl is crystalline and has an infrared (IR) spectrum substantially the same as shown in FIG. 6. In some embodiments, Compound A-2HCl is crystalline and has reversible water uptake (~18% w/w) between 2 and 95% Relative Humidity (RH). In some embodiments, Compound A-2HCl is crystalline and has reversible water uptake (~9% w/w) between 2 and 95% Relative Humidity (RH). In some embodiments, Compound A-2HCl is crystalline and has an unchanged XRPD after DVS analysis at 90% RH and room temperature over 24 hours. In some embodiments, Compound A-2HCl is crystalline and has an unchanged XRPD after the DVS analysis at 75% RH and 40° C. over one week.

Synthesis of Compound A, Compound A-HCl, and Compound A-2HCl

Compounds described herein are synthesized using standard synthetic techniques or using methods known in the art in combination with methods described herein. Unless otherwise indicated, conventional methods of mass spectroscopy, NMR, HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In the reactions described, it may be necessary to protect reactive functional groups, for example hydroxy or amino groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Disclosed herein are methods for the synthesis of Compound A, Compound A-HCl, and Compound A-2HCl, as outlined in Scheme A.

Scheme A

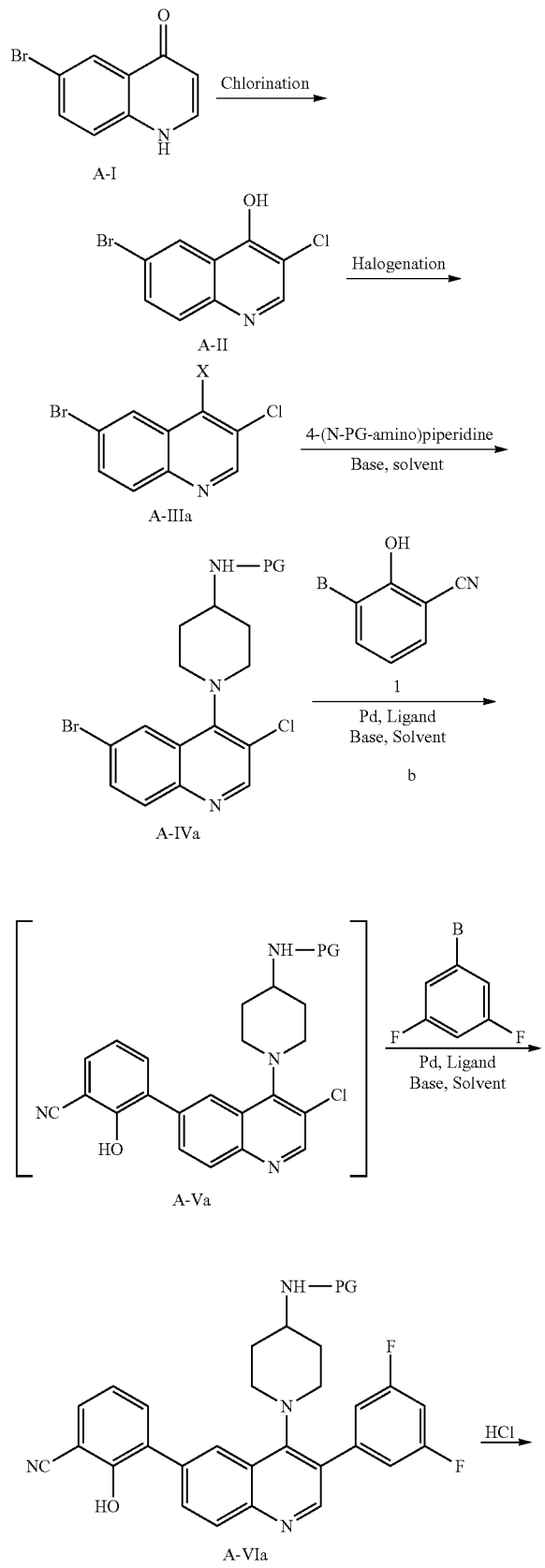

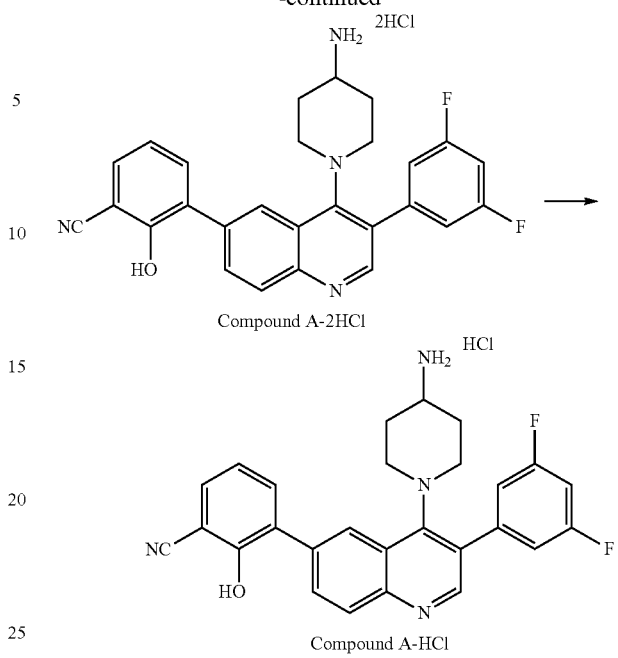

In some embodiments, chlorination of Compound A-I yields compound A-II. Compound A-II is reacted with a brominating or chlorinating agent to provide Compound A-IIIa (wherein X is Cl or Br). In some embodiments, Compound A-II is reacted with a brominating agent to provide Compound A-IIIa, where X is Br (i.e. Compound A-III). Coupling A-IIIa with 4-(N-PG-amino)piperidine yields compound A-IVa (where PG is a suitable amino protecting group). Compound A-IVa undergoes a Suzuki reaction with compound 1 to yield Compound A-Va, which undergoes a second Suzuki reaction with (3,5-difluorophenyl)B (where each B is independently a boronic acid, boronate ester, or trifluoroborate) to give Compound A-VIa. In some embodiments, each B is a boronic acid. In some embodiments, (3,5-difluorophenyl)B is (3,5-difluorophenyl) boronic acid. In some embodiments, the same Pd catalyst is used in both Suzuki reactions. In other embodiments, different Pd catalysts are used in each Suzuki reaction. In some embodiments, each Suzuki reaction is performed in the same solvent. In other embodiments, each Suzuki reaction is performed in different solvents. In some embodiments, Compound A-Va is isolated prior to the second Suzuki reactions. In other embodiments, the two Suzuki reactions are performed in one reaction vessel without isolation or purification of Compound A-Va. In some embodiments, residual Palladium is removed from Compound A-VIa via a palladium scavenger, such as $SiO_2$, charcoal, L-cysteine, SilicaBond Cysteine, Si-Thiol, SilicaBond DMT, or the like.

Deprotection of the PG group of Compound A-VIa and treatment with HCl yields Compound A-2HCl, which is converted to Compound A-HCl. In some embodiments, Compound A-HCl or Compound A-2HCl is treated with an appropriate base, such as sodium hydroxide, sodium carbonate, sodium bicarbonate, or the like, in order to yield Compound A (the free base form).

In some embodiments, when PG is tert-butyloxycarbonyl (Boc) then compound A-VIa is treated with HCl to provide Compound A-2HCl, which is converted to Compound A-HCl. In some embodiments, Compound A-HCl or Compound A-2HCl is treated with an appropriate base, such as sodium hydroxide, sodium carbonate, sodium bicarbonate, or the like, in order to yield Compound A (the free base form).

In some embodiments, the crystalline form of Compound A, Compound A-HCl, or Compound A-2HCl is isolated directly from the reaction mixture. In some embodiments, the crystalline form of Compound A, Compound A-HCl, or Compound A-2HCl is formed by recrystallization from a suitable solvent. Suitable solvents include, but are not limited to, water, methanol, ethanol, ethyl acetate, isopropyl acetate, pentane, hexanes, heptane, or combinations thereof.

Synthesis of 6-bromo-3-chloroquinolin-4-ol (A-II)

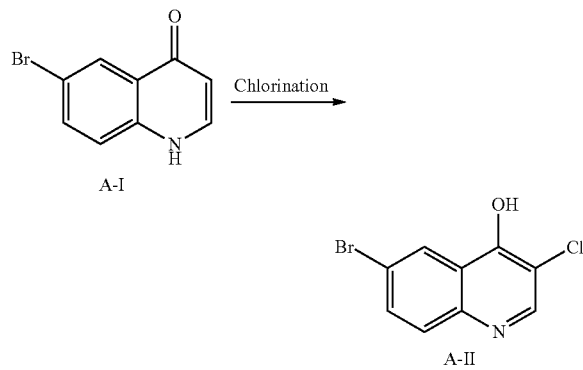

In some embodiments, Compound A-II is produced by chlorination of A-I. In some embodiments, chlorination is accomplished by treating A-I with a chlorinating agent, such as N-chlorosuccinimide (NCS), trichloroisocyanuric acid (TCA), sulfuryl chloride, chlorine, sodium hypochlorite, calcium hypochlorite, hypochlorous acid, or 2,3,4,5,6,6-hexachloro-2,4-cyclohexadien-1-one, or the like. In some embodiments, chlorination is accomplished by treating A-I with N-chlorosuccinimide (NCS).

In some embodiments, chlorination is performed in a suitable solvent such as acetic acid, water, ethanol, methanol, toluene, dichloromethane, tetrahydrofuran, dioxane, N,N-dimethylformamide, or the like.

In some embodiments, chlorination is performed in acetic acid. In some embodiments, 1 volume of acetic acid refers to an amount that is the same volume as the reagents in the reaction, i.e., A-I and/or NCS. In some embodiments, the reaction is performed in about 5, 7.5, 10, 12.5, 15, or 20 volumes of acetic acid. In some embodiments, the reaction is performed in about 10 volumes of acetic acid. In some embodiments, the reaction is performed in about 12.5 volumes of acetic acid. In some embodiments, the reaction is performed in about 20 volumes of acetic acid.

In some embodiments, chlorination is performed at elevated temperature. In some embodiments, the reaction temperature is between about 40° C. and about 150° C. In some embodiments, the reaction temperature is between about 40° C. and about 120° C. In some embodiments, the reaction temperature is between about 40° C. and about 100° C. In some embodiments, the reaction temperature is between about 40° C. and about 80° C. In some embodiments, the reaction temperature is between about 40° C. and about 60° C. In some embodiments, the reaction temperature is between about 45° C. and about 55° C. In some embodiments, the reaction temperature is about 40° C., 45° C., 50° C., 55° C., or 60° C. In some embodiments the reaction temperature is about 50° C.

Synthesis of 4,6-dibromo-3-chloroquinoline (A-III)

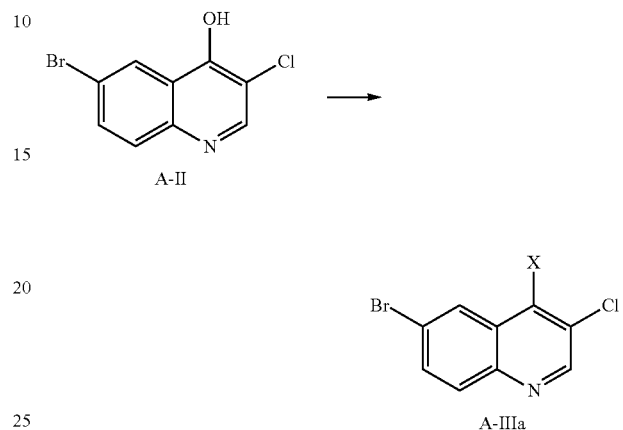

In some embodiments, the hydroxyl group of Compound A-II is converted to a halogen atom (X is Br or Cl). In some embodiments, halogenation is bromination. In some embodiments, halogenation is chlorination.

In some embodiments, Compound A-II is brominated with phosphorus tribromide (PBr$_3$), phosphorus oxybromide (POBr$_3$), hydrobromic acid, bromine, dibromotriphenylphosphorane, or the like. In some embodiment, A-II is brominated with PBr$_3$. In some embodiments, when A-II is brominated, the product is A-III.

In some embodiments, Compound A-II is chlorinated with POCl$_3$, thionyl chloride, or the like. In some embodiments, A-II is chlorinated with POCl$_3$.

In some embodiments, the halogenation reaction is conducted in a suitable solvent. In some embodiments, the suitable solvent is acetonitrile, water, ethanol, isopropanol, dichloromethane, toluene, N,N-dimethylformamide, acetic acid, acetone, or the like. In some embodiments, the halogenation solvent is DMF. In some embodiments, the reaction temperature is between 0° C. and 30° C. In some embodiments, the reaction temperature is between 0° C. and room temperature. In some embodiments, the reaction starts at 0° C. and warms to room temperature.

Synthesis of N-protected 1-(6-bromo-3-chloroquinolin-4-yl)piperidine (A-IVa)

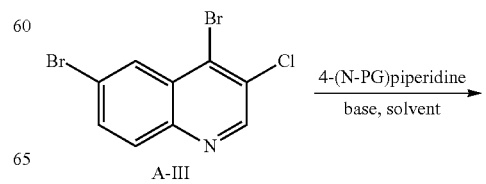

-continued

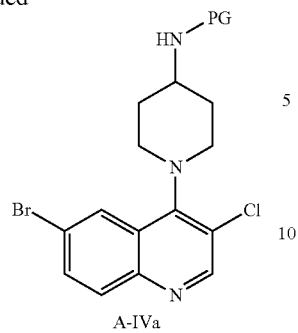

A-IVa

In some embodiments, Compound A-IVa is prepared from Compound A-III. In some embodiments, Compound A-IVa is made from Compound A-III by reacting Compound A-III with an N-protected 4-amino piperidine in the presence of a base in a suitable solvent.

In some embodiments, the amino protecting group is a carbamate (such as 9-fluorenylmethyl carbamate (Fmoc), t-butyl carbamate (Boc), benzyl carbamate (Cbz), or the like), an amide (such as acetyl, trifluoroacetyl, or the like), phalimide, benzyl, trityl, benzylidineamine, tosyl, or the like. In some embodiments, the amino protecting group is a carbamate. In some embodiments, the amino protecting group is Boc. In some embodiments, when the protecting group is Boc, the product is Compound A-IV.

In some embodiments, the base is a non-nucleophilic base. In some embodiments, the base is an amine base. In some embodiments, the base is an amine base such as triethylamine (TEA), diisopropylethylamine (DIPEA), 1,8-diazabicycloundec-7-ene (DBU), 1,2,2,6,6-pentamethylpiperidine, tributylamine, or the like. In some embodiments, the base is DIPEA.

In some embodiments, the base is an inorganic base. In some embodiments, the base is a carbonate ($MCO_3$) or bicarbonate ($MHCO_3$) base, where M is sodium, potassium, or cesium. In some embodiments, the base is an inorganic base such as sodium bicarbonate, $Na_2CO_3$, $K_2CO_3$, $Cs_2CO_3$, or the like.

In some embodiments, the suitable solvent for the reaction is N,N-dimethylformamide, N,N-dimethylacetamide, dimethylsulfoxide, dichlormethane, chloroform, dioxane, tetrahydrofuran, toluene, acetonitrile, ethanol, isopropanol, or the like. In some embodiments, the solvent for the reaction is dimethylsulfoxide.

In some embodiments, the reaction temperature is between about 0° C. and about 250° C., between about 50° C. and about 200° C., or between about 100° C. and about 180° C. In some embodiments, the reaction temperature is between about 120° C. and about 150° C. In some embodiments, the reaction temperature is about 100, 105, 110, 115, 120, 125, 130, 135, 140, 145, 150, 155, 160, 165, 170, 175, or 180° C.

Alternate Synthesis of N-Protected 1-(6-bromo-3-chloroquinolin-4-yl)piperidine (Compound A-IVa)

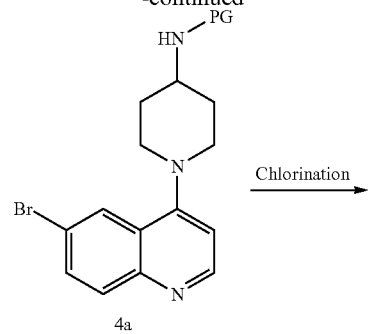

4a

In some embodiments, Compound A-IVa is prepared from Compound 3. In some embodiments, Compound A-IVa is made from Compound 3 by reacting Compound 3 with an N-protected 4-amino piperidine in the presence of a base in a suitable solvent to provide compound 4a, followed by a chlorination of Compound 4a. In some embodiments, when the protecting group is Boc, Compound 4a is Compound 4.

In some embodiments, the amino protecting group is a carbamate (such as 9-fluorenylmethyl carbamate (Fmoc), t-butyl carbamate (Boc), benzyl carbamate (Cbz), or the like), an amide (such as acetyl, trifluoroacetyl, or the like), phalimide, benzyl, trityl, benzylidineamine, tosyl, or the like. In some embodiments, the amino protecting group is a carbamate. In some embodiments, the amino protecting group is Boc. In some embodiments, when the protecting group is Boc, the product is Compound A-IV.

In some embodiments, the base is a non-nucleophilic base. In some embodiments, the base is an amine base. In some embodiments, the base is an amine base such as triethylamine (TEA), diisopropylethylamine (DIPEA), 1,8-diazabicycloundec-7-ene (DBU), 1,2,2,6,6-pentamethylpiperidine, tributylamine, or the like. In some embodiments, the base is DIPEA. In some embodiments, the base is an inorganic base. In some embodiments, the base is a carbonate ($MCO_3$) or bicarbonate ($MHCO_3$) base, where M is sodium, potassium, or cesium. In some embodiments, the base is an inorganic base such as sodium bicarbonate, $Na_2CO_3$, $K_2CO_3$, $Cs_2CO_3$ or the like. In some embodiments, the suitable solvent for the reaction is N,N-dimethylformamide, N,N-dimethylacetamide, dimethylsulfoxide, dichlormethane, chloroform, dioxane, tetrahydrofuran, toluene, acetonitrile, ethanol, isopropanol, or the like. In some embodiments, the solvent for the reaction is N,N-dimethylformamide. In some embodiments, the reaction temperature is between about 0° C. and about 250° C., between about 50° C. and about 200° C., or between about 100° C. and about 180° C. In some embodiments, the reaction temperature is between about 120° C. and about 150° C. In some embodiments, the reaction temperature is about 100, 105, 110, 115, 120, 125, 130, 135, 140, 145, 150, 155, 160, 165, 170, 175, or 180° C.

In some embodiments, Compound A-IVa is produced by chlorination of Compound 4a. In some embodiments, chlorination is accomplished by treating Compound 4a with a chlorinating agent, such as N-chlorosuccinimide (NCS), trichloroisocyanuric acid (TCA), sulfuryl chloride, chlorine, sodium hypochlorite, calcium hypochlorite, hypochlorous acid, or 2,3,4,5,6,6-hexachloro-2,4-cyclohexadien-1-one, or the like. In some embodiments, chlorination is accomplished by treating Compound 4a with N-chlorosuccinimide (NCS). In some embodiments, chlorination is performed in a suitable solvent such as acetic acid, water, ethanol, methanol, toluene, dichloromethane, tetrahydrofuran, dioxane, N,N-dimethylformamide, or the like. In some embodiments, the chlorination is performed in toluene. In some embodiments, the chlorination is performed at elevated temperature. In some embodiments, the reaction temperature is between about 40° C. and about 150° C. In some embodiments, the reaction temperature is between about 40° C. and about 120° C. In some embodiments, the reaction temperature is between about 40° C. and about 100° C. In some embodiments, the reaction temperature is between about 50° C. and about 80° C. In some embodiments the reaction temperature is about 70° C.

Synthesis of (3-cyano-2-hydroxyphenyl)boronic Acid (Compound 1)

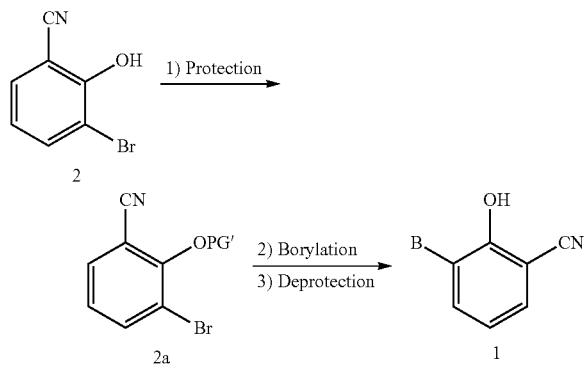

Also disclosed herein, is a two step process for the synthesis of Compound 1, wherein B is a boronic acid or boronate ester, the process comprises (1) protecting the hydroxyl group of Compound 2 with a suitable protecting group (PG') to generate Compound 2a; (2) reacting Compound 2a with a borylation agent under suitable reaction conditions; and (3) removal of the protecting group (PG') to provide Compound 1.

In some embodiments, the suitable protecting group (PG') is methoxymethyl (MOM), ethoxyethyl (EE), methoxypropyl (MOP), benzyloxymethyl (BOM), 2-methoxyethoxymethyl (MEM), benzyl (Bn), para-methoxybenzyl (PMB), 2-naphthylmethyl (Nap), methyl (Me), allyl, tetrahydropyranyl (THP), acetyl (Ac), benzoyl (Bz), 2,2,2-trichloroethyl carbonyl (Troc), [2-(trimethylsilyl)ethoxy]methyl, trimethylsilyl (TMS), triethylsilyl (TES), triisopropyl silyl (TIPS), tert-butyldimethylsilyl (TBDMS), or tert-butyldiphenylsilyl (TBDPS).

In some embodiments, the suitable protecting group (PG') is methoxymethyl, 2-methoxyethoxymethyl, benzyl, para-methoxybenzyl, methyl, allyl, tetrahydropyranyl, [2-(trimethylsilyl)ethoxy]methyl, trimethylsilyl, triethylsilyl, triisopropyl silyl, tert-butyldimethylsilyl, or tert-butyldiphenylsilyl. In some embodiments, the suitable protecting group (PG') is methoxymethyl, or 2-methoxyethoxymethyl. In some embodiments, the suitable protecting group (PG') is methoxymethyl. In some embodiments, the suitable protecting group (PG') is acetyl.

In some embodiments, removal of the protecting group in step (3) is accomplished with different reagents depending on what the protecting group is. In some embodiments, removal of the protecting group in step (3) is accomplished by treatment with hydrochloric acid, hydrobromic acid, acetic acid, trifluoroacetic acid, tosic acid, $ZnBr_2$, hydrogen over Pd/C, 2,3-dichloro-5,6-dicyano-1,4-benzoquinone (DDQ), boron tribromide, boron trichloride, trimethylsilyl iodide, $Pd(PPh_3)_4$, tetra-n-butylammonium fluoride (TBAF), or HF-pyridine. In some embodiments, removal of the protecting group in step (3) is accomplished by treatment with hydrochloric acid, hydrobromic acid, acetic acid, trifluoroacetic acid, or tosic acid. In some embodiments, removal of the protecting group in step (3) is accomplished by treatment with hydrochloric acid.

In some embodiments, the borylation agent is pinacolborane, catecholborane, bis(neopentyl glycolato)diboron, bis(pinacolato)diboron, bis(hexylene glycolato)diboron, bis(catecholato)diboron, tetrahydroxydiboron, trimethoxyboron, triisopropoxyboron, 4,4,5,5-tetramethyl-1,3,2-dioxaborolane, 4,6,6-trimethyl-1,3,2-dioxaborinane, diisopropylamine borane, bis(neopentyl glycolato)diboron, bis(catecholato)diboron, or bis(pinacolato)diboron. In some embodiments, the suitable reaction conditions of (2) comprise the use of metal halogen exchange reagents. In some embodiments, the suitable reaction conditions of (2) comprise the use of metal halogen exchange reagents selected from Grignard reagents and alkyl lithium reagents. In some embodiments, the suitable reaction conditions of (2) comprise the use of isopropyl magnesium chloride in tetrahydrofuran. In some embodiments, the borylation agent is triisopropoxyboron and the suitable reaction conditions of (2) comprise the use of isopropyl magnesium chloride in tetrahydrofuran. In some embodiments, the suitable reaction conditions of (2) comprise the use of transition metal mediated reaction conditions. In some embodiments, the suitable reaction conditions of (2) comprise the use of palladium metal mediated reaction conditions.

In some embodiments, B is a boronic acid or a boronic ester. In some embodiments, B is

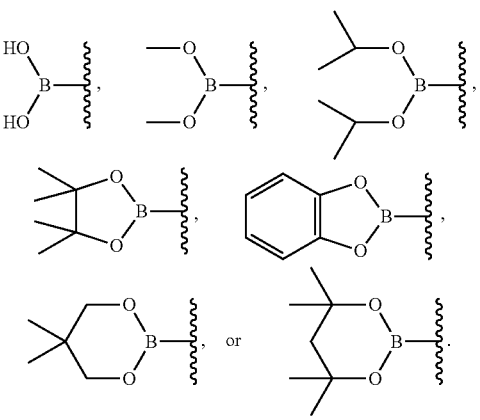

In some embodiments, B is a boronic acid. In some embodiments, B is

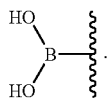

In some embodiments, B is a boronic ester. In some embodiments, B is

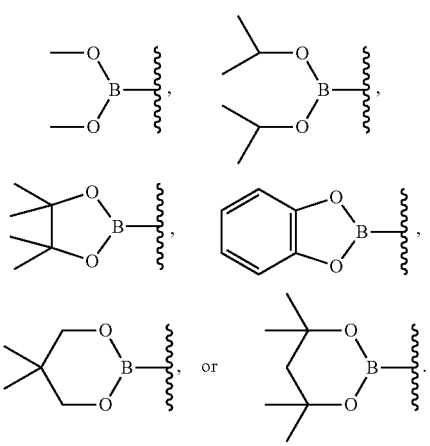

In some embodiments, the process further comprises an additional step of (4) converting the boronic acid or boronate ester to a trifluoroborate. In such embodiments, B is

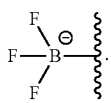

In some embodiments, this conversion is achieved by treating the boron containing compound with KHF$_2$.

Synthesis of tert-butyl (1-(6-(3-cyano-2-hydroxyphenyl)-3-(3,5-difluorophenyl)quinolin-4-yl)piperidin-4-yl)carbamate (Compound A-VI)

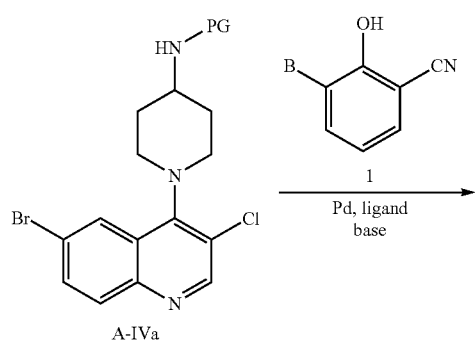

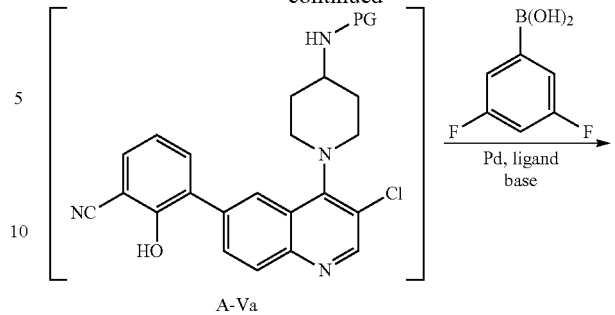

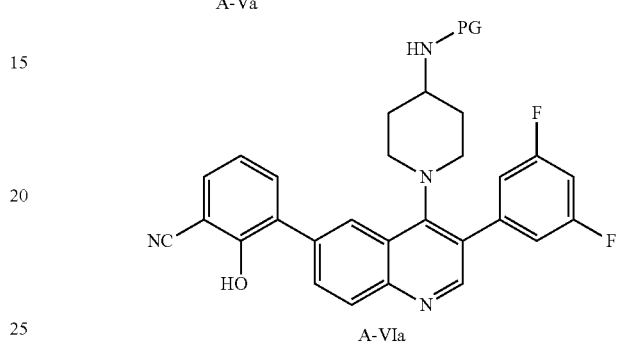

In some embodiments, Compound A-VIa is synthesized from Compound A-IVa. In some embodiments, Compound A-VIa is prepared by conducting two successive Suzuki reactions of A-IVa. In some embodiments, Compound A-IVa is reacted in a first Suzuki reaction with Compound 1, a suitable palladium catalyst, suitable ligand, and a suitable base in a suitable solvent to yield Compound A-Va. In some embodiments, Compound A-Va is reacted in a second Suzuki reaction with 3,5-difluorophenylboronic acid, a suitable palladium catalyst, suitable ligand, and a suitable base in a suitable solvent to yield Compound A-VIa. In some embodiments, Compound A-Va is isolated prior to the second Suzuki reaction. In some embodiments, Compound A-Va is not isolated prior to the second Suzuki reaction. When PG is Boc, then Compound A-Va is Compound A-V.

In some embodiments, suitable bases in Suzuki reactions include amine bases and inorganic bases. Suitable amine bases for Suzuki reactions include, but are not limited to, triethylamine, diisopropylethylamine, 1,2,2,6,6-pentamethylpiperidine, tributylamine, 1,8-diazabicycloundec-7-ene (DBU), or the like. Suitable inorganic bases for Suzuki reactions include, but are not limited to, NaOAc, KOAc, Ba(OH)$_2$, Li$_2$CO$_3$, Na$_2$CO$_3$, K$_2$CO$_3$, Cs$_2$CO$_3$, Na$_3$PO$_4$, K$_3$PO$_4$, or the like. In some embodiments, the base in each Suzuki reaction is the same. In some embodiments, the base in each Suzuki reaction is not the same. In some embodiments, about 1, 2, 3, 4, 5, or 6 equivalents of the base is used in the Suzuki reaction(s). In some embodiments, when Compound A-Va is not isolated prior to the second Suzuki reaction, no additional base is added to the reaction.

In some embodiments, the amount of palladium for each Suzuki reaction is less than about 0.05 equiv. In some embodiments, the amount of palladium for each Suzuki reaction is from about 0.05 equiv to about 0.2 equiv. In some embodiments, the amount of palladium for each Suzuki reaction is about 0.05, 0.1, 0.15, or 0.2 equiv. In some embodiments, the amount of palladium for each Suzuki reaction is the same. In some embodiments, the amount of palladium for each Suzuki reaction is not the same.

In some embodiments, a suitable ligand is used for the palladium catalyst. In some embodiments, the ligand is a phosphine ligand. In some embodiments, the ligand is an aliphatic phosphine ligand, such as trimethyl phosphine, tricyclohexylphosphine, tri-tert-butyl-phosphine or the like. In some embodiments, the ligand is an aromatic phosphine, such as XPhos, SPhos, JohnPhos, Amphos, triphenylphosphine, methyldiphenylphosphine, or the like. In some embodiments, the ligand is a phosphite ligand, such as trimethylphosphite, triphenylphosphite, or the like. In some embodiments, the ligand is a bis-phosphine ligand, such as diphenylphosphinomethane (dppm), diphenyl phosphinoethane (dppe), 1,1'-bis(diphenylphosphino)ferrocene (dppf), or the like. In some embodiments, the ligand in each Suzuki reaction is the same. In some embodiments, the ligand for each Suzuki reaction is not the same.

In some embodiments, the palladium source in one or both Suzuki reactions is a Pd(0) source, such as $Pd_2(dba)_3$, $Pd(PPh_3)_4$, or the like. In some embodiments, the palladium source in one or both Suzuki reactions is a Pd(II) source, such as $PdCl_2$, $Pd(OAc)_2$, $PdCl_2(PPh_3)_2$, $PdCl_2(dppf).DCM$, $PdCl_2(Amphos)$, or the like. In some embodiments, the palladium source in each Suzuki reaction is the same. In some embodiments, the palladium source in each Suzuki reaction is different.

In some embodiments, the solvent system used in one or both Suzuki reactions is a single solvent. In some embodiments, the solvent system used in one or both Suzuki reaction is a cosolvent mixture. In some embodiments, the solvent system used in one or both Suzuki reactions is toluene, DMF, acetonitrile, EtOH, IPA, THF, dioxane, water, or mixtures thereof. In some embodiments, the solvent system used in each Suzuki reaction is the same. In some embodiments, the solvent system used in each Suzuki reaction is not the same.

In some embodiments, the temperature used in one or both Suzuki reaction is between about 50° and 150° C., preferably between about 60° C. and 120° C. In some embodiments, the temperature used in one or both Suzuki reaction is between 80° C. and 85° C. In some embodiments, the temperature used in one or both Suzuki reaction is between 90° C. and 100° C. In some embodiments, each Suzuki reaction is performed at the same temperature. In some embodiments, each Suzuki reaction is performed at a different temperature.

In some embodiments, Compound A-Va is isolated between reactions. In some embodiments Compound A-Va is not isolated between reactions. In some embodiments, each Suzuki reaction is performed in the same reaction vessel. In some embodiments, each Suzuki reaction is performed in the same reaction vessel without isolation of Compound A-Va. In some embodiments, each Suzuki reaction is performed in the same solvent. In some embodiments, each Suzuki reaction is performed with the same base.

In one aspect, the two Suzuki reactions are performed successively in the same reaction vessel without isolation of intermediate A-Va, and without removal of the solvent, wherein, after the first reaction is completed, the reaction vessel is allowed to cool prior to addition of the second boronic acid and then the reaction vessel is heated for the second Suzuki reaction. In some embodiments, a second palladium source and/or ligand is added with the second boronic acid. In some embodiments, no additional palladium source and/or ligand is added with the second boronic acid. In some embodiments, additional base is added to the reaction with the second boronic acid. In some embodiments, no additional base is added to the reaction with the second boronic acid.

In some embodiments, the progress of one or both Suzuki reactions is monitored by HPLC or by TLC.

In some embodiments, the solvent system used is 10:1 dioxane:water. In some embodiments, the base used is $K_2CO_3$ and 4 equiv of base are used. In some embodiments, the first palladium source is $PdCl_2(dppf).CH_2Cl_2$. In some embodiments, the second palladium source is $PdCl_2(Amphos)$. In some embodiments, the first Suzuki reaction proceeds at about 80-85° C. In some embodiments, the second Suzuki reaction proceeds at about 90-100° C.

In some embodiments, Compound A-VIa contains a detectable amount of residual palladium as an impurity. When PG is Boc, then Compound A-VIa is Compound A-VI.

In some embodiments, the isolated product of Compound A-VI contains a detectable amount of unreacted Compound A-V. In some embodiments, a sample of Compound A-VI contains a detectable amount of an impurity selected from:

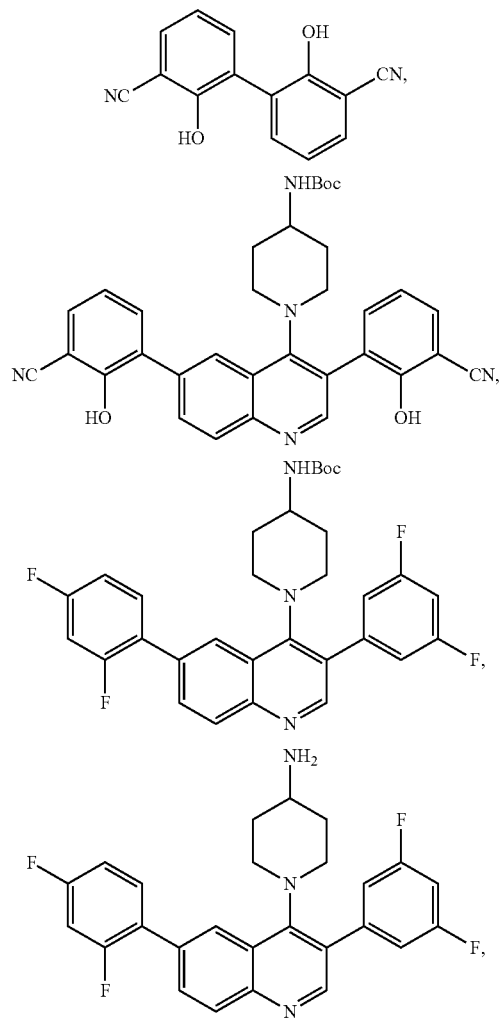

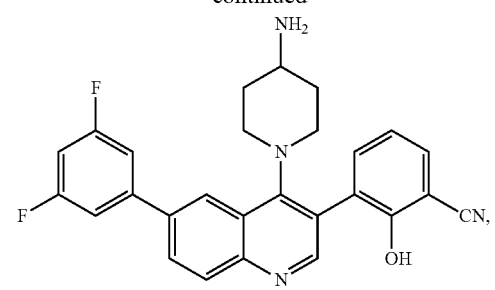
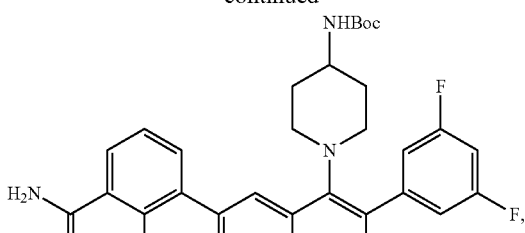
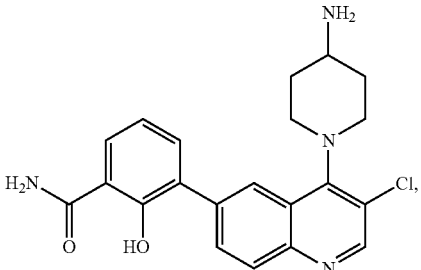
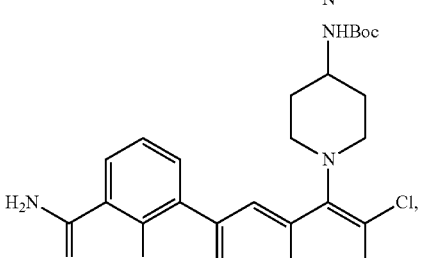
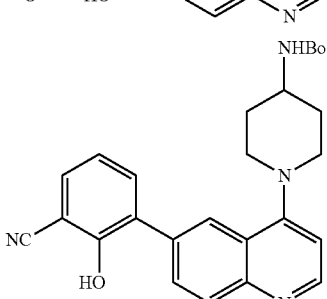
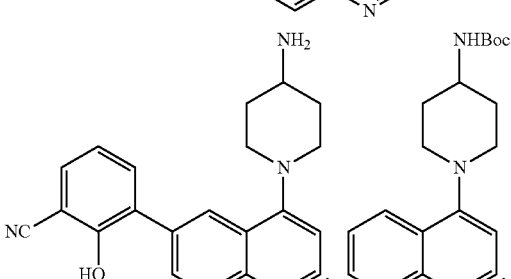
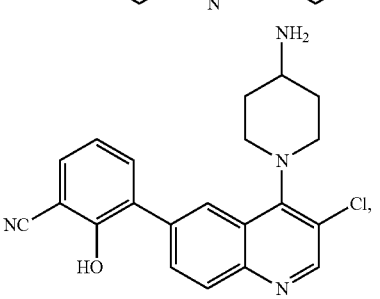

-continued

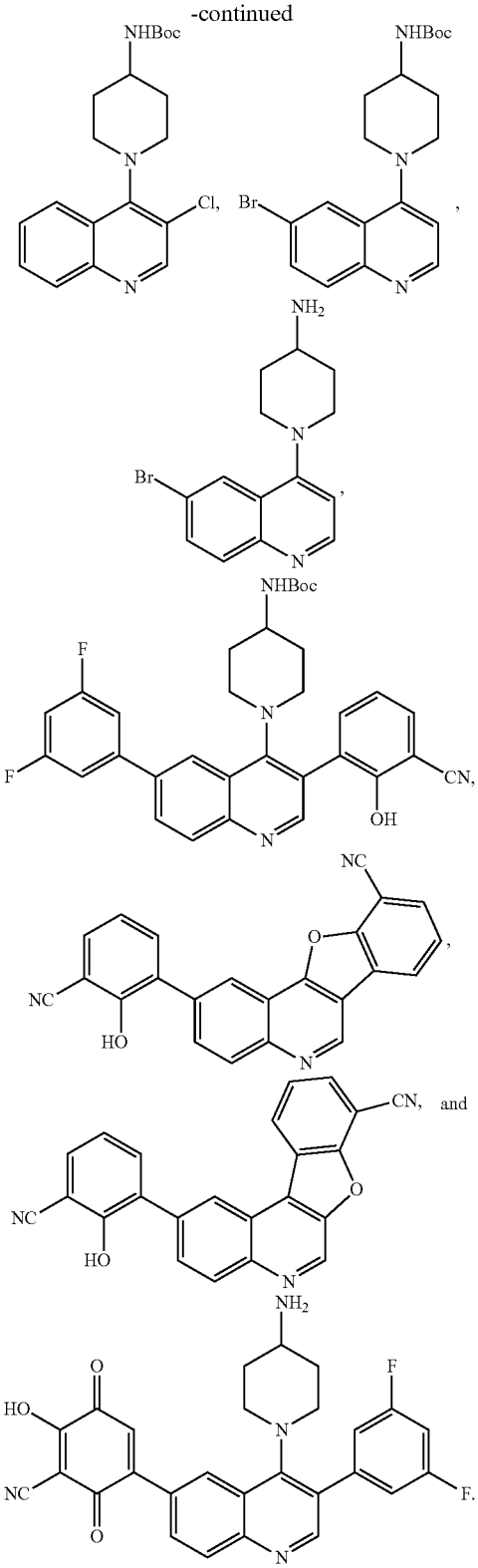

recrystallization/slurrying removes or reduces the amount of residual palladium in samples of Compound A-VI.

TABLE 1

| Crystallization (RC)/ slurry | HPLC purity of Solid[a] | | |
|---|---|---|---|
| | Purity (%) | Un-reacted Compound A-V (%) | Other Impurity (%) |
| RC from MTBE | 96.22 | 1.05 | 2.72 |
| RC from IPA | 97.10 | 0.68 | 2.22 |
| RC from EA | 95.47 | 2.18 | 2.35 |
| RC from MeOH | 92.96 | 1.60 | 1.86 |
| Precipitation from DCM/pet ether | 96.28 | 1.09 | 1.86 |
| Slurry in ACN | 95.61 | 1.32 | 2.51 |
| RC from THF/water | 93.72 | 2.27 | 3.40 |
| Precipitation from DMF/water | 94.35 | 2.17 | 2.85 |
| RT Slurry in Toluene | 96.36 | 0.41 | 3.24 |
| Hot slurry in Toluene | 97.57 | 0.16 | 2.28 |
| From DCM/MTBE | 96.78 | 0.80 | 2.42 |
| Hot slurry from IPAc | 98.13 | 0.00 | 1.87 |
| RC from THF/pet ether | 98.24 | 0.16 | 1.59 |
| Hot slurry in MeOH | 96.30 | 0.35 | 3.35 |

[a]The purity of the starting A-VI for all the RC/slurry studies was 96.18%.

Due to the fact that the synthetic methods described above utilize a transition metal catalyst, purification steps are performed to reduce the amount of palladium in the product. Purification steps to reduce the amount of palladium in a product are conducted so that active pharmaceutical ingredients meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In some embodiments, purification steps to reduce the amount of palladium in a product includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetylcysteine, n-Bu3P, crystallization, extraction, 1-cysteine, n-Bu3P/lactic acid (Garrett et al., *Adv. Synth. Catal.* 2004, 346, 889-900). In some embodiments, activated carbon includes but is not limited to DARCO® KB-G, DARCO® KB-WJ. In one aspect silica bound scavengers include but are not limited to

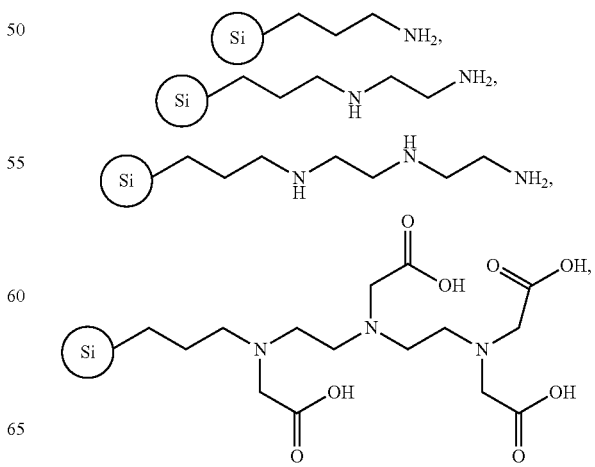

In some embodiments, Compound A-VI is purified by recrystallization. In some embodiments, Compound A-VI is heated in a suitable solvent or solvent mixture for an appropriate amount of time. In some embodiments, the purity of Compound A-VI is improved by this process (see Table 1 below). In some embodiments, this process of

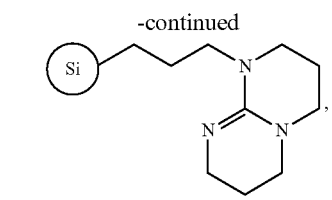

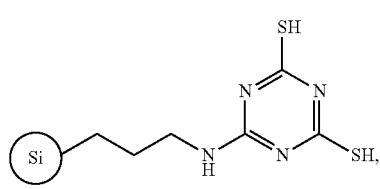

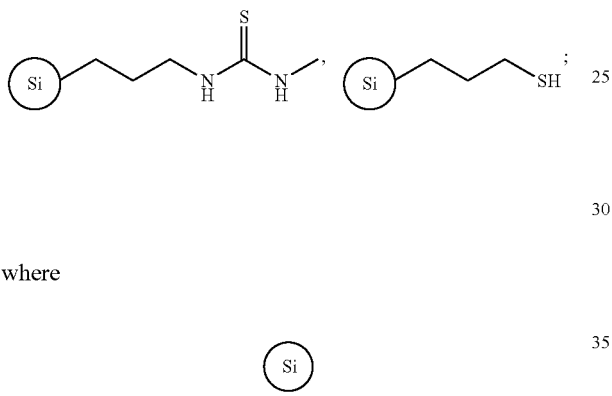

where

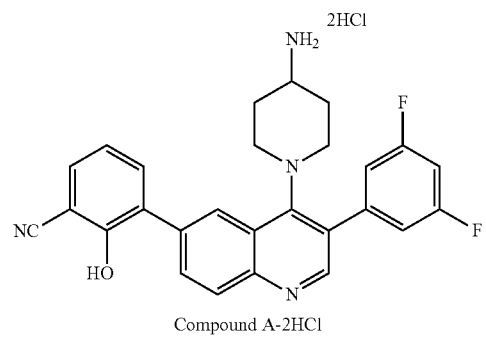

denotes silica gel. In some embodiments, the purification steps to reduce the amount of palladium include the use of activated carbon, derivatized silica gel (e.g., thiol derivatized silica gel), or combinations thereof.

In some embodiments, A-VI is further treated with a metal scavenger to remove residual palladium. In some embodiments, the metal scavenger comprises SiO2, charcoal, aqueous solution of L-cysteine, a Silicycle metal scavenger, Si-thiol, SiliaBond DMT or SiliaBond Cysteine. In some embodiments, the scavenger loading (w/w) is 1:3, 1:2, or 1:1. In some embodiments, the metal scavenger is Si-thiol.

In some embodiments, crude A-VI as isolated from the reaction is treated with a metal scavenger. In some other embodiments, recrystallized A-VI is treated with a metal scavenger. In some of these embodiments, palladium levels are reduced sufficiently to be undetectable.

In some embodiments, the presence of residual heavy metal (e.g. palladium) impurities is determined by utilizing methods known in the art. In some embodiments, the presence of residual heavy metal (e.g. palladium) impurities is determined by the use of inductively coupled plasma mass spectrometry (ICP-MS). In some embodiments, the presence of residual heavy metal (e.g. palladium) impurities is determined by the use of techniques described in U.S. Pharmacopeia General Chapter <231> Heavy Metals.

Synthesis of 3-(4-(4-amino-piperidin-1-yl)-3-(3,5-difluoro-phenyl)-quinolin-6-yl)-2-hydroxy-benzonitrile, di-HCl Salt (Compound A-2HCl)

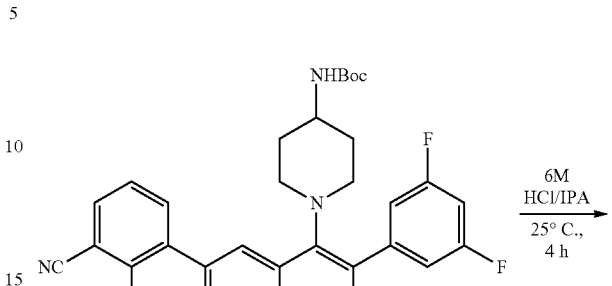

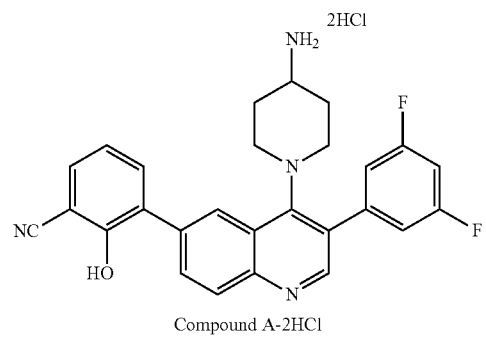

In some embodiments, Compound A-VI is treated with hydrochloric acid in a suitable solvent to yield Compound A-2HCl. In some embodiments, the suitable solvent is isopropyl alcohol (IPA), methyl tert-butyl ether (MTBE), toluene, ethyl acetate, isopropyl acetate, water, or mixtures thereof. In some embodiments, the suitable solvent is isopropyl alcohol, ethyl acetate, or isopropyl acetate. In some embodiments, the suitable solvent is IPA.

Preparation of Compound A-HCl from Compound A-2HCl

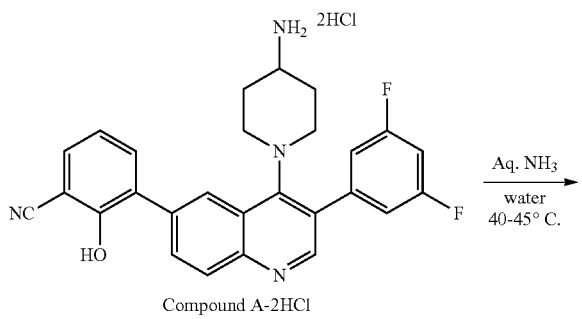

-continued

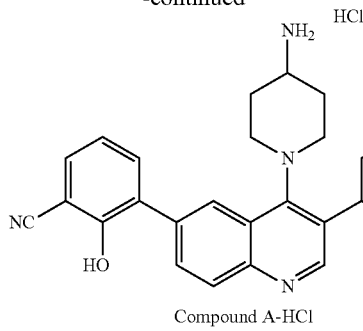

Compound A-HCl

Preparation of Compound A from Compound A-2HCl

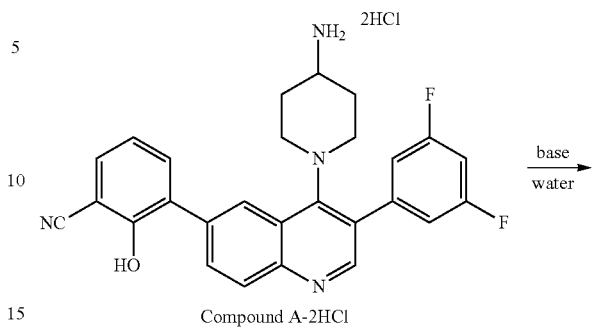

Compound A-2HCl

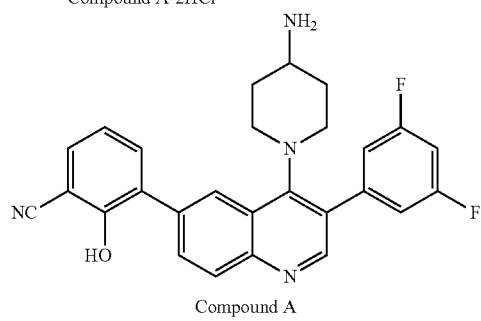

Compound A

In some embodiments, Compound A-2HCl is dissolved in a suitable solvent and treated with aqueous ammonia to yield Compound A-HCl. In some embodiments, the suitable solvent is IPA, water, methyl acetate or combinations thereof. In some embodiments, the solvent is water. In some embodiments, the solvent is IPA:water in a ratio of 9:1, 8:2, 7:3, 6:4, or 5:5. In some embodiments, the solvent is methyl acetate:water in a ratio of 9:1, 8:2, 7:3, 6:4, or 5:5. In some embodiments, additional sodium bicarbonate is added to the reaction. In some embodiments the solvent volume is 5, 10, 15, 20, or more than 20 volumes.

In some embodiments, the aqueous ammonia source is saturated ammonium chloride (28-30%). In other embodiments, the aqueous ammonia source is 25%. In some embodiments, about 1 equivalent of ammonia is added. In some embodiments, less than 1 equivalent of ammonia is added, e.g., 0.8 equiv. In some embodiments, more than one equivalent of ammonia is added, e.g., 1.25 equiv. In some embodiments, the amount of ammonia added is determined by monitoring the pH of the solution. In some embodiments, the pH is adjusted to about 4-6 with the addition of ammonia, bicarbonate, or hydroxide. In some embodiments, the pH is adjusted with the addition of ammonia. In some embodiments, the pH is adjusted to about 4.5 to 4.7 with the addition of ammonia.

In some embodiments, the reaction is heated to about 30, 35, 40, 45, 50, 55, or 60° C. In some embodiments, the reaction is heated to about 45° C. In some embodiments, the reaction is heated before addition of the ammonia.

In some embodiments, water is added to the reaction mixture while heating. In some embodiments, water is added to the reaction mixture at the end of the reaction. In some embodiments, water is added over about 2 hours to the reaction mixture.

In some embodiments, the slurry is filtered to isolate Compound A-HCl, or solvate thereof.

In some other embodiments, no ammonia is needed to convert Compound A-2HCl to Compound A-HCl. In some embodiments, Compound A-2HCl is stirred in about 10, about 20, about 30, about 40, or about 50 volumes of water. In some embodiments, Compound A-2HCl is stirred in about 20 to about 50 volumes of water. In some embodiments, sodium bicarbonate is added to the water mixture to adjust the pH. In some embodiments, Compound A-HCl is isolated from filtering the solids from this water mixture.

In some embodiments, the free base of Compound A is made by treating Compound A-2HCl with a suitable base in a suitable solvent. In some embodiments, the suitable base is sodium hydroxide, sodium bicarbonate, or the like. In some embodiments, the suitable solvent is water. In some embodiments, the solid is filtered from the mixture to isolate the free base of Compound A.

Preparation of Compound A-HCl from Compound A

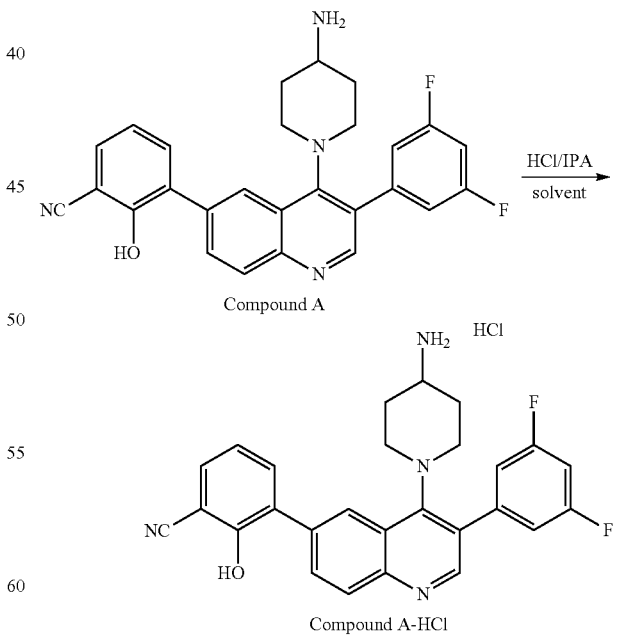

In some embodiments Compound A-HCl is generated by treating the free base with about 1 equivalent of HCl in a suitable solvent. In some embodiments, the suitable solvent is methanol, ethanol, isopropyl alcohol, acetone, methyl acetate, ethyl acetate, isopropyl acetate, tetrahydrofuran, tetrahydropyran, water, acetone, or combinations thereof. In some embodiments, the HCl source is HCl in IPA, HCl in toluene, HCl in MTBE, or HCl in water. In some embodiments, Compound A-HCl is isolated by filtering the solids from the reaction mixture.

Additional Compounds

In another aspect, described herein is a compound of Formula (I), or a pharmaceutically acceptable salt, pharmaceutically acceptable solvate, diastereomeric mixture, or enantiomer thereof:

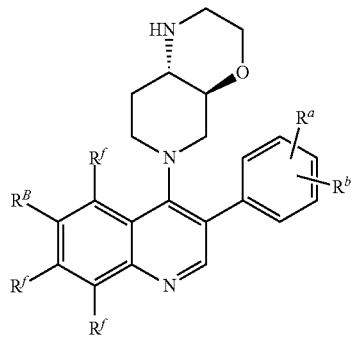

Formula (I)

wherein:

$R^a$ is F, Cl, or —CH$_3$;

$R^b$ is hydrogen, F, Cl, —CH$_3$, —CN, —OH, or —OCH$_3$;

$R^B$ is an unsubstituted or substituted phenyl or an unsubstituted or substituted pyridinyl, wherein if $R^B$ is substituted then $R^B$ is substituted with $R^c$ and $R^d$;

$R^c$ is hydrogen, F, Cl, Br, —CH$_3$, —CN, —OH, —OCH$_3$, —C(=NOCH$_3$)H, or —C(=NOH)H;

$R^d$ is —OH, or —NH$_2$; and each $R^f$ is hydrogen or F.

In some embodiments, the compound of Formula (I) has the structure of Formula (Ia), or a pharmaceutically acceptable salt, solvate, diastereomeric mixture, individual enantiomers or prodrug thereof:

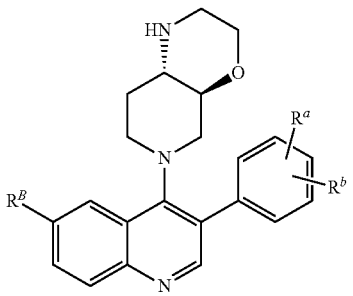

Formula (Ia)

In some embodiments, $R^B$ as described in Table 2.

In some embodiments, compounds described herein have the following structure, or a pharmaceutically acceptable salt, solvate, diastereomeric mixture, or individual enantiomers thereof:

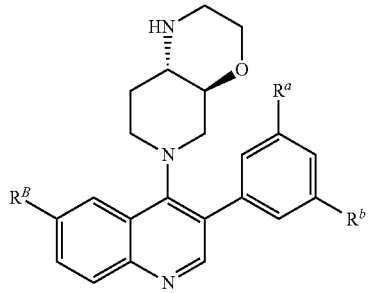

wherein, $R^a$, $R^b$, and $R^B$ are as described in Table 2.

In some embodiments, $R^a$, $R^b$, and $R^B$ are as described in Table 2.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in Table 2.

TABLE 2

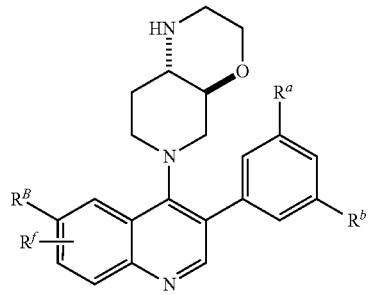

| Cpd No. | $R^f$ | $R^B$ | $R^a$ | $R^b$ |
|---|---|---|---|---|
| 1-1 | H | ![structure with =N-OH and OH on phenyl] | F | F |
| 1-2 | H | ![structure with =N-O-CH3 and NH2 on pyridine] | F | —CH3 |

TABLE 2-continued

[Structure diagram of quinoline compound with octahydro-pyrido-oxazine substituent, R^B, R^f, R^a, R^b positions]

| Cpd No. | R^f | R^B | R^a | R^b |
|---------|-----|-----|-----|-----|
| 1-3 | H | [CH=N-OCH3 group on 3-aminopyridine] | Cl | F |
| 1-4 | H | [CN group on 3-aminopyridine] | F | —CH3 |
| 1-5 | H | [CN group on 3-aminopyridine] | Cl | F |
| 1-6 | H | [CH=N-OH group on 3-aminopyridine] | F | F |
| 1-7 | H | [CN group on 3-aminopyridine] | F | H |

TABLE 2-continued

[Structure diagram of quinoline compound with octahydro-pyrido-oxazine substituent, R^B, R^f, R^a, R^b positions]

| Cpd No. | R^f | R^B | R^a | R^b |
|---------|-----|-----|-----|-----|
| 1-8 | H | CH3 [with 3-amino-4-methylpyridine] | F | H |

Compounds in Table 2 are named:

1-1: 2-{4-[(4aS,8aS)-octahydro-1H-pyrido[3,4-b][1,4]oxazin-6-yl]-3-(3,5-difluorophenyl)quinolin-6-yl}-6-[(1E)-(hydroxyimino)methyl]phenol;

1-2: 2-{4-[(4aS,8aS)-octahydro-1H-pyrido[3,4-b][1,4]oxazin-6-yl]-3-(3-fluoro-5-methylphenyl)quinolin-6-yl}-4-[(1E)-(methoxyimino)methyl]pyridin-3-amine;

1-3: 2-{4-[(4aS,8aS)-octahydro-1H-pyrido[3,4-b][1,4]oxazin-6-yl]-3-(3-chloro-5-fluorophenyl)quinolin-6-yl}-4-[(1E)-(methoxyimino)methyl]pyridin-3-amine;

1-4: 2-{4-[(4aS,8aS)-octahydro-1H-pyrido[3,4-b][1,4]oxazin-6-yl]-3-(3-fluoro-5-methylphenyl)quinolin-6-yl}-3-aminopyridine-4-carbonitrile;

1-5: 2-{4-[(4aS,8aS)-octahydro-1H-pyrido[3,4-b][1,4]oxazin-6-yl]-3-(3-chloro-5-fluorophenyl)quinolin-6-yl}-3-aminopyridine-4-carbonitrile;

1-6: 2-{4-[(4aS,8aS)-octahydro-1H-pyrido[3,4-b][1,4]oxazin-6-yl]-3-(3,5-difluorophenyl)quinolin-6-yl}-4-[(1E)-(hydroxyimino)methyl]pyridin-3-amine;

1-7: 2-{4-[(4aS,8aS)-octahydro-1H-pyrido[3,4-b][1,4]oxazin-6-yl]-3-(3-fluorophenyl)quinolin-6-yl}-3-aminopyridine-4-carbonitrile; and 1-8: 2-{4-[(4aS,8aS)-octahydro-1H-pyrido[3,4-b][1,4]oxazin-6-yl]-3-(3-fluorophenyl)quinolin-6-yl}-4-methylpyridin-3-amine.

In some embodiments, provided herein is a pharmaceutically acceptable salt of a compound that is described in Table 2.

Also provided herein is 1-9: 3-[4-(4-aminopiperidin-1-yl)-5-fluoro-3-(3-fluoro-5-methylphenyl)quinolin-6-yl]-2-hydroxybenzonitrile, or a pharmaceutically acceptable salt thereof.

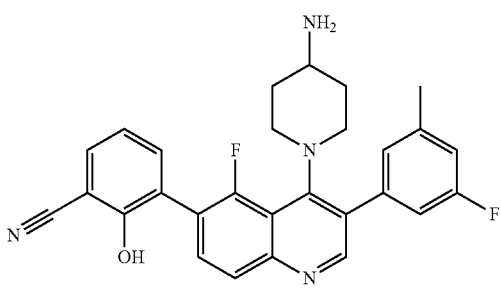 [SMILES: Cc1cc(F)cc(-c2cnc3ccc(-c4cccc(C#N)c4O)c(F)c3c2N2CCC(N)CC2)c1]

Also provided herein is 1-10: 3-[4-(4-aminopiperidin-1-yl)-7-fluoro-3-(3-fluoro-5-methylphenyl)quinolin-6-yl]-2-hydroxybenzonitrile, or a pharmaceutically acceptable salt thereof.

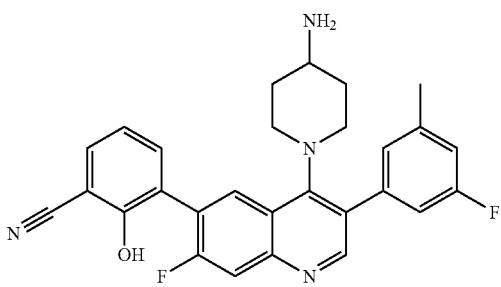 [SMILES: Cc1cc(F)cc(-c2cnc3cc(F)c(-c4cccc(C#N)c4O)cc3c2N2CCC(N)CC2)c1]

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as described in Scheme B.

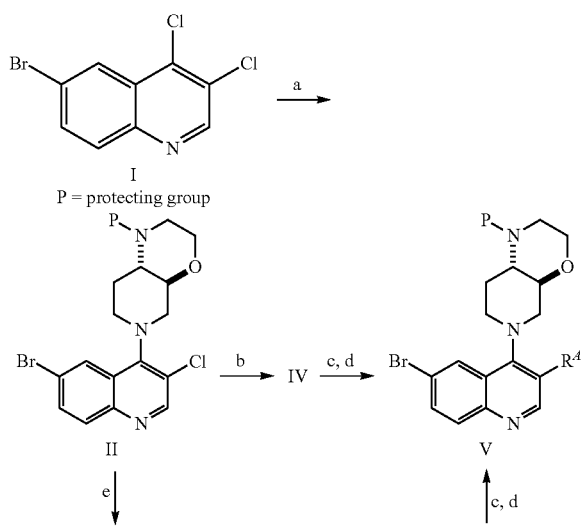

a) cyclic amine, Et$_3$N; b) R$^B$B(OH)$_2$, Pd; c) R$^A$B(OH)$_2$, Pd; d) deprotection; e) bis(pinacolato)diboron, Pd, X-Phos, KOAc; f) R$^B$X, Pd In some embodiments, Compound I is converted to Compound II by a nucleophilic replacement with a corresponding cyclic amine over chloro in the presence of Et$_3$N or DIEA. Selective Suzuki-Miyaura reactions with R$^B$B(OH)$_2$ or its boronic ester yield Compound IV, which can also be prepared by a two-step sequence through the formation of boronic ester (Compound III) followed by selective Suzuki-Miyaura reactions with R$^B$X (X=Cl, Br, or I). Suzuki-Miyaura reactions with R$^A$(OH)$_2$ or its boronic ester followed by removal of all protecting groups using appropriate de-protection methods such as acid lead to the formation of Compound V.

In some embodiments, the compounds obtained from the above mentioned methods are prepared as racemic or diastereomic mixtures. In some other embodiments, racemic mixtures of the compounds are separated to obtain optically pure (or optically enriched) isomers by the use of common chiral separation methods such as chiral HPLC, chiral supercritical fluid chromatographic system (SFC), simulated moving bed chromatography (SMB), and the like.

In some other embodiments, diastereomic mixtures of the compounds are separated to obtain optically pure (or optically enriched) isomers by the use of crystallization methods or common non-chiral chromatography methods such as silica gel chromatography or chiral chromatography methods such as chiral HPLC, chiral supercritical fluid chromatographic system (SFC), simulated moving bed chromatography (SMB), and the like.

In some embodiments, compounds described herein are synthesized as outlined in the Examples.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound disclosed herein is prepared as a chloride salt, sulfate salt, bromide salt, mesylate salt, maleate salt, citrate salt or phosphate salt.

In some embodiments, pharmaceutically acceptable salts are obtained by reacting a compound disclosed herein with a base. In some embodiments, the compound disclosed herein is acidic and is reacted with a base. In such situations, an acidic proton of the compound disclosed herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound A, or a pharmaceutically acceptable salt thereof, comprise an organic solvent(s). In some embodiments, compositions comprising Compound A, or a pharmaceutically acceptable salt thereof, include a residual amount of an organic solvent(s). In some embodiments, compositions comprising Compound A, or a pharmaceutically acceptable salt thereof, comprise a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising Compound A, or a pharmaceutically acceptable salt thereof, include a detectable amount of an organic solvent. In some embodiments, the pharmaceutically acceptable salt of Compound A is an HCl salt (i.e., Compound A-HCl). In some embodiments, the organic solvent is a Class 3 solvent.

In other embodiments are compositions comprising Compound A, or a pharmaceutically acceptable salt thereof, wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound A, or a pharmaceutically acceptable salt thereof, wherein the composition comprises a detectable amount of solvent which is less than about 5000 ppm. In yet a further embodiment are compositions comprising Compound A, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

The methods and formulations described herein include the use of N-oxides (if appropriate), or pharmaceutically acceptable salts of compounds having the structure disclosed herein, as well as active metabolites of these compounds having the same type of activity.

In some embodiments, sites on the organic radicals (e.g. alkyl groups, aromatic rings) of compounds disclosed herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or altered metabolic pathways to reduce undesirable metabolites or reduced dosage requirements.

In some embodiments, one or more hydrogen atoms on Compound A are replaced with deuterium. In some embodiments, substitution with deuterium affords certain therapeutic advantages resulting from greater metabolic stability, such as, for example, increased in vivo half-life or reduced dosage requirements.

In one aspect, described is a compound with the following structure:

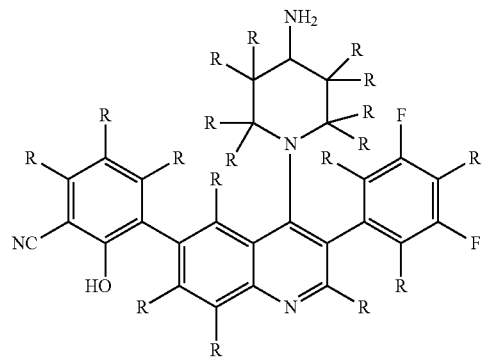

wherein,
each R is independently selected from hydrogen or deutrium,
or a pharmaceutically acceptable salt thereof.

In some embodiments, the pharmaceutically acceptable salt of the compound is an HCl salt. In some embodiments, the pharmaceutically acceptable salt of the compound is a DCl salt.

In some embodiments, the compounds disclosed herein possess one or more stereocenters and each stereocenter exists independently in either the R or S configuration. For example, in some embodiments, the compound disclosed herein exists in the R configuration when one stereocenter is present. In other embodiments, the compound disclosed herein exists in the S configuration when one stereocenter is present. In some embodiments, the compound disclosed herein exists in the RR configuration when two stereocenters are present. In some embodiments, the compound disclosed herein exists in the RS configuration when two stereocenters are present. In some embodiments, the compound disclosed herein exists in the SS configuration when two stereocenters are present. In some embodiments, the compound disclosed herein exists in the SR configuration when two stereocenters are present.

The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds disclosed herein are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers of compounds disclosed herein is carried out using covalent diastereomeric derivatives of the compounds described herein. In another embodiment, diastereomers of compounds disclosed herein are separated by separation/resolution techniques based upon differences in solubility. In other embodiments, separation of steroisomers of compounds disclosed herein is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

Separation of individual enantiomers from a racemic mixture is possible by the use of chiral supercritical fluid chromatography (SFC) or chiral high performance liquid chromatography (HPLC). In some embodiments, enantiomers described herein are separated from each other by the use of chiral SFC or chrial HPLC. In some embodiments, compounds disclosed herein that include one or more chiral centers (e.g. compounds disclosed herein that include the moiety trans-octahydro-1H-pyrido[3,4-b]morpholin-6-yl) are separated into individual enantiomers using chiral SFC or chrial HPLC. A wide variety of conditions and suitable columns are available.

Daicel polysaccharide chiral stationary phases (CSPs) are among the columns used for chiral SFC separations. In some embodiments, Daicel analytical immobilised and coated CHIRALPAK and CHIRALCEL HPLC columns can be used for SFC analysis.

In some embodiments, screening for the suitability of using a SFC column is performed on the four main immobilised phases (CHIRALPAK IA, IB, IC and ID) and the four main coated columns (CHIRALPAK AD and AS and CHIRALCEL OD and OJ), with varying concentrations of organic modifier. A variety of column phases are available, including but not limited to OD and OJ, OX and OZ chlorinated phases, and a range of complementary cellulose based CHIRALCEL phases including OA, OB, OC, OF, OG and OK.

Non-limiting examples of chiral selectors contemplated for use in the separation of enantiomers include amylose tris (3, 5-dimethylphenylcarbamate), cellulose tris (3, 5-dimethylphenylcarbamate), cellulose tris (3, 5-dichlorophenylcarbamate), amylose tris (3-chlorophenylcarbamate), amylose tris (3, 5-dichlorophenylcarbamate), amylose tris (3-chloro, 4-methylphenylcarbamate), amylose tris ((S)-alpha-methylbenzylcarbamate), amylose tris (5-chloro-2-methylphenylcarbamate), cellulose tris (4-methylbenzoate), cellulose tris (4-chloro-3-methylphenylcarbamate), and cellulose tris (3-chloro-4-methylphenylcarbamate).

Non-limiting examples of chiral columns contemplated for use in the separation of enantiomers include CHIRALPAK IA SFC, CHIRALPAK AD-H SFC, CHIRALPAK IB SFC, CHIRALCEL OD-H SFC, CHIRALPAK IC SFC, CHIRALPAK ID SFC, CHIRALPAK IE SFC, CHIRALPAK IF SFC, CHIRALPAK AZ-H SFC, CHIRALPAK AS-H SFC, CHIRALPAK AY-H SFC, CHIRALCEL OJ-H SFC, CHIRALCEL OX-H SFC, and CHIRALCEL OZ-H SFC.

In some embodiments, the identity of and placement of substituents on the compounds described herein help to minimize undesired activity. For example, in some embodiments undesired activity includes undesired hERG inhibition. In some embodiments, the presence of a hydroxyl group and an adjacent cyano group on an aromatic ring reduces undesired hERG inhibition significantly as compared to the lack of both groups, the presence of a hydroxyl group without an adjacent cyano group, or the presence of a cyano group without an adjacent hydroxyl group. For example, in some embodiments significant reduction of undesired hERG inhibition is observed when $R^B$ is a substituted or unsubstituted 2-hydroxy-3-cyanophenyl.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "halo" or, alternatively, "halogen" or "halide" means fluoro, chloro, bromo or iodo. In some embodiments, halo is fluoro, chloro, or bromo.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound disclosed herein, or a pharmaceutically acceptable salt thereof, and a co-agent, are both administered to a patient simultaneously in the form of a single entity or dosage. The term "non-fixed combination" means that the active ingredients, e.g. a compound disclosed herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds disclosed herein, or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound disclosed herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound disclosed herein, or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound disclosed herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound disclosed herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound disclosed herein, or a pharmaceutically acceptable salt thereof, is co-administered with a second therapeutic agent, wherein the compound disclosed herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds disclosed herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

Abbreviations

BINAP: (2,2'-bis(diphenylphosphino)-1,1'-binaphthyl);
DCE: 1,2-dichloroethane;
DCM: dichloromethane;
DI: deionized;
DIEA or DIPEA: diisopropylethylamine;
EtOAc: ethyl acetate;
EtOH: ethanol;
equiv: equivalents, typically molar equivalents;
HATU: 1-[bis(dimethylamino)methylene]-1H-1,2,3-triazolo[4,5-b]pyridinium 3-oxid hexafluorophosphate;
IPA: isopropylalcohol;
IPAc: isopropyl acetate;
MeOAc: methyl acetate;
NBS: N-bromosuccinimide;
NCS: N-chlorosuccinimide;
OPA: orthophosphoric acid;
PTS: p-toluene sulfonic acid;
Pd(Amphos)Cl$_2$: bis(di-tert-butyl(4-dimethylaminophenyl)phosphine)dichloropalladium(II);
Pd$_2$dba$_3$: tris(dibenzylideneacetone)dipalladium(0);
Pd(dppf)Cl$_2$: [1,1'-bis(diphenylphosphino)ferrocene]dichloropalladium(II);
(pinB)$_2$: bis(pinacolato)diboron;
rt or RT: room temperature;
Rt: retention time;
SFC: supercritical fluid chromatography;
SST: somatostatin;
SSTR: somatostatin receptor;
TEA: trimethylamine;
TFA: trifluoroacetic acid;
THF: tetrahydrofuran;
vol: volume, typically used for reaction volume or ratio of solvents;
Xphos: 2-dicyclohexylphosphino-2',4',6'-triisopropylbiphenyl;
hrs: hours;
h or hr: hour.

The following examples are provided for illustrative purposes only and not to limit the scope of the claims provided herein.

Example 1: Synthesis of 3-Bromo-2-(methoxymethoxy)benzonitrile (Compound 2b)

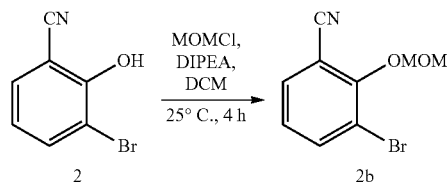

Diisoproylethylamine (114 mL, 1.3 equiv) was slowly added to a solution of nitrile Compound 2 (100 g, 1 equiv) in CH$_2$Cl$_2$ (1 L, 10 vol) at 0° C. and stirred for 30 min. Chloromethyl methyl ether (MOMCl) (46 mL, 1.2 equiv) was then added slowly while maintaining the internal temperature at 0 to 5° C. The reaction was then allowed to warm to RT and stirred for 4 h, until TLC showed complete reaction. The reaction was cooled to 0° C. and quenched with DI-water (300 mL, 3 vol) and the layers were separated. The aqueous layer was extracted with CH$_2$Cl$_2$ (300 mL, 3 vol) and the combined organic layer was washed with water and brine, concentrated on a rotavap to afford 115 g of crude product as a brown oil. The crude product was purified on a plug of SiO2 and eluted with 10% ethyl acetate and pet-ether (20 vol). Only one fraction was collected, evaporated under vacuum, and dried under high vacuum to afford 86 g (70%) of Compound 2b as colorless oil, which was 99.96% pure (HPLC-AUC).

Example 2: Synthesis of (3-cyano-2-hydroxyphenyl)boronic Acid (Compound 1a)

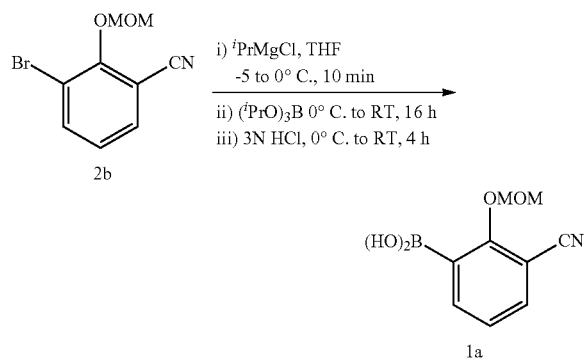

A solution of $^i$PrMgCl in THF (2 M in THF, 340 mL, 2.2 equiv) was added slowly to a solution of Compound 2b (75 g, 1 equiv) in THF (1.12 L, 15 vol) while maintaining the internal temperature at −5 to 5° C. and stirred for 10 min. Triisopropyl borate (180 mL, 2.5 equiv) was then added while maintaining the internal temperature at −5 to 3° C. The reaction was then allowed to warm to room temperature and stirred for 18 h until TLC showed complete reaction. The reaction was then cooled to −10° C. and quenched by slow addition of 3N HCl (620 mL, 6 equiv) at −10° C. The mixture was stirred for 3 h at RT and extracted with ethyl acetate (525 ml, 5 vol) and the aqueous layer was extracted with ethyl acetate (225 mL, 3 vol). The combined organic layer was successively washed with DI-water (3×3 vol), brine (525 mL, 3 vol) and concentrated under vacuum to afford the crude material as a gummy solid. The crude was stirred in pet-ether (525 mL, 5 vol) for 30 min and resulting solids were filtered, washed with pet-ether (150 mL, 2 vol) and dried under vacuum to afford 35 g (70%) of boronic acid Compound 1a as an off white solid, which was 97.91% pure (HPLC-AUC).

Example 3: Synthesis of 2-Bromo-6-cyanophenyl acetate (Compound 2c)

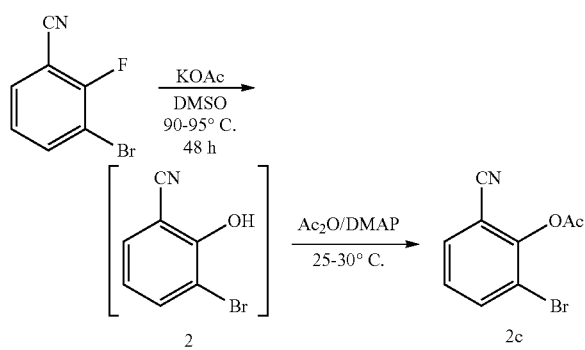

3-Bromo-2-fluro-benzonitrile (25 g, 1.0 equiv), potassium acetate (5 equiv) was mixed in DMSO (7 vol) and heated to 90-95° C. for 48 h. IPC showed 0.38% of 3-bromo-2-fluro-benzonitrile and 96.5% of Compound 2. Reaction mixture was cooled to 25-30° C. and quenched with purified water (25 vol water). Then pH was adjusted pH to 3-4 using 6N HCl solution. The obtained resulting mixture was diluted with MTBE (10 vol). The organic layer was separated, and aqueous layer was extracted with 10 vol MTBE. Combined organic layers were washed with water (10 vol×3) and concentrated to 2 vol level, chased with DCM (3 vol) and concentrated down to 2 vol again before diluted with DCM (8 vol) to afford crude solution of Compound 2. This solution was used in the subsequent process without further purification.

Crude solution of Compound 2 was mixed with acetic anhydride (1.3 equiv), DMAP (0.1 equiv) at 25-30 C for 2 h with stirring. IPC showed 0.8% Compound 2 and 94.8% Compound 2c. Reaction mass was diluted with purified water (10 vol), stirred for 30 mins. Organic layer was separated. Aqueous layer was extracted with 2 vol DCM. The combined organic layer was washed with water (8 vol×2). Charcoal (10%) was added to organic layer and stirred for 1 h before filtered through celite bed. The filtrate was then concentrated to 2 vol level, chased with 3 vol and 2 vol of n-heptane subsequently before cooled to RT and stirred for 1 hr at 5-10° C. The product was isolated via filtration as solid (25.5 g, 85% yield over two steps, HPLC purity 96.8%).

Example 4: Alternative Synthesis of 2-hydroxy-3-cyano-potassium phenyltrifluoro borate (Compound 1c)

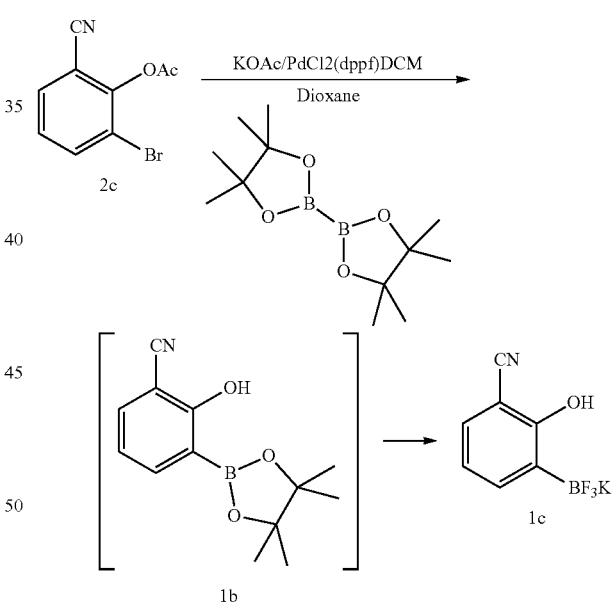

Compound 2c (20 g, 1.0 equiv) was mixed with KOAc (3.0 equiv), bis(pinacolato)diboron (1.2 equiv) in 2-methyl-THF. The mixture was stirred and degassed with $N_2$ bubbling before addition of Pd(dppf)Cl$_2$.DCM (0.025 equiv). The resulting mixture was heated to 80-85° C. for 16 h. IPC showed 0.3% of starting material and 92% Compound 1b. Reaction mixture was cooled to 25-30° C. and filtered through celite pad. The celite pad was washed with MTBE (5 vol). The combined filtrate was concentrated to 2 vol and chased with MTBE to 2 vol. The resulting solution was diluted with MTBE (10 vol) and stirred for 1 h at ambient temperature. The suspension was again filtered through celite pad and the celite pad was rinsed with MTBE. The combined filtrate was washed with water (500 ml, 5 vol). The aqueous layer was extracted with MTBE. Combined organic layers were washed with 5% N-Acetyl-L-cysteine solution twice (each time 300 ml, 3 vol) and water (300 ml, 3 vol). Then the organic layer was separated, treated with 10% active charcoal, filtered through celite pad. The celite pad was rinsed with MTBE. The combined filtrate was concentrated to 2 vol level, chased with methanol twice (2×4 vol) to 3 vol, and cooled to ambient temperature before used in the next step.

Compound 1b solution was added with KHF$_2$ (5.0 equiv), purified water (2.6 vol), and MeOH (1 vol) before heated to 65° C. for 1 h. The reaction mixture was diluted with MTBE (15 vol) before cooled to 10±5 OC. The resulting suspension was stirred for 1 h before filtration. The solid was transferred to reaction flask, added with 20 vol acetone, stirred at 25±5° C. for 1 h, treated with 10% charcoal, and stirred for another 1 h. The resulting reaction mixture was then filtered through celite pad. Filtrate was concentrated to 2 vol level, chased with MTBE (3 vol×2), concentrate to 2 vol level, and diluted with MTBE (4 vol). The suspension was stirred for 1 h at 25±5° C. before filtered to afford the desired product Compound 1c as off-white solid (11.5 g, 49.5%, HPLC purity 97.8%). $^1$H NMR (400 MHz, DMSO-d$_6$): δ 8.2 (s, 1H), 7.41 (m, 1H), 7.34 (m, 1H), 6.80 (m, 1H); $^{13}$C NMR (100 MHz, DMSO-d$_6$): 161.8, 138.0, 138.0, 130.8, 119.4, 118.0, 96.6.

Example 5: Synthesis of 6-Bromo-3-chloroquinolin-4-ol (A-II)

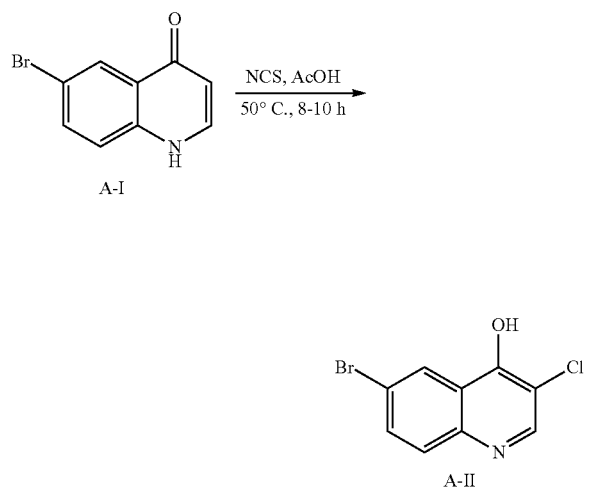

N-Chlorosuccinimide (377 g, 1.05 equiv) was added to a suspension of 6-bromoquinolin-4(1H)-one (Compound A-I, 600 g, 1 equiv) in acetic acid (12 L, 20 vol) at RT. The reaction was then heated to 50° C. and stirred for 8 h. The reaction was cooled to 20° C., filtered, successively washed with AcOH (1.8 L, 3 vol), water (2.4 L, 4 vol), and MTBE (1.2 L, 2 vol), and dried under vacuum on a filter to afford crude Compound A-II. The crude material was stirred in MTBE (7.2 L, 12 vol) for 2 h, filtered, washed with MTBE (0.6 L, 1 vol) and dried under vacuum to afford 541 g (78%) of Compound A-II as an off white solid, which was determined to be 97.35% pure (HPLC-AUC).

Example 6: Synthesis of 4,6-Dibromo-3-chloroquinoline (A-III)

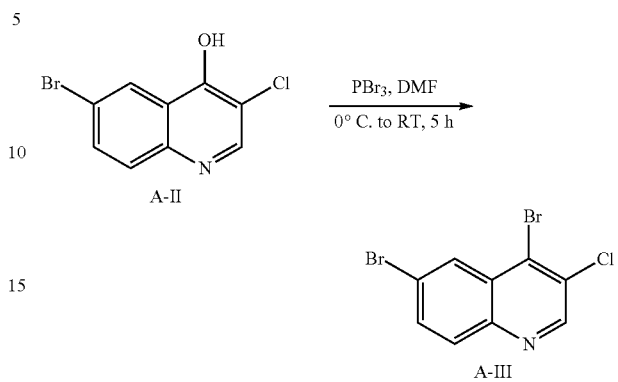

Phosphorus tribromide (317 mL, 1.6 equiv) was slowly added to a solution of A-II (540 g, 1 equiv) in DMF (7 L, 13 vol) at 0-5° C. The reaction was allowed to warm to RT and stirred for 4 h. The reaction was cooled to 0° C. and quenched by sat. aqueous solution of NaHCO$_3$ to pH~8 (10.8 L, 20 vol) and diluted with water (5.4 L, 10 vol). The mixture was stirred for 2 h at RT and the solids were filtered, washed with water (2.7 L, 5 vol), and dried on the filter under vacuum. The wet cake was slurried in water (5.4 L, 10 vol) for 2 h and filtered, washed with water (980 mL, 2 vol) and dried on the filter under vacuum to afford crude Compound A-III as a solid. The crude material was stirred in MTBE (2.7 L, 5 vol) for 2 h, filtered, washed with MTBE (980 mL, 2 vol) and dried under vacuum to afford 434 g (65%) of Compound A-III as an off white solid, which was determined to be 97.95% pure (HPLC-AUC).

Example 7: Synthesis of tert-Butyl (1-(6-bromo-3-chloroquinolin-4-yl)piperidin-4-yl)carbamate (A-IV)

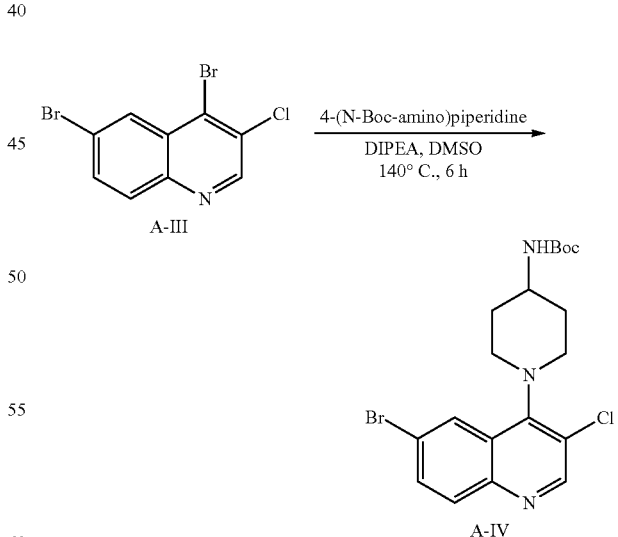

Diisopropylethylamine (932 mL, 4 equiv) and 4-(N-Boc-amino)piperidine (430 g, 1.6 equiv) were successively added to a solution of Compound A-III (430 g, 1 equiv) in DMSO (4.3 L, 10 vol) at RT. The suspension was then heated to 140° C. and stirred for 3 h. The reaction was allowed to cool to RT, diluted with water (12.9 L, 30 vol), and stirred for 2 h. The resulting solids were filtered and dried on a filter. The wet cake was dissolved in DCM (3 L, 7 vol), and the aqueous layer was extracted with DCM (860 mL, 2 vol). The combined organic layer was washed with water (2×2.1 L, 5 vol each), brine (2.1 L, 5 vol), and dried under vacuum to afford crude Compound A-IV as a solid. The crude material was stirred in MTBE (2.21 L, 5 vol) for 1 h, filtered, washed with MTBE (860 mL, 2 vol), and dried under vacuum to afford 412 g (70%) of Compound A-IV as an off-white solid, which was determined to be 98.26% pure (HPLC-AUC).

Example 8: Alternative Synthesis of tert-Butyl (1-(6-bromo-3-chloroquinolin-4-yl)piperidin-4-yl)carbamate (A-IV)

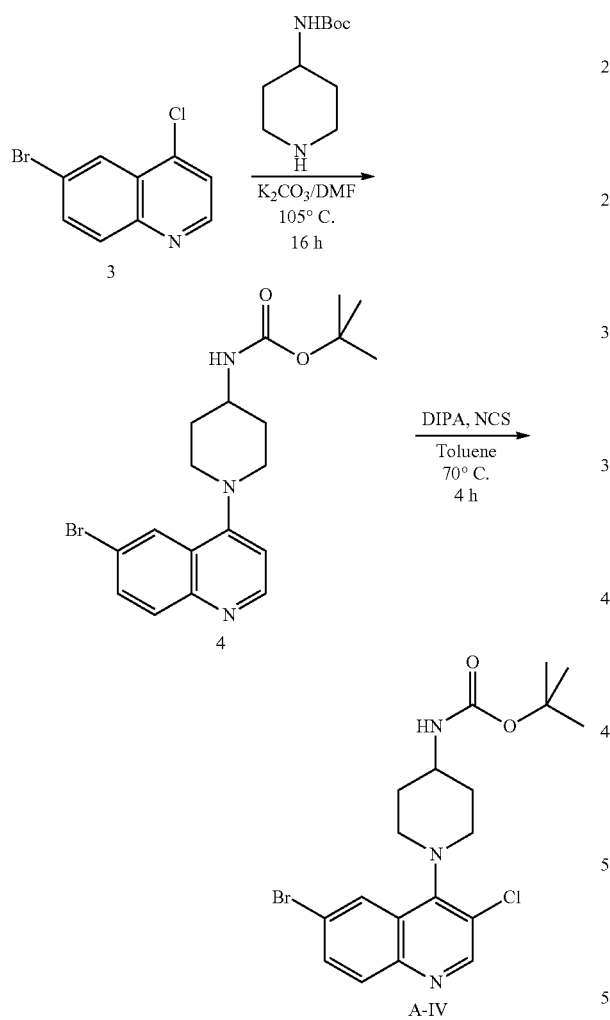

A mixture of 6-bromo-4-chloro-quinoline (25 g, 1.0 equiv), DMF (6.0 vol), 4-(tert-butoxy carbonylamino)piperidine (2.0 equiv), K$_2$CO$_3$ (2.5 equiv), was stirred and heated to 105° C. for 16 h. Reaction was monitored by IPC-HPLC and showed 93.5% of Compound 4 and 0.12% of Compound 3. Then reaction mixture was cooled to 25-30° C., added with purified water (30 vol), and stirred for 2 h. Solid was filtered and washed with purified water. The crude solid was slurred with n-heptane (5 vol), filtered, and washed with n-heptane (2 vol). The solid was dried at 55° C.

provided desired product Compound 4 (35.3 g, 84% yield). $^1$H NMR (400 MHz, DMSO-d$_6$): δ 8.69 (d, 1H), 8.02 (d, 1H), 7.88 (m, 1H), 7.80 (m, 1H), 7.02 (d, 1H), 6.97 (d, 1H), 3.44 (m, 3H), 2.87 (m, 2H), 1.94 (d, 2H), 1.68 (m, 2H), 1.38 (s, 9H).

Compound 4 (25 g, 1 equiv), DIPA (0.078 equiv), NCS (1.5 equiv), Toluene (10 vol) were mixed and heated at 70° C. for 4 h. Reaction mixture was concentrated to 3 vol level at 45±5° C., cooled to rt, diluted with MTBE (10 vol), washed with purified water (10 vol). After layer separation, aqueous layer was extracted with MTBE (5.0 vol). Combined organic layers were washed with purified water twice (2×5 vol) followed by brine. The organic layer was dried over sodium sulfate, concentrated to 2 vol level, chase with MTBE twice (2×2 vol). Then it was cooled and added with MTBE (1 vol) before warmed to 50±5° C. and stirred for 1 hour. The resulting suspension was cooled to 5±5° C. and stirred for 1 h. Solid was collected by filtration and washed with pre-cooled MTBE (1 vol). Above solid was taken in MTBE (2 vol) and heated to 55±5° C. again, stirred for 1 h, cooled to 5±5° C., and stirred for another 1 h. Solid was collected by filtration and washed with pre-cooled MTBE (1 vol). The collected solid was dried under reduced pressure at 45±5° C. for 8 h to provide product Compound A-IV with 98.9% HPLC purity and 66% (18 g) isolated yield. $^1$H NMR (400 MHz, DMSO-d$_6$): δ 8.65 (s, 1H), 8.25 (d, 1H), 7.92 (m, 1H), 7.73 (m, 1H), 3.76 (s, 1H), 3.51 (m, 2H), 3.37 (d, 2H), 2.14 (d, 2H), 1.69 (m, 2H), 1.46 (s, 9H).

Example 9: Synthesis of tert-Butyl (1-(6-(3-cyano-2-hydroxyphenyl)-3-(3,5-difluorophenyl)quinolin-4-yl)piperidin-4-yl)carbamate (A-VI)

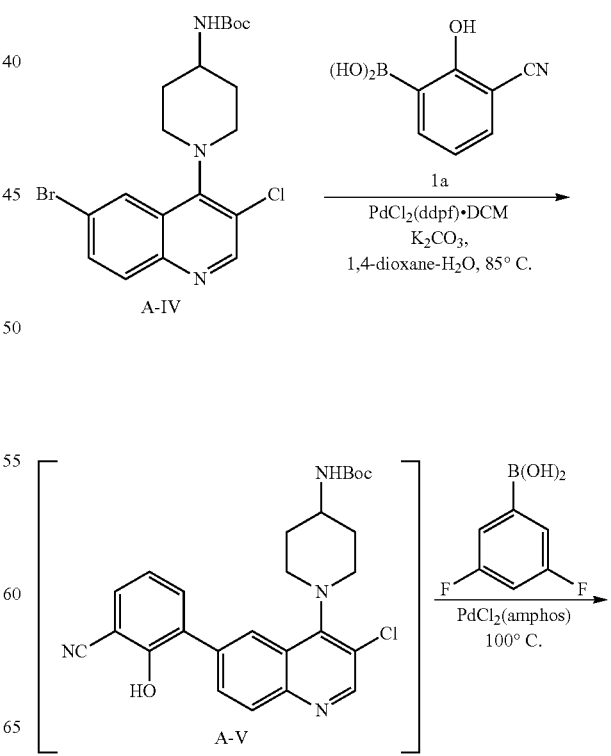

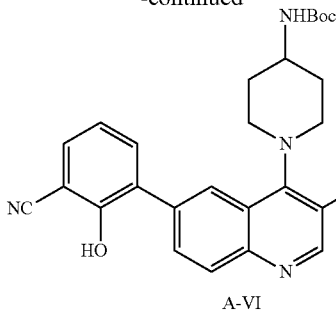

A-VI

Quinoline A-IV (350 g, 1 equiv), (3-cyano-2-hydroxyphenyl)boronic Acid (Compound 1a) (155 g, 1.2 equiv), and K$_2$CO$_3$ (438 g, 4 equiv) were charged to the round bottomed flask. 1,4-Dioxane (3.5 L, 10 vol) and DI-water (350 mL, 1 vol) were added to the flask and the resulting reaction mixture was degassed with argon for 30 min. PdCl$_2$(dppf).CH$_2$Cl$_2$ (32.5 g, 0.05 equiv) was added to the reaction under argon and the mixture was degassed further for 10 min. The reaction was stirred at 80-85° C. and monitored by TLC and HPLC. After complete reaction (6 h), it was allowed to cool to 25-30° C. and 3,5-difluorophenylboronic acid (346 g, 3 equiv) was added to the reaction mixture which was then degassed with argon for 10 min. PdCl$_2$(amphos) (25.9 g, 0.05 equiv) was added to the flask under argon atmosphere and the reaction mixture was degassed further for 10 min. The reaction was then heated to 90-100° C. and stirred for 19 h (monitored by TLC and HPLC). HPLC showed 82.04% of Compound A-VI along with 1.95% of un-reacted Compound A-V and 0.94% of another impurity at 8.2 min. The reaction was allowed to cool to 25-30° C. and filtered through a pad of Celite and washed with ethyl acetate (1350 mL, 3 vol). The filtrate was concentrated under vacuum until ~10% solvent remained and the resulting residue was diluted with ethyl acetate (6.3 L, 18 vol), washed with water (2×3.5 L, 10 vol each), brine (3.5 L, 10 vol), and dried over anhydrous Na$_2$SO$_4$. The organic layer was concentrated under vacuum to dryness and was then slurried in ethyl acetate (2.1 L, 6 vol) for 4 h at RT (after 2.5 h of stirring at RT, free solid formation was observed). Resulting free solids were filtered, washed with ethyl acetate (700 mL, 2 vol) and dried under vacuum until constant weight to afford 200 g (45%) of Compound A-VI as an off white solid, which was 98.4% pure (HPLC-AUC) with approx. 3500 ppm of trace Palladium.

Example 10: Alternative Synthesis of tert-Butyl (1-(6-(3-cyano-2-hydroxyphenyl)-3-(3,5-difluorophenyl)quinolin-4-yl)piperidin-4-yl)carbamate (A-VI)

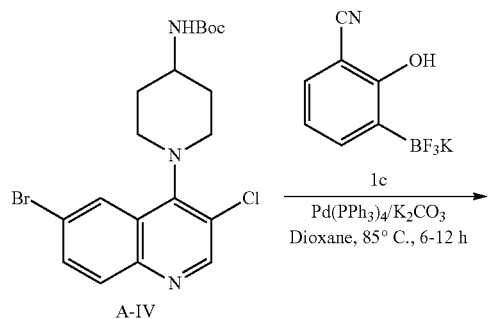

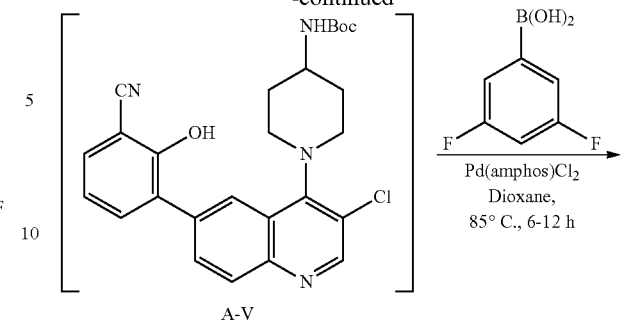

Compound A-IV (25.0 g, 1 equiv), Compound 1c (1.2 equiv), K$_2$CO$_3$ (3.0 equiv), 1,4-dioxane (9 vol), and purified water (0.75 vol) was added to the reaction flask. The mixture was degassed with N$_2$ bubbling before addition of Pd(PPh$_3$)$_4$ (0.017 equiv). Then the reaction mixture was heated to 80-85° C. for 12 h. IPC at 12 h showed <1% of Compound A-IV. Then 3,5 diflurophenylboronic acid (2.0 equiv), Pd(amphos)Cl$_2$ (0.03 equiv) was added and the reaction mixture was degassed again before heated up to at 90-95° C. for 6 h. IPC showed <2% of remaining Compound A-V. Pure Compound A-V sample was isolated and characterized by $^1$H NMR (400 MHz, DMSO-d$_6$): δ 8.63 (s, 1H), 8.27 (bs, 1H), 7.94 (m, 2H), 7.53 (d, 1H, J=7.2 Hz), 7.47 (d, 1H, J=6.0 Hz), 6.99 (d, 1H, J=7.6 Hz), 6.77 (bs, 1H), 3.50 (m, 1H), 3.41 (m, 2H), 3.34 (m, 2H), 1.87 (m, 2H), 1.65 (m, 2H), 1.39 (s, 9H).

Workup and Pd Removal:

The reaction mixture was cooled to 25-30° C., filtered through celite pad. The celite pad was washed with IPAc (2.0 vol). The filtrate was combined, concentrated to 3 vol, chased with IPAc (5 vol) twice to 4 vol. The resulting solution was diluted with IPAc (8 vol) and washed with water (2×10 vol). Organic layer was separated and washed with 1% N-Acetyl L-cysteine (2×10 vol) before concentrated to 6 vol. The resulting suspension was stirred at reflux for 2 h and cooled to ambient temperature. The suspension is further cooled to 10±5° C., stirred for 2 h, and filtered. The filter cake was washed with 1 vol IPAc and dried to provide the desired crude product as pale-yellow solid.

Isolated Compound A-VI crude solid was dissolved in 2-methylTHF (15 vol), added with SILIAMET S THIOL (0.25% w/w), and stirred at ambient temperature for 3 h. The suspension was filtered through celite bed, washed with 2-methylTHF (2 vol). The above process was repeated again. The final filtrate was concentrated to 2 vol, chased with n-heptane twice (2×3 vol). The resultant suspension was filtered. The solid was dried under vacuum at 45±5° C. to afford the purified Compound A-VI as solid (HPLC purity 96% with Pd level of 13 ppm).

Example 11: Additional Purification of A-VI

Compound A-VI (200 g, 98.40% pure) was taken in IPAc (1 L, 5 vol) and refluxed for 1 h. The mixture was then allowed to cool to RT and then cooled to 15° C., filtered, washed with IPAc (600 mL, 3 vol), and dried to afford 170 g of Compound A-VI as an off white solid, which was 98.71% pure (HPLC-AUC) with approx. 50 ppm of trace Palladium.

Example 12: Removal of Residual Palladium from A-VI

Compound A-VI (150 g, 98.71% pure) was dissolved in THF (3.4 L, 20 vol). Si-Thiol (240 g) was added and the solution stirred overnight at RT. The mixture was filtered through a Celite bed, washed with THF (510 mL, 3 vol), and concentrated under vacuum to afford a solid. The crude solid was then diluted with IPAc (1 L, 5 vol) and the slurry was refluxed for 2 h. The mixture was then allowed to cool to RT, then was cooled to 15° C., filtered, washed with IPAc (510 mL, 3 vol), and dried to afford 150 g of Compound A-VI as an off-white solid, which was 100% pure (HPLC-AUC) with no detectable residual Palladium.

Example 13: 3-(4-(4-Amino-piperidin-1-yl)-3-(3,5-difluoro-phenyl)-quinolin-6-yl)-2-hydroxy-benzonitrile, di-HCl Salt (Compound A-2HCl)

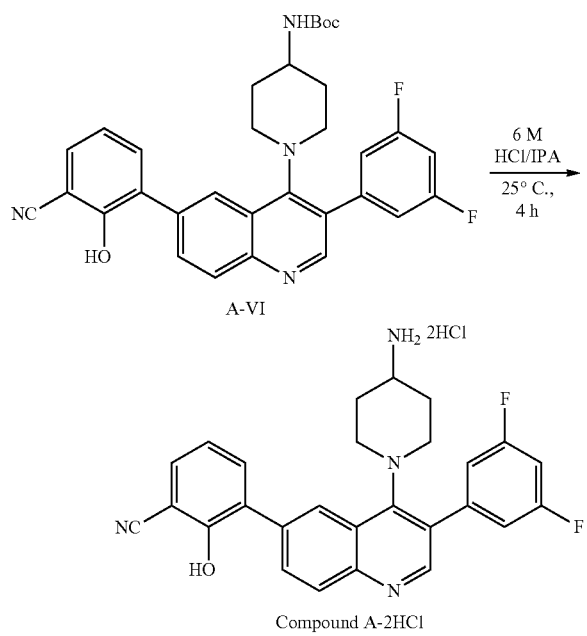

A suspension of Compound A-VI (150 g, 269.5 mmol) in 6M HCl-IPA (1.45 L, 10 vol) was stirred at RT for 4 h. TLC showed complete reaction (thick suspension observed). The reaction was diluted with MTBE (2.17 L, 15 vol), stirred for 2 h, and the resulting solids were filtered, washed with MTBE (290 mL, 2 vol) and dried under vacuum to afford 130 g (91%) of Compound A-2HCl salt as a pale yellow solid, which was 100% pure (HPLC-AUC), with no detectable residual palladium. Chloride titration showed 15.8 wt % of chloride.

Example 14: 3-(4-(4-Amino-piperidin-1-yl)-3-(3,5-difluoro-phenyl)-quinolin-6-yl)-2-hydroxy-benzonitrile, HCl Salt (Compound A-HCl)

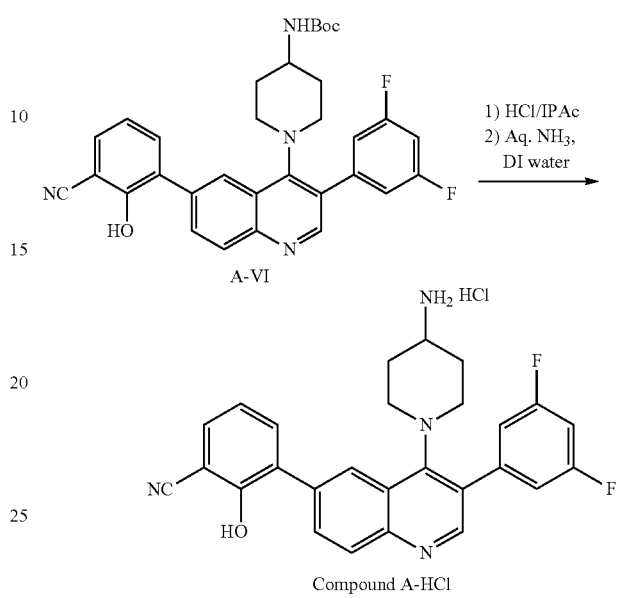

A suspension of Compound A-VI (120.0 g) in IPAc (5 vol) was added with 6M HCl in isopropyl acetate (10 vol) at rt. The resulting mixture was stirred for 2 h at rt. After completion of the reaction (Compound A-VI content was found to be <1.0% by HPLC), the thick suspension was diluted with IPAc (0.6 L, 5 vol), stirred for 1 h and filtered. The filter cake was washed with IPAc (240.0 mL, 2 vol) and suck dried under vacuum for 2 h to afford Compound A-2HCl as a yellow solid. Crude Yield: 110.0 g (96%)

The solution of Compound A-2HCl (110.0 g) in purified water (18 vol) was heated to 45±5° C. before aq. NH₃ (25%, 2.4 equiv) was slowly added and stirred for 1 h at 45±5° C. The pH of the final reaction mixture was 5-5.5. Then, purified water (550.0 mL, 5 vol) was added slowly at same temperature over 2 h. The resulting suspension was cooled to rt then to 10±5° C. and stirred for 1 h. The mixture was filtered and washed with cold purified water (2 vol) (10±5° C.). The wet cake was suck dried for an hour and dried at 55±5° C. for 24 h under vacuum to afford Compound A-HCl as a bright yellow to gold color solid (88.0 g, 83% isolated yield with 99.4% HPLC purity).

Example 15: Preparation of Compound A-HCl from Compound A-2HCl

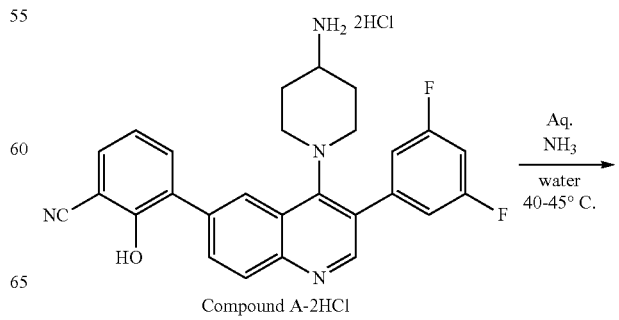

-continued

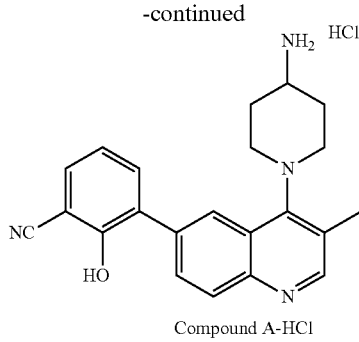

Compound A-HCl

A suspension of Compound A-2HCl (118 g) in DI-water (2.4 L, 20 vol) was stirred at 40-45° C. Aqueous ammonia (25%, 35.4 m, 0.3 mL/g) was slowly added to the hot suspension to adjust pH~5-6 and stirred for 1 h. DI-water (590 mL, 5 vol) was added at same temperature over 2 h and the suspension was allowed to cool to 25° C., then was further cooled to 5-10° C. using ice-water. The free solids were then filtered and washed with DI-water (3×500 mL). The wet cake was dried in a vacuum oven at 55° C. for 18 h to afford constant weight of 101 g (92%) of Compound A-HCl as a pale yellow powder, which was 100% pure (HPLC-AUC), with no detectable residual palladium. Chloride titration showed 8.1 wt % of chloride.

Example 16: Alternate Preparation of Compound A-HCl from Compound A-2HCl

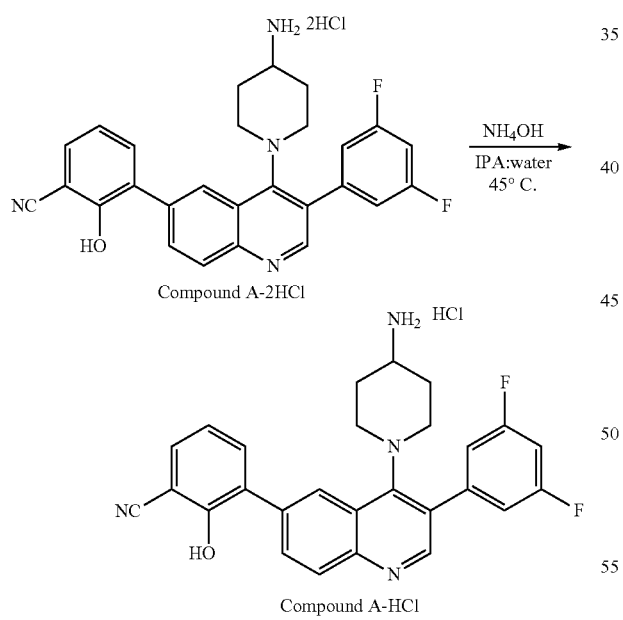

Compound A-2HCl $\xrightarrow[\text{45° C.}]{\text{NH}_4\text{OH} \atop \text{IPA:water}}$ Compound A-HCl A suspension of Compound A-2HCl (2.1 g) in 1:1 IPA:water (10 mL, 5 vol) was stirred at 45° C. Concentrated ammonium hydroxide (28-30%, 0.8 equiv) was slowly added and the hot suspension was stirred for 1 h. DI-water (20 mL, 10 vol) was added at same temperature over 2 h and the suspension was cooled to 10° C. over 2 h. The resulting flowable slurry was then filtered and washed with 15:85 IPA:water (2×3 vol). The wet cake was dried under vacuum at 45° C. for 18 h to afford constant weight of 1.42 g (78%) of Compound A-HCl as a pale yellow powder. Chloride titration showed 8.0 wt % of chloride.

Example 17: Alternate Preparation of Compound A-HCl from Compound A-2HCl, without the Use of a Base

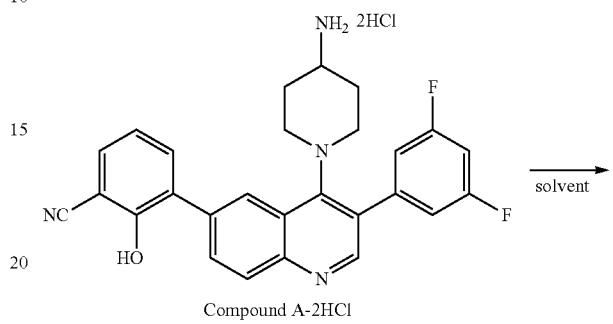

Compound A-2HCl $\xrightarrow{\text{solvent}}$

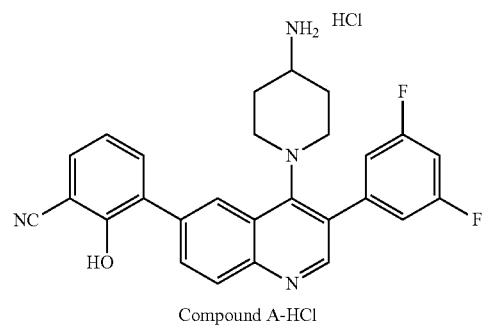

Compound A-HCl

About 80 mg of Compound A-2HCl salt was dissolved in various solvents (see below table). Reactions were heated to 50° C. for 30 minutes, cooled over 2 h to RT, held at RT for 1 h, then the solids were filtered and dried under vacuum at 50° C. Solvent was evaporated to yield Compound A-HCl and the resulting XRPD pattern was evaluated. Each solvent system, except 9:1 methyl acetate:water, resulted in the XRPD pattern as in FIG. 1.

| diHCl salt, mg | Solvent(s) | vol | XRPD pattern |
| --- | --- | --- | --- |
| 79.3 | IPA:water (8:2) | 10 | FIG. 1 |
| 76.7 | IPA:water (7:3) | 10 | FIG. 1 |
| 78.3 | methyl acetate:water (9:1) | 10 | di-HCl |
| 79.4 | methyl acetate:water (8:2) | 10 | FIG. 1 |
| 78.7 | water | 6 | FIG. 1 |
| 79.5 | water | 10 | FIG. 1 |
| 92.7 | water + 0.5 equiv NaHCO$_3$ | 10 | FIG. 1 |

Example 18: Preparation of Compound A from Compound A-2HCl

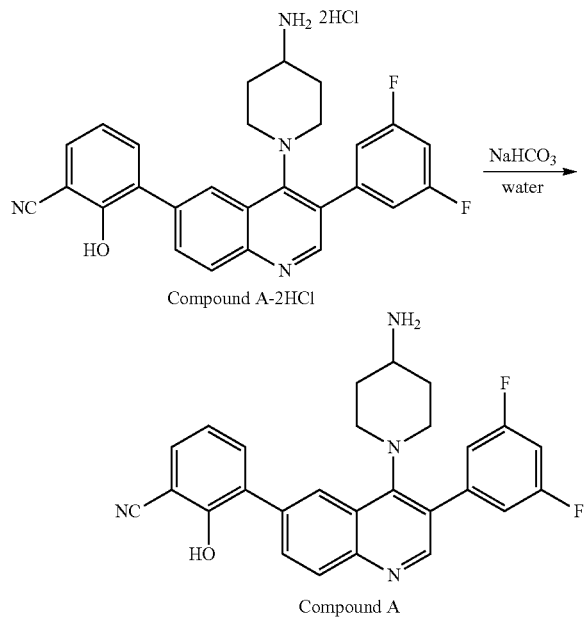

Compound A-2HCl

↓ NaHCO₃, water

Compound A

About 1.2 g of Compound A-2HCl was slurried in 15 volumes of sat. sodium bicarbonate for 30 minutes. The solid was filtered and dried at 40-45° C. under vacuum to yield 730 mg (77%) of Compound A as the free base.

Example 19: Preparation of Compound A-HCl from Compound A

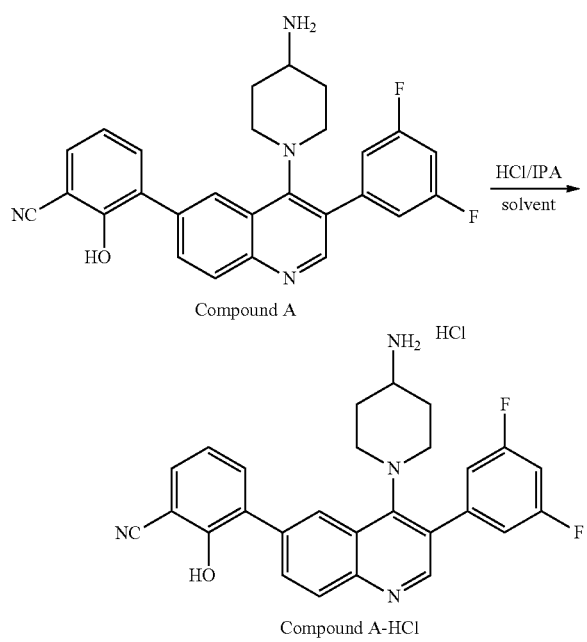

Compound A

↓ HCl/IPA solvent

Compound A-HCl

About 17 mg of Compound A, free base was dissolved in various solvents (500 uL each, see below table) followed by addition of 1.0 equiv of 3M HCl/IPA solution. The solids were filtered to yield Compound A-HCl and the resulting XRPD pattern was evaluated. Each solvent, except MTBE, resulted in the XRPD pattern as in FIG. 1.

| Free Base, mg | HCl/IPA, equiv | Solvent | XRPD pattern |
|---|---|---|---|
| 18.5 | 1 | MeOAc | FIG. 1 |
| 17.9 | 1 | Acetonitrile | FIG. 1 |
| 17.9 | 1 | THF | FIG. 1 |
| 16.1 | 1 | EtOH:water (9:1) | FIG. 1 |
| 17.1 | 1 | Acetone:water (9:1) | FIG. 1 |
| 17.2 | 1 | MTBE | amorphous |

Example 20. X-Ray Powder Diffraction (XRPD)

X-ray Powder diffraction was done using a Rigaku MiniFlex 600. Samples were prepared on Si zero-return wafers. A typical scan is from 2θ of 4 to 30 degrees, with step size 0.05 degrees over five minutes with 40 kV and 15 mA. Typical parameters for XRPD are listed below.

| Parameters for Reflection Mode | |
|---|---|
| X-ray wavelength | Cu Kα1, 1.540598 Å, |
| X-ray tube setting | 40 kV, 15 mA |
| Slit condition | Variable + Fixed Slit System |
| Scan mode | Continuous |
| Scan range (°2TH) | 4-30 |
| Step size (°2TH) | 0.05 |
| Scan speed (°/min) | 5 |

Characterization of Crystalline Compound A-HCl

The X-Ray powder diffraction pattern for Compound A-HCl is displayed in FIG. 1. This XRPD pattern shows a crystalline form of Compound A-HCl. Peaks include the peaks listed in the following table:

| Angle 2-Theta (°) | Rel. Intensity (%) |
|---|---|
| 4.5 | 50 |
| 9.1 | 50 |
| 10.2 | 100 |
| 16.3 | 52 |
| 18.4 | 57 |
| 19.1 | 55 |
| 20.7 | 42 |
| 23.3 | 43 |
| 23.4 | 42 |
| 23.6 | 47 |
| 27.1 | 40 |
| 28.0 | 34 |

Characterization of the Crystalline Compound A-2HCl

The X-Ray powder diffraction pattern for Compound A-2HCl is displayed in FIG. 4. This XRPD pattern shows a crystalline form of Compound A-2HCl. Peaks include the peaks listed in the following table:

| Angle 2-Theta (°) | Rel. Intensity (%) |
|---|---|
| 5.4 | 33 |
| 7.3 | 100 |

Characterization of the Pattern A of Crystalline Compound A

The X-Ray powder diffraction pattern for Pattern A of Compound A is displayed in FIG. 7(a). This XRPD pattern shows a crystalline form of Compound A. Peaks include the peaks listed in the following table:

| Angle 2-Theta (°) | Peak relative intensity, % |
|---|---|
| 9.2 | 100 |
| 12.3 | 35 |
| 14.4 | 31 |
| 24.0 | 29 |

Characterization of the Pattern B of Crystalline Compound A

The X-Ray powder diffraction pattern for Pattern B of Compound A is displayed in FIG. 7(b). This XRPD pattern shows a crystalline form of Compound A. Peaks include the peaks listed in the following table:

| Angle 2-Theta (°) | Peak relative intensity, % |
|---|---|
| 5.9 | 34 |
| 13.9 | 22 |
| 14.2 | 20 |
| 17.5 | 100 |
| 24.6 | 30 |

Characterization of the Pattern C of Crystalline Compound A

The X-Ray powder diffraction pattern for Pattern C of Compound A is displayed in FIG. 7(c). This XRPD pattern shows a crystalline form of Compound A. Peaks include the peaks listed in the following table:

| Angle 2-Theta (°) | Peak relative intensity, % |
|---|---|
| 7.2 | 41 |
| 8.3 | 100 |
| 10.9 | 26 |
| 12.0 | 77 |

Example 21. Solubility in Water, FaSSGF, and FaSSIF

The salt forms were slurried in water, Fasted State Simulated Gastric Fluid (FaSSGF), and Fasted State Simulated Intestinal Fluid (FaSSIF) at 37° C. for 2 days. Part of the slurry was filtered using a 0.4 uM syringe filter to recover the supernatant for solubility measurement and the rest was filtered to recover the remaining solid for XRPD analysis.

A calibration curve was developed for measuring concentration via HPLC. Compound A was added to a 100 mL volumetric flask and then filled to the volume with HPLC grade ethanol. Table 3 shows the calibration concentration and corresponding AUC. A 30 minute gradient method with Solvent A as water with 0.1% TFA and solvent B as Methanol:Acetonitrile (1:1) was used.

TABLE 3

| Concentration, mg/mL | AUC (at 261 nM) |
|---|---|
| 0.12 | 1096.75 |
| 0.087 | 787.02 |
| 0.034 | 427.95 |
| 0.0063 | 55.46 |
| 0.00013 | 1.99 |

The calibration correlation was used to measure the solubility of the salt forms. From the clear saturated solution, 0.1 mL liquid was transferred into a 10 mL vial and then filled to the volume with methanol. The solution was then directly injected into the HPLC.

Results from the solubility studies are in Table 4.

TABLE 4

| Compound | Water, mg/mL | FaSSGF, mg/mL | FaSSIF, mg/mL |
|---|---|---|---|
| Compound A (free base) | 0.005 | 2.43 | 0.013 |
| Compound A-HCl | 0.83 | 2.12 | 0.01 |
| Compound A-2HCl | 5.63 | 3.69 | 0.011 |

The solubility is clearly a function of pH. It was also found that the compounds remained as an HCl salt in FaSSGF which simulates the stomach fluid.

Example 22: Dynamic Vapor Sorption (DVS)

Dynamic Vapor Sorption (DVS) was done using a DVS Intrinsic 1. The sample is loaded into a sample pan and suspended from a microbalance. A typical sample mass for DVS measurement is 25 mg. Nitrogen gas bubbled through distilled water provides the desired relative humidity.

A typical measurement includes the steps:
1—Equilibrate at 50% RH
2—50% to 2%. (50%, 40%, 30%, 20%, 10% and 2%)
   a. Hold minimum of 5 mins and maximum of 60 minutes at each humidity. The pass criteria is less than 0.002% change
3—2% to 95% (2%, 10%, 20%, 30%, 40%, 50%, 60%, 70%, 80%, 90%, 95%)
   a. Hold minimum of 5 mins and maximum of 60 minutes at each humidity. The pass criteria is less than 0.002% change
4—95% to 2% (95%, 80%, 70%, 60%, 50%, 40%, 30%, 20%, 10%, 2%)
   a. Hold minimum of 5 mins and maximum of 60 minutes at each humidity. The pass criteria is less than 0.002% change
5—2% to 50% (2%, 10%, 20%, 30%, 40%, 50%)
   a. Hold minimum of 5 mins and maximum of 60 minutes at each humidity. The pass criteria is less than 0.002% change As noted below, Compound A-HCl picked up much less moisture than Compound A-2HCl.

Compound A-HCl

Figure 9:
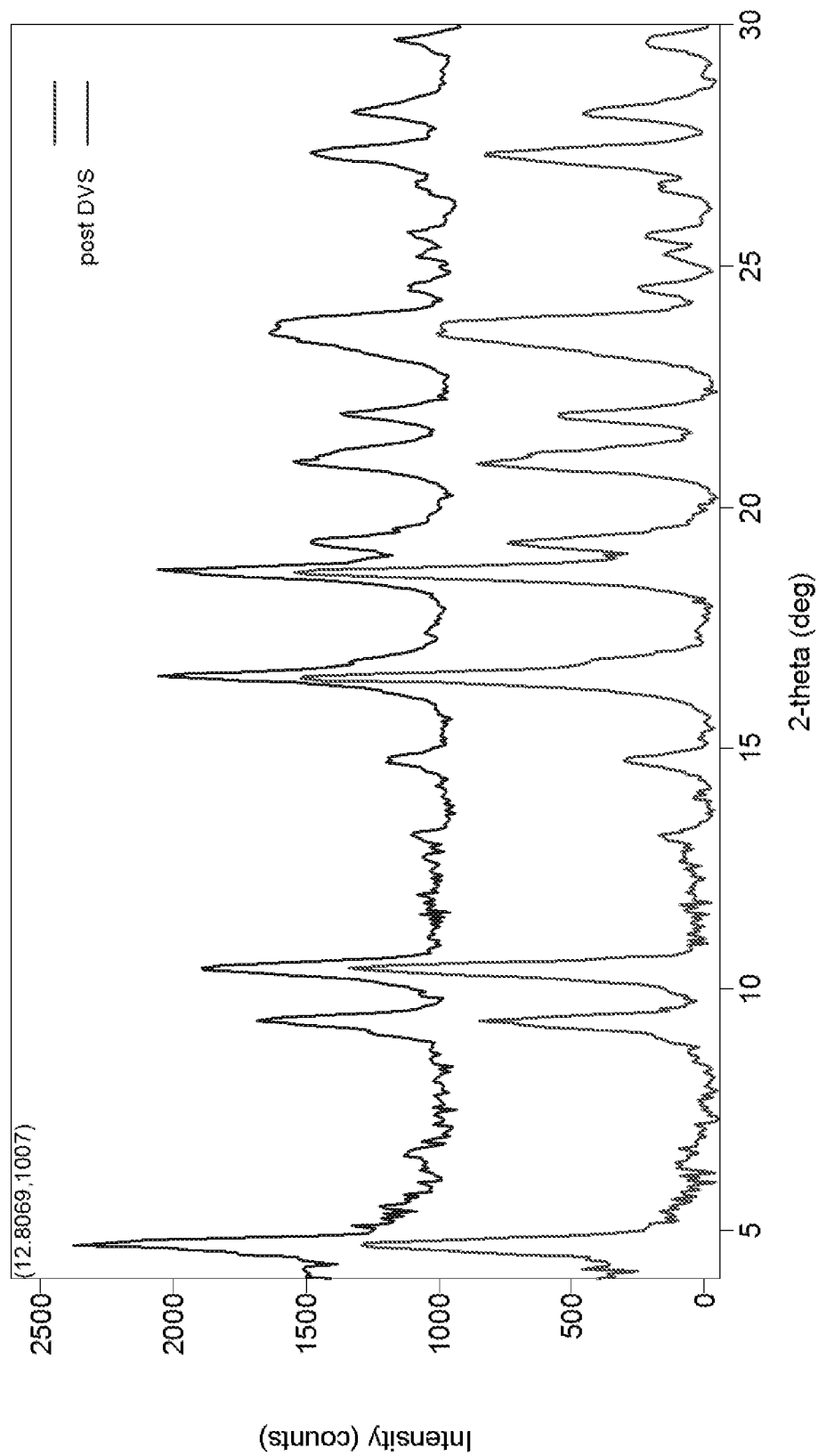
FIG. 9. X-ray powder diffraction (XRPD) pattern of Compound A, mono-HCl salt before (bottom spectra) and after (top spectra) Dynamic Vapor Sorption (DVS) testing between 2 and 95% Relative Humidity (RH).

Testing the mono-HCl salt of Compound A (Compound A-HCl) showed a reversible water uptake (~4.5% w/w) between 2 and 95% RH; and a reversible water uptake (~2.3% w/w) between 15 and 75% RH. The XRPD was unchanged after DVS analysis (FIG. 9).

Compound A-2HCl

Figure 10:
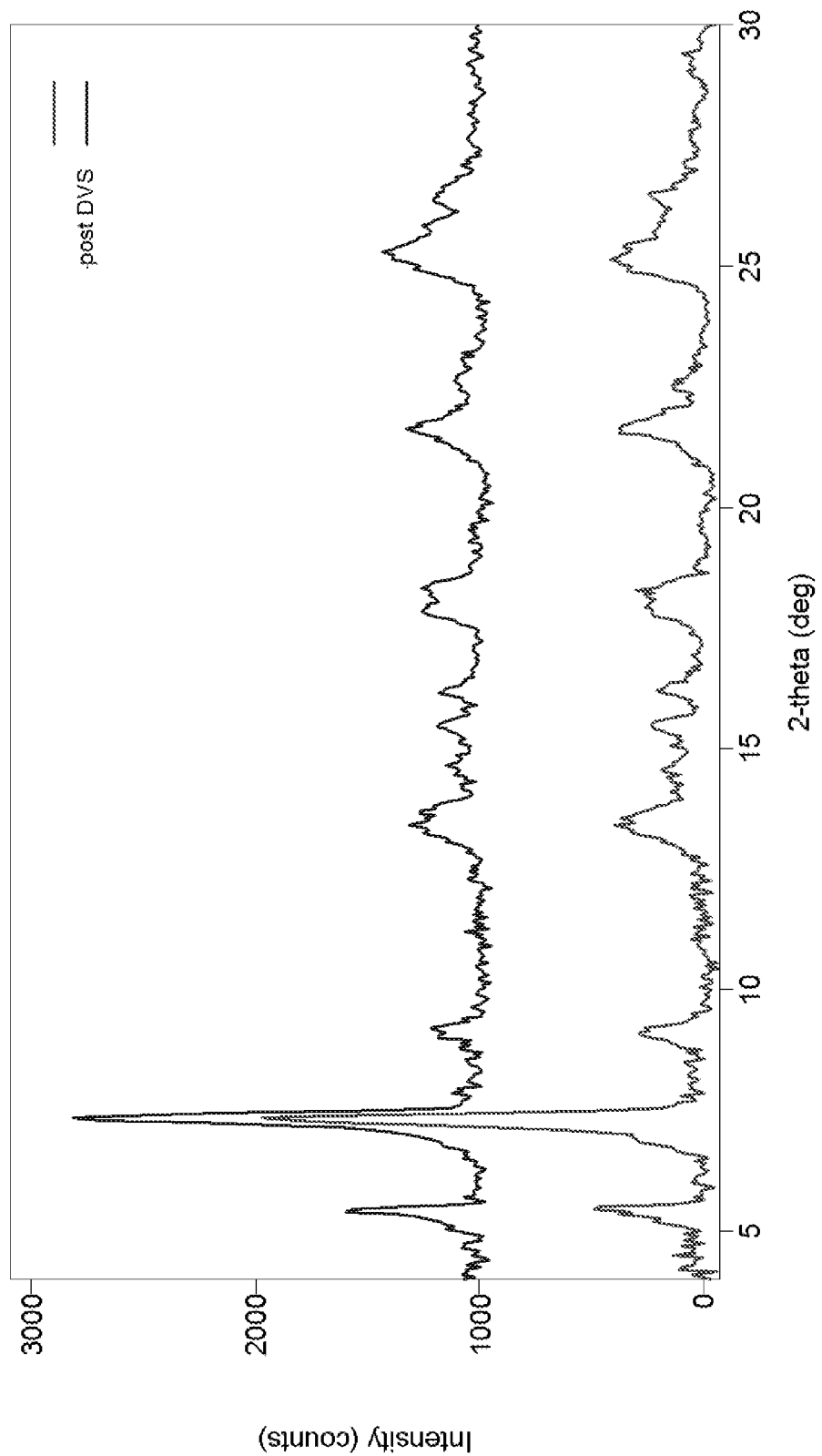
FIG. 10. X-ray powder diffraction (XRPD) pattern of Compound A, di-HCl salt before (bottom spectra) and after (top spectra) Dynamic Vapor Sorption (DVS) testing between 2 and 95% Relative Humidity (RH).

Testing the di-HCl salt of Compound A (Compound A-2HCl) showed a reversible water uptake (~18% w/w) between 2 and 95% RH; and a reversible water uptake (~9% w/w) between 15 and 75% RH. The XRPD was unchanged after DVS analysis (FIG. 10).

Example 23: Thermal Study of Compound A-HCl

Differential Scanning Calorimetry (DSC) was done using a Mettler Toledo DSC3+. Aluminum crucible with cramped pinned lid were used. The heating rates are usually 10° C. per minute from 30 to 250° C.

Thermogravimetric Analysis (TGA) was done using a Mettler Toledo TGA/DSC3+. Aluminum crucible with cramped pinned lid were used. The heating rates are usually 10° C. per minute from 30 to 250° C.

Protective and purge gasses are nitrogen (20-30 mL/min and 50-100 mL/min). Typical parameters for DSC/TGA are listed below.

| Parameters | |
|---|---|
| Method | Ramp |
| Sample size | 5-10 mg |
| Heating rate | 10.0° C./min |
| Temperature range | 30 to 250° C. |

Compound A-HCl

As shown in FIG. 2(a) and FIG. 2(b), Compound A-HCl shows multiple peaks in its thermogram. These peaks were evaluated using thermal analysis and XRPD techniques. Compound A-HCl was heated to various temperatures using TGA/DSC followed by cooling to room temperature and analysis using XRPD. The solid was analyzed by Karl Fischer titration and showed 5.9% water in the sample. The following thermal treatments were performed:

Sample 1: heated the salt to 100° C. and cooled to RT followed by XRPD;
Sample 2: heated the salt to 150° C. and cooled to RT followed by XRPD;
Sample 3: heated the salt to 200° C. and cooled to RT followed by XRPD;
Sample 4: heated the salt to 250° C. and cooled to RT followed by XRPD; and
Sample 5: heated the salt to 295° C. and cooled to RT followed by XRPD.

It was observed that the solid is in tact up to 200° C. and melts at 220° C., at which point the compound loses its chemical and crystal integrity. Therefore, peaks above 220° C. are not relevant.

Since the solid contains about 5.9% water, the initial endothermic peak is due to water loss.

A DSC thermogram for Compound A-2HCl is shown in FIG. 5(a).

A TGA thermogram for Compound A-2HCl is shown in FIG. 5(b).

A DSC thermogram for Pattern C Compound A, free base is shown in FIG. 8(a).

A TGA thermogram for Pattern C Compound A, free base is shown in FIG. 8(b).

Example 24: Infrared (IR) Spectroscopy 200 mg of freshly dried potassium bromide was weighed and transferred into a mortar and was ground into a fine powder. To this, 2.0 mg of test compound was added and the solids were mixed thoroughly. A small quantity of the powder was formed into a thin semi-transparent pellet. A Shimadzu IR Prestige 21 was used to acquire the IR spectra of the test compounds with 60 scans from 4000 cm$^{-1}$ to 400 cm$^{-1}$. Air was used as a reference.

Characterization of the Crystalline Form of Compound A-HCl

The IR spectrum for Compound A-HCl is displayed in FIG. 3. Characteristic peaks include peaks at: 2223 cm$^{-1}$, 1620 cm$^{-1}$, 1595 cm$^{-1}$, 1457 cm$^{-1}$, 1238 cm$^{-1}$, 1220 cm$^{-1}$, and 1117 cm$^{-1}$.

Characterization of the Crystalline Form of Compound A-2HCl

The IR spectrum for Compound A-2HCl is displayed in FIG. 6. Characteristic peaks include peaks at: 2227 cm$^{-1}$, 1620 cm$^{-1}$, 1594 cm$^{-1}$, 1456 cm$^{-1}$, 1439 cm$^{-1}$, 1321 cm$^{-1}$, and 1122 cm$^{-1}$.

Example 25: High-Performance Liquid Chromatography (HPLC) Methods

Method A.

A Hitachi HPLC equipped with DAD detector was used for solubility and purity tests. The HPLC column used was C18 5μ 100A, 4.6 mm×250 mm. Chromatographic conditions were as in the following tables:

| Mobile Phase (A) | 0.1% TFA in 1 L Milli Q water |
|---|---|
| Mobile Phase (B) | Acetonitrile |
| Sample Temperature | 25° C. |
| Flow Rate | 0.8 mL/min |
| Detection Wavelength | 232 nm |
| Injection Volume | 5 uL |
| Run Time | 25 min |
| Injection Delay | 5 min |

| Step | Time (min) | Mobile Phase A (%) | Mobile Phase B (%) |
|---|---|---|---|
| 1 | 0.1 | 98 | 2 |
| 2 | 16 | 2 | 98 |
| 3 | 19 | 2 | 98 |
| 4 | 22 | 98 | 2 |
| 5 | 25 | 98 | 2 |

Method B.

A Waters Alliance HPLC (or equivalent) equipped with DAD detector was used for purity tests. The HPLC column used was C18 5μ 110A, 4.6 mm×250 mm. Chromatographic conditions were as in the following tables:

| Mobile Phase (A) | 0.1% OPA in 1 L Milli Q water |
|---|---|
| Mobile Phase (B) | Acetonitrile |
| Sample Temperature | 25° C. |
| Flow Rate | 1.2 mL/min |
| Detection Wavelength | 232 nm/212 nm |
| Injection Volume | 5 uL |
| Run Time | 25 min |
| Injection Delay | 5 min |

| Step | Time (min) | Mobile Phase A (%) | Mobile Phase B (%) |
|---|---|---|---|
| 1 | 0.1 | 98 | 2 |
| 2 | 0.5 | 98 | 2 |
| 3 | 7 | 2 | 98 |
| 4 | 17 | 2 | 98 |
| 5 | 21 | 98 | 2 |
| 6 | 25 | 98 | 2 |

Example 26: 2-{4-[(4aS,8aS)-Octahydro-1H-pyrido[3,4-b][1,4]oxazin-6-yl]-3-(3-fluorophenyl)quinolin-6-yl}-4-methylpyridin-3-amine (1-8)

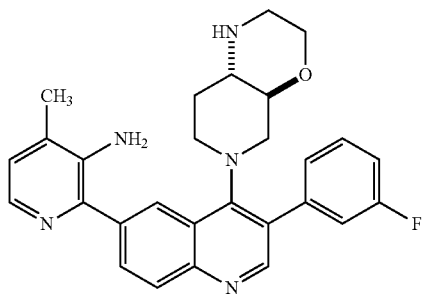

Step 1-1. Preparation of benzyl (4aS,8aS)-6-[3-chloro-6-(4,4,5,5-tetramethyl-1,3,2-dioxaborolan-2-yl)quinolin-4-yl]-octahydro-1H-pyrido[3,4-b][1,4]oxazine-1-carboxylate To a dioxane solution (3.0 mL) of benzyl (4aS,8aS)-6-(6-bromo-3-chloroquinolin-4-yl)-octahydro-1H-pyrido[3,4-b][1,4]oxazine-1-carboxylate (1.0 equiv, 0.29 mmol, 150 mg) was added 4,4,5,5-tetramethyl-2-(4,4,5,5-tetramethyl-1,3,2-dioxaborolan-2-yl)-1,3,2-dioxaborolane (2.0 equiv, 0.58 mmol, 147 mg), KOAc (3.0 equiv, 0.87 mmol, 85 mg), and Pd(dppf)Cl$_2$ (0.06 equiv, 0.02 mmol, 12 mg) under atmospheric N$_2$. The resulting mixture was heated at 90° C. for 1 h and then cooled down to ambient temperature. The reaction solution was concentrated under vacuum to afford 170 mg of the crude product. This material was used for next step without further purification.

Step 1-2. Preparation of benzyl (4aS,8aS)-6-[6-(3-amino-4-methylpyridin-2-yl)-3-chloroquinolin-4-yl]-octahydro-1H-pyrido[3,4-b][1,4]oxazine-1-carboxylate To a dioxane solution (4.0 mL) of crude benzyl (4aS,8aS)-6-[3-chloro-6-(4,4,5,5-tetramethyl-1,3,2-dioxaborolan-2-yl)quinolin-4-yl]-octahydro-1H-pyrido[3,4-b][1,4]oxazine-1-carboxylate (1.0 equiv, 0.29 mmol, 170 mg) was added 2-bromo-4-methylpyridin-3-amine (1.0 equiv, 0.29 mmol, 56 mg), Pd(Amphos)Cl$_2$ (0.10 equiv, 0.029 mmol, 21 mg), K$_2$CO$_3$ (3.0 equiv, 0.90 mmol, 125 mg), and water (0.4 mL) under atmospheric N$_2$. The resulting mixture was heated at 90° C. for 2 h. The reaction mixture was cooled down to ambient temperature and concentrated under vacuum. The residue obtained was purified by silica gel chromatography eluting with ethyl acetate/petroleum ether (3:1) to afford 70 mg of the desired product as yellow oil. MS (M+H)$^+$=544.2.

Step 1-3. Preparation of benzyl (4aS,8aS)-6-[6-(3-amino-4-methylpyridin-2-yl)-3-(3-fluorophenyl)quinolin-4-yl]-octahydro-1H-pyrido[3,4-b][1,4]oxazine-1-carboxylate To a toluene solution (3.0 mL) of benzyl (4aS,8aS)-6-[6-(3-amino-4-methylpyridin-2-yl)-3-chloroquinolin-4-yl]-octahydro-1H-pyrido[3,4-b][1,4]oxazine-1-carboxylate (1.0 equiv, 0.13 mmol, 70 mg) was added (3-fluorophenyl)boronic acid (2.0 equiv, 0.26 mmol, 36 mg), Pd(Amphos)Cl$_2$ (0.10 equiv, 0.013 mmol, 9 mg), K$_2$CO$_3$ (3.0 equiv, 0.38 mmol, 53 mg), and water (0.3 mL) under atmospheric N$_2$. The resulting mixture was heated at 110° C. for 1 h. The reaction mixture was cooled down to ambient temperature and concentrated under vacuum. The residue obtained was purified by silica gel chromatography eluting with ethyl acetate/petroleum ether (1:1) to afford 50 mg of the desired product as yellow oil. MS (M+H)$^+$=604.3.

Step 1-4. Preparation of 2-{4-[(4aS,8aS)-octahydro-1H-pyrido[3,4-b][1,4]oxazin-6-yl]-3-(3-fluorophenyl)quinolin-6-yl}-4-methylpyridin-3-amine Benzyl (4aS,8aS)-6-[6-(3-amino-4-methylpyridin-2-yl)-3-(3-fluorophenyl)quinolin-4-yl]-octahydro-H-pyrido[3,4-b][1,4]oxazine-1-carboxylate (1.0 equiv, 0.08 mmol, 50 mg) was combined with trifluoroacetic acid (2.0 mL) and the resulting mixture was heated at 80° C. for 2 h. The reaction solution was cooled down to ambient temperature and concentrated under vacuum. The residue obtained was purified by Prep-HPLC with the following conditions (Prep-HPLC-007): Column, SunFire Prep C18 OBD Column, 19*150 mm, 5 um, 10 nm; mobile phase, Water (0.1% TFA) and ACN (2.0% ACN up to 20.0% in 6 min, hold at 95% for 1 min, down to 2.0% in 1 min, hold at 2.0% for 1 min); Detector, UV 220 nm. This resulted in 11.4 mg (27%) of formic acid salt of 2-{4-[(4aS,8aS)-octahydro-1H-pyrido[3,4-b][1,4]oxazin-6-yl]-3-(3-fluorophenyl)quinolin-6-yl}-4-methylpyridin-3-amine as a yellow solid. MS (M+H)$^+$=470.2.

The following compounds were prepared similarly to Example 25 with appropriate substituting of reagents and substrates at different steps and additional functional group modifications via well-known chemistry with appropriate reagents as required. Different salts such as HCl or formic acid may be obtained through conventional methods.

| Compound no. | MS (M + H)$^+$ |
|---|---|
| 1-1 | 517.2 |
| 1-2 | 527.3 |
| 1-3 | 547.1 |
| 1-4 | 495.2 |
| 1-5 | 515.2 |
| 1-6 | 517.2 |
| 1-7 | 481.2 |
| 1-9 | 471.2 |
| 1-10 | 471.2 |

Example A-1: Parenteral Pharmaceutical Composition

To prepare a parenteral pharmaceutical composition suitable for administration by injection (subcutaneous, intravenous), 1-100 mg of a water-soluble salt of a compound disclosed herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound disclosed herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound disclosed herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound disclosed herein, or a pharmaceutically acceptable salt thereof, is optionally mixed with starch or other suitable powder blends. The mixture is incorporated into an oral dosage unit such as a hard gelatin capsule, which is suitable for oral administration.

In another embodiment, 10-500 mg of a compound disclosed herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound disclosed herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: SSTR Assays

Functional Assay for SSTR2 Agonists

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology*, 2005, 2.2.1-2.2). Human SSTR2 intracellular cAMP assay is described below. The human SSTR1, 3, 4 and 5 assays follow the same protocol of SSTR2.

cAMP Assay Protocol:

Four days prior to the assay, 5,000 Chinese hamster ovary cells (CHO-K1, ATCC #CCL-61) stably expressing the human SSTR2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 µL of lysis buffer (HRTF cAMP kit, Cisbio). The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6.

Illustrative biological activity of compounds is demonstrated in the following table by evaluating the inhibition of cAMP activities via human SST2R, where A means <10 nM; B means ≥10 nM and <100 nM; C means ≥100 nM and <1000 nM; D means ≥1000 nM

| Compound no. | $EC_{50}$ |
| --- | --- |
| Compound A | A |
| 1-1 | A |
| 1-2 | A |
| 1-3 | A |
| 1-4 | A |
| 1-5 | A |
| 1-6 | A |
| 1-7 | A |
| 1-8 | A |
| 1-9 | A |
| 1-10 | A |

The examples and embodiments described herein are for illustrative purposes only and various modifications or changes suggested to persons skilled in the art are to be included within the spirit and purview of this application and scope of the appended claims.

What is claimed is:

1. A method of treating acromegaly or a neuroendocrine tumor, or combination thereof, in a human comprising orally administering to the human with acromegaly or a neuroendocrine tumor, or combination thereof, a pharmaceutical composition comprising the compound 3-[4-(4-amino-piperidin-1-yl)-3-(3,5-difluoro-phenyl)-quinolin-6-yl]-2-hydroxy-benzonitrile monohydrochloride, or solvate thereof; and at least one pharmaceutically acceptable excipient, wherein 3-[4-(4-amino-piperidin-1-yl)-3-(3,5-difluoro-phenyl)-quinolin-6-yl]-2-hydroxy-benzonitrile monohydrochloride, or solvate thereof is crystalline and is characterized as having: an X-ray powder diffraction (XRPD) pattern with peaks at 4.5° 2-Theta, 9.1° 2-Theta, 10.2° 2-Theta, 16.3° 2-Theta, 18.4° 2-Theta, and 19.1° 2-Theta; an X-ray powder diffraction (XRPD) pattern substantially the same as shown in FIG. 1; a Differential Scanning calorimetry (DSC) thermogram with an endotherm having an onset at about 207° C. and a peak at about 220° C.; a Differential Scanning calorimetry (DSC) thermogram substantially the same as shown in FIG. 2(*a*); an infrared (IR) spectrum with peaks at 2223 $cm^{-1}$, 1620 $cm^{-1}$, 1595 $cm^{-1}$, 1457 $cm^{-1}$, 1238 $cm^{-1}$, 1220 $cm^{-1}$, and 1117 $cm^{-1}$; an infrared (IR) spectrum substantially the same as shown in FIG. 3; an unchanged XRPD when heated up to about 200° C., upon exposure to more than 90% relative humidity for about 24 hours, or upon exposure to about 75% RH and 40° C. over one week, or combinations thereof; or combinations thereof.

2. The method of claim 1, wherein the pharmaceutical composition comprises 1-100 mg of 3-[4-(4-amino-piperidin-1-yl)-3-(3,5-difluoro-phenyl)-quinolin-6-yl]-2-hydroxy-benzonitrile monohydrochloride, or solvate thereof.

3. The method of claim 1, wherein the pharmaceutical composition is orally administered to the human once a day.

4. The method of claim 1, wherein the pharmaceutical composition is in the form of a solid form pharmaceutical composition.

5. The method of claim 1, wherein the pharmaceutical composition is in the form of a capsule.

6. The method of claim 5, wherein the capsule is orally administered to the human once a day.

7. The method of claim 1, wherein the pharmaceutical composition is in the form of a capsule and comprises 10 mg of 3-[4-(4-amino-piperidin-1-yl)-3-(3,5-difluoro-phenyl)-quinolin-6-yl]-2-hydroxy-benzonitrile monohydrochloride, or solvate thereof.

8. The method of claim 7, wherein the capsule is orally administered to the human once a day.

9. The method of claim 1, wherein the pharmaceutical composition is in the form of a tablet.

10. The method of claim 9, wherein the tablet is orally administered to the human once a day.

* * * * *